US008084612B2

(12) United States Patent
Shao et al.

(10) Patent No.: US 8,084,612 B2
(45) Date of Patent: Dec. 27, 2011

(54) PROLINE ANALOGS AS LIGANDS FOR CANNABINOID RECEPTORS

(75) Inventors: Bin Shao, Richboro, PA (US); Jiangchao Yao, Monmouth Junction, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 12/350,450

(22) Filed: Jan. 8, 2009

(65) Prior Publication Data

US 2009/0291947 A1 Nov. 26, 2009

Related U.S. Application Data

(60) Provisional application No. 61/010,447, filed on Jan. 8, 2008.

(51) Int. Cl.
C07D 409/12 (2006.01)
(52) U.S. Cl. ........................................ 546/202; 548/525
(58) Field of Classification Search .................. None
See application file for complete search history.

(56) References Cited

U.S. PATENT DOCUMENTS

| | | | |
|---|---|---|---|
| 4,008,719 A | 2/1977 | Theeuwes et al. |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshlack et al. |
| 5,922,740 A | 7/1999 | Braunlich et al. |
| 6,136,839 A | 10/2000 | Isakson et al. |
| 6,271,252 B1 | 8/2001 | Chang et al. |
| 6,852,748 B1 | 2/2005 | Kelly et al. |
| 2007/0287744 A1 | 12/2007 | Barth et al. |

FOREIGN PATENT DOCUMENTS

| | | | |
|---|---|---|---|
| ES | 2008634 A6 | 7/1989 |
| WO | WO 93/19070 | * | 9/1993 |
| WO | WO 99/26615 A1 | 3/1999 |
| WO | WO 2004/012671 A2 | 2/2004 |
| WO | WO 2004/041273 A1 | 5/2004 |
| WO | WO 2005/115977 A1 | 12/2005 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
ACS on STN, list of 20 compounds, dated Mar. 21, 2008.*
ACS on STN list of 20 compounds, dated Mar. 21, 2008. Ahmad et al., "Novel G protein-coupled receptors as pain targets," *Curr. Opin. Invest. Drugs* 5(1):67-70 (2004).
Bagshaw, "Medical Efficacy of Cannabinoids and Marijuana: a Comprehensive Review of the Literature," *J. Palliative Care* 18(2):111-122 (2002).
Black, "Cannabinoid receptor antagonists and obesity," *Curr. Opin. Investig. Drugs* 5(4):389-394 (2004).

Buchwald et al., "Long-term, Continuous Intravenous Heparin Administration by an Implantable Infusion Pump in Ambulatory Patients with Recurrent Venous Thrombosis," *Surgery* 88:507-516 (1980).
Chang et al., "Highly constrained bicyclic VLA-4 antagonists," *Bioorganic & Med. Chem Let.* 17:597-601 (2007).
Cheng et al., "Relationship between the inhibition constant, Ki, and the concentration of inhibitor which causes 50% inhibition (I50) of an enzymatic reaction," *Biochem. Pharmacol.* 22:3099-3108 (1973).
Cichewicz, "Synergistic interactions between cannabinoid and opioid analgesics," *Life Sciences* 74:1317-1324 (2004).
Croxford, "Therapeutic potential of cannabinoids in CNS disease," *CNS Drugs* 17(3):179-202 (2003).
During et al., "Controlled Release of Dopamine from a Polymeric Brain Implant: In Vivo Characterization," *Ann. Neurol.* 25:351-356 (1989).
Fernandez et al., "Rimonabant," *Curr. Opin. Investig. Drugs* 5(4):430-435 (2004).
Goodson, "Dental Applications," pp. 115-138 in *Medical Applications of Controlled Release, vol. 2 , Applications and Evaluation*, Langer and Wise, Eds., CRC Press (1984).
Grotenhermen, "Pharmacology of Cannabinoids," *Neuroendocrinol. Lett.* 25(1/2):14-23 (2004).
Hanson, "Analgesic, Antipyretic and Anti-Inflammatory Drugs," pp. 1196-1221 in *Remington: The Science and Practice of Pharmacy*, vol. 2 (Gennaro Ed. $19^{th}$ Ed. 1995).
Howard et al., "Intracerebral drug delivery in rats with lesion-induced memory deficits," *J Neurosurg.* 71:105 (1989).
Howlett "International Union of Pharmacology. XXVII. Classification of cannabinoid receptors," *Pharmacol. Rev.* 54(2):161-202 (2002).
Howlett, "The cannabinoid receptors," *Prostaglandins and other Lipid Mediators* 68-69:619-631 (2002).
Insel, "Analgesic-Antipyretic and Anti-inflammatory Agents and Drugs Employed in the Treatment of Gout," in *Goodman & Gilman's The Pharmacological Basis of Therapeutics* pp. 617-657 (Goodman et al., eds., $9^{th}$ ed., McGraw-Hill, New York 1996).
Lange et al., "Recent advances in CB1 cannabinoid receptor antagonists," *Curr. Opin. Drug Disc. & Devel.* 7(4):498-506 (2004).
Langer et al., "Chemical and Physical Structure of Polymers as Carriers for Controlled Release of Bioactive Agents: A Review," *J. Macromol. Sci. Rev. Macromol. Chem.* C23(1):61-126 (1983).
Langer et al., "Classes of Systems," *Medical Applications of Controlled Release* vol. I, CRC Press, Boca Raton, FL (1984).
Langer, "New Methods of Drug Delivery," *Science* 249:1527-1533 (1990).
Levy, "Inhibition of Calcification of Bioprosthetic Heart Valves by Local Controlled-Release Diphosphonate," *Science* 228:190-192 (1985).
Mackie et al., "Cannabinoids activate an inwardly rectifying potassium conductance and inhibit Q-type calcium currents in AtT20 cells transfected with rat brain cannabinoid receptor," *J. Neurosci* 15(10):6552-6561 (1995).
Neff et al., "Preliminary observation with dronabinol in patients with intractable pruritus secondary to cholestatic liver disease," *Am. J. Gastroenterol.* 97(8):2117-2119 (2002).
PCT International Search Report for International Application No. PCT/IB2009/000023 dated Apr. 21, 2009.
Pertwee et al., "Cannabinoid receptors and their ligands," *Prostaglandins, Leukotrienes and Essential Fatty Acids* 66(2&3):101-121 (2002).
Piomelli, "The molecular logic of endo-cannabinoid signaling," *Nature Revs. (Neuroscience)* 4:873-884 (2003).
Radebough et al., "Preformulation," pp. 1447-1676 in *Remington's Pharmaceutical Sciences* (Gennaro, Ed., $19^{th}$ Ed., 1995).
Ross et al., "Pharmacodynamics: Mechanisms of Drug Action and the Relationship Between Drug Concentration and Effect," in *Goodman & Gilman's the Pharmacological Basis of Therapeutics* Chapter 2, pp. 31-32 (Hardman et al., eds., $10^{th}$ ed., McGraw-Hill, New York 2001).
Saudek et al., "A Preliminary Trial of the Programmable Implantable Medication System for Insulin Delivery," *New Engl. J. Med.* 321:574-579 (1989).

Sefton, "Implantable Pumps," *CRC Crit. Rev. Biomed. Eng.* 14(3):201-240 (1987).
Smolen et al., "Drug Product Design and Performance," *Controlled Drug Bioavailability* vol. 1, John Wiley & Sons, New York (1984).
Tomida et al., "Cannabinoids and glaucoma," *Br. J. Ophthalmol.* 88:708-713 (2003).
Treat et al., "Liposome Encapsulated Doxorubicin Preliminary Results of Phase I and Phase II Trials," *Liposomes in the Therapy of Infectious Disease and Cancer* pp. 317-327 and 353-365 (1989).
Walker et al. "Cannabinoid analgesia," *Pharmacol. Therapeut.* 95:127-135 (2002).

\* cited by examiner

*Primary Examiner* — Rebecca Anderson
*Assistant Examiner* — Alicia L Otton
(74) *Attorney, Agent, or Firm* — Dechert LLP

(57) ABSTRACT

The invention relates to compounds of Formulae I(a) to XI

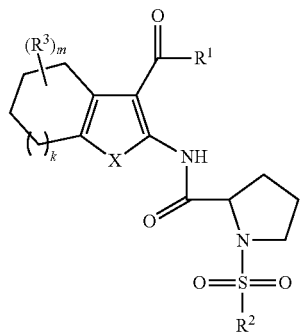

I(a)

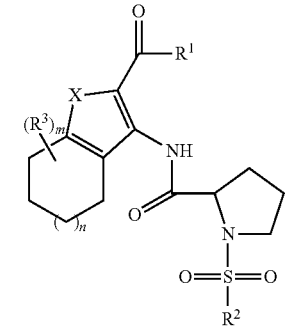

I(b)

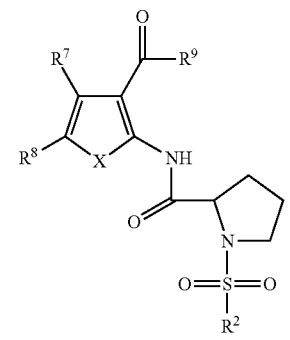

II(a)

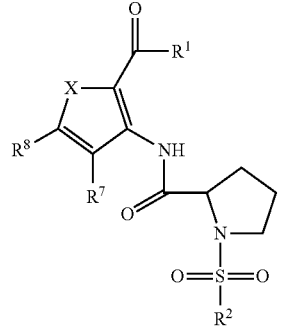

II(b)

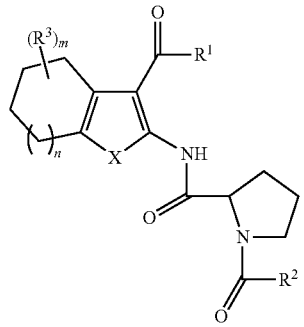

III(a)

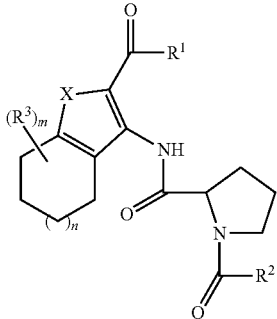

III(b)

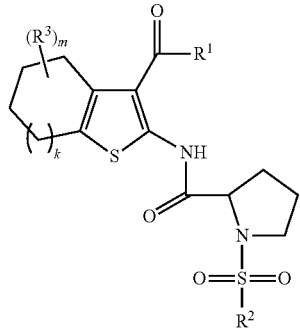

IV(a)

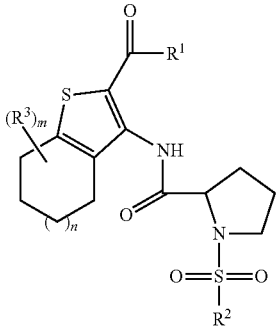

IV(b)

-continued
V(a)
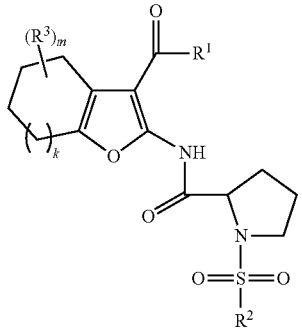
V(b)
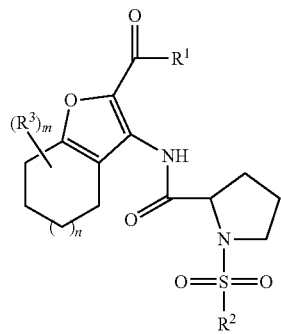
VI(a)
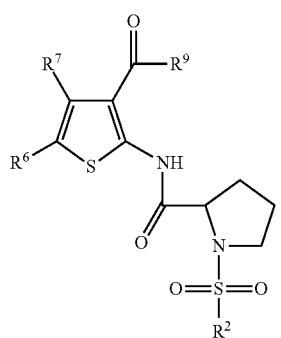
VI(b)
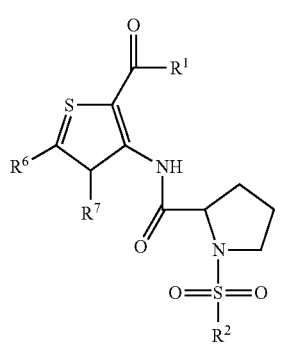
VII(a)
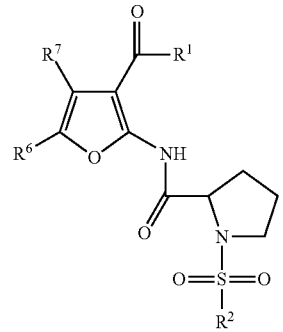
VII(b)
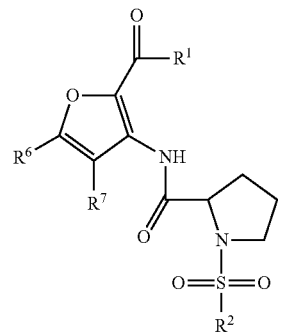
VIII(a)
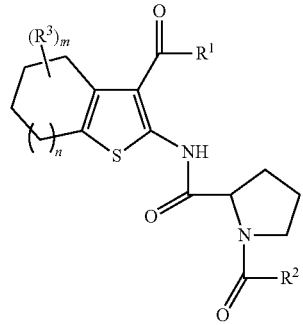
VIII(b)
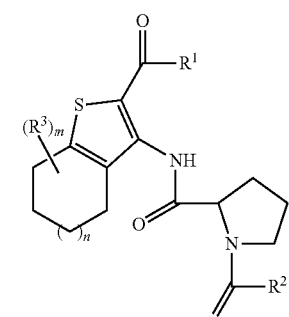
IX(a)
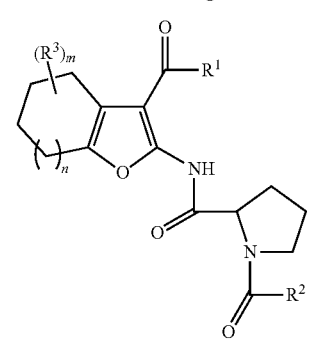

-continued

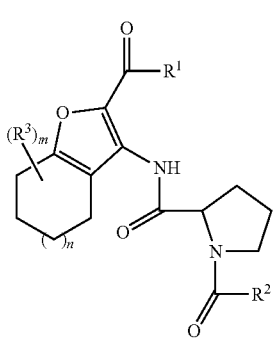

IX(b)

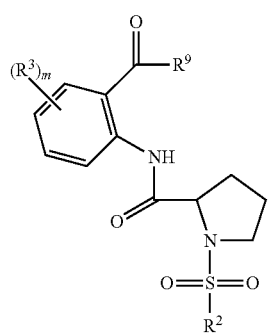

X

-continued

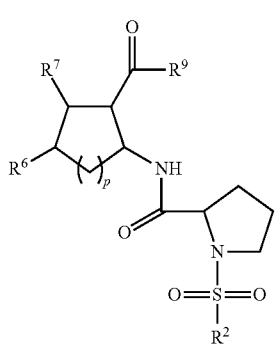

XI and pharmaceutically acceptable salts and solvates thereof (Proline Analog Compounds), that are useful, e.g., as ligands for cannabinoid receptors, as compositions comprising a Proline Analog Compound and a pharmaceutically acceptable carrier, in methods of making such Proline Analog Compounds, and in methods for treating or preventing a Condition, such as pain, nausea, vomiting and an eating disorder, comprising administering an effective amount of a Proline Analog Compound to an animal in need thereof.

32 Claims, No Drawings

PROLINE ANALOGS AS LIGANDS FOR CANNABINOID RECEPTORS

1. CROSS-REFERENCE TO RELATED APPLICATIONS

This application claims the benefit under 35 U.S.C. §119 (e) of U.S. Provisional Patent Application No. 61/010,447, filed on Jan. 8, 2008, the contents of which are incorporated herein by reference.

2. FIELD OF THE INVENTION

The present invention relates to Proline Analog Compounds that are ligands for cannabinoid receptors, compositions comprising a Proline Analog Compound and a pharmaceutically-acceptable carrier, methods of making such Proline Analog Compounds, and methods for treating or preventing a Condition comprising administering an effective amount of a Proline Analog Compound to an animal in need thereof.

3. BACKGROUND OF THE INVENTION

Cannabinoid receptors belong to the G-protein coupled ("GPCR") receptor superfamily. Cannabinoid receptors include at least two subtypes, referred to as $CB_1$ and $CB_2$, which are distinguished by their amino acid sequence, tissue distribution, signaling mechanisms, and ability to bind subtype-specific ligands. $CB_1$ receptors are found in the central and peripheral nervous systems, while $CB_2$ receptors are primarily expressed by cells of the immune system (Howlett (2002) *Prostaglandins and other Lipid Mediators* (68-69): 619-631; Pertwee et al. (2002) *Prostaglandins, Leukotrienes and Essential Fatty Acids* 66(2&3): 101-121; Piomelli (2003) *Nature Reviews* (Neuroscience) 4: 873-884.

Agonist binding to $CB_1$ and $CB_2$ receptors initiates signals that are transduced via $G_{i/o}$ proteins coupled to the cannabinoid receptors. The transduced signals lead to inhibition of stimulus-induced adenylate cyclase, inhibition of cAMP/protein Innase A-mediated effects, and stimulation of mitogen-activated protein kinase. Agonist binding to $CB_1$ receptors also inhibits voltage-gated $Ca^{+2}$ channels and stimulates inwardly-rectifying $K^+$ channels (Mackie et al. (1995) *J. Neurosci* 15(10): 6552-61). Stimulation of presynaptic $CB_1$ receptors by agonist binding has been reported to inhibit neurotransmitter release in both the central and peripheral nervous systems (Howlett (2002) *Pharmacol. Rev.* 54(2): 161-202; Pertwee et al. (2002) *Prostaglandins, Leukotrienes and Essential Fatty Acids* 66(2&3): 101-121).

Cannabinoid receptor ligands can be characterized by both their selectivity (e.g. binding strength to cannabinoid receptors) and their specificity (e.g. relative binding strength to a $CB_1$ receptor as compared to a $CB_2$ receptor). Moreover, cannabinoid receptor ligands may be characterized as agonists, antagonists or inverse agonists of the receptor to which they bind. Accordingly, specific cannabinoid receptor ligands can induce profoundly different biochemical and physiological effects and, therefore, will have different therapeutic applications, as evident from the abbreviated list provided below.

For example, cannabinoids have been described as useful for the treatment of nausea and vomiting associated with administration of anti-neoplastic agents to cancer patients (Bagshaw (2002) *J. Palliative Care* 18(2): 111-122; Grotenhermen (2004) *Neuroendocrinol. Lett.* 25(1/2): 1423).

The cannabinoid system has also been reported to be directly involved in the regulation of physiological processes central to the control of appetite and body weight. Administration of cannabinoid receptor agonists has been shown to stimulate the appetite of HIV/AIDS patients afflicted with anorexia and cachexia. Administration of cannabinoid receptor antagonists/inverse agonists has been described as appetite depressants useful for the treatment and prevention of obesity (Lange et al. (2004) *Curr. Opin. Drug Disc. & Devel.* 7(4): 498-506; Black (2004) *Curr. Opin. Investig. Drugs* 5(4): 389-94; Fernandez et al. (2004) *Curr. Opin. Investig. Drugs* 5(4): 430-435). For example, administration of the $CB_1$ receptor antagonist (SR 141716A) has been reported to induce a reduction in body weight and adiposity in rodents.

Cannabinoids have also been reported to be therapeutically-useful for the treatment of diseases characterized by muscle spasticity, spasm, or tremor. In particular, cannabinoids have been reported as capable of alleviating the spasticity associated with spinal cord injury and multiple sclerosis, as well as movement disorders associated with Tourette's syndrome and L-dopa-induced dyskenesia of Parkinson's disease (Grotenhermen (2004) *Neuroendocrinol. Lett.* 25(1/2): 14-23; Croxford (2003) *CNS Drugs* 17(3): 179-202).

Cannabinoid receptor agonists have been reported to attenuate pain in vivo and therefore are potentially useful for the alleviation of acute and chronic pain (Ahmad et al. (2004) *Curr. Opin. Invest. Drugs* 5(1): 67-70; Cichewicz (2004) *Life Sciences* 74: 1317-24; Walker et al. (2002) *Pharmacol. Therapeut.* 95: 127-135).

Cannabinoids have been reported to lower intraocular pressure, apparently via binding to intraocular $CB_1$ receptors. Accordingly, it has been suggested in the art that such ligands may be useful for the prevention and treatment of glaucoma (Tomida et al. (2003) *Br. J. Opthamol* 88: 708-713). The term "glaucoma" comprises a set of diseases of the eye involving injury to the optic nerve. In certain instances, increased pressure within the eye leads to mechanical compression of and/or inhibition of blood flow to the optic nerve. The final stage of visual loss involves selective apoptosis of retinal ganglion cells as a result of compressive and/or ischemic injury to axons at the optical disc (Tomida et al. (2003) *Br. J. Opthamol* 88: 708-71).

Pruritus (an unpleasant sensation that prompts scratching) has been treated by phototherapy with ultraviolet B or PUVA (administration of psoralen followed by exposure of the target tissue to long-wavelength ultraviolet light), and with therapeutic agents such as naltrexone, nalmefene, danazol, and tricyclic antidepressants. More recently, administration of the cannabinoid $\Delta^9$-tetrahydrocannabinol ("$\Delta^9$-THC") has been reported to result in a decrease in pruritus in patients who had not responded to conventional treatments (Neff et al. (2002) *Am. J. Gastroenterol.* 97(8): 2117-2119).

Citation of any reference in Section 2 of this application is not intended as an admission that such reference is prior art to the present application.

4. SUMMARY OF THE INVENTION

The present invention encompasses compounds of Formula I(a):

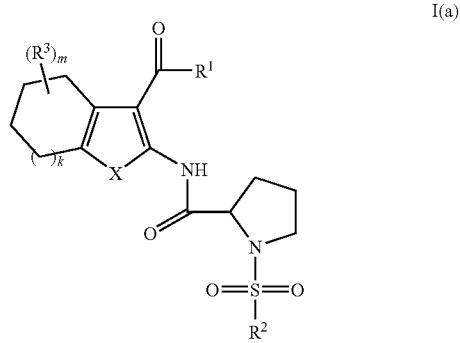

I(a)

and pharmaceutically acceptable salts and solvates thereof, wherein:

X is S or O;

$R^1$ is —($C_3$-$C_{10}$ alkyl), —O($C_1$-$C_{10}$ alkyl), —NH($C_1$-$C_4$ alkyl), —N($C_1$-$C_4$ alkyl)$_2$,

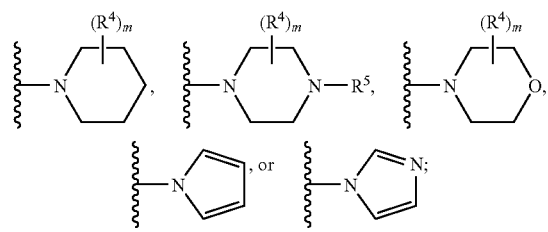

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with one, two, or three $R^3$ groups;

each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;

each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);

$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;

each halo is independently —F, —Cl, —Br, or —I;

k is an integer selected from the group consisting of 2, 3, and 4; and each m is independently an integer selected from the group consisting of 0, 1, 2, 3, and 4.

The present invention further encompasses compounds of formula I(b):

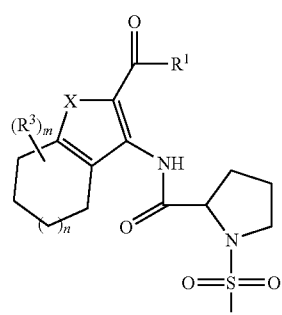

I(b)

and pharmaceutically acceptable salts and solvates thereof, wherein:

X is S or O;

$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

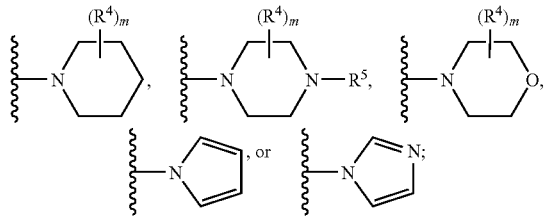

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with one, two, or three $R^3$ groups;

each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;

each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);

$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;

each halo is independently —F, —Cl, —Br, or —I;

n is an integer selected from the group consisting of 0, 1, 2, 3, and 4; and each m is independently an integer selected from the group consisting of 0, 1, 2, 3, and 4.

The present invention further encompasses compounds of formula III(a):

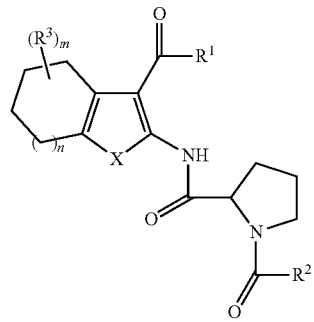

III(a)

and pharmaceutically acceptable salts and solvates thereof, wherein:

X is S or O;

$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

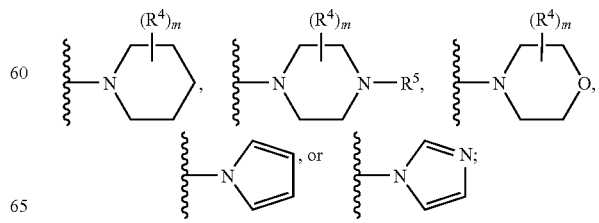

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with one, two, or three $R^3$ groups;

each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;

each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);

$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N(CO$_1$C$_4$ alkyl)$_2$, where r is an integer selected from the group consisting of 1, 2, 3, and 4;

each halo is independently —F, —Cl, —Br, or —I;

n is an integer selected from the group consisting of 0, 1, 2, 3, and 4; and each m is independently an integer selected from the group consisting of 0, 1, 2, 3, and 4.

The present invention further encompasses compounds of formula III(b):

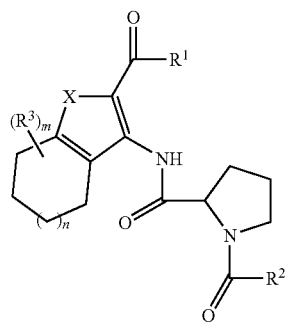

III(b)

and pharmaceutically acceptable salts and solvates thereof, wherein:

X is S or O;

$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

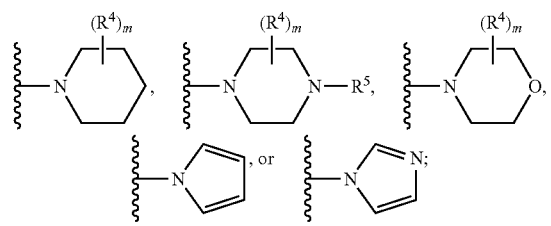

$R^2$ is —($C_1$-$C_{10}$ aryl), —($C_3$-$C_{10}$) cycloakyl, phenyl, naphthyl, anthryl, phenanthryl, or -(5 to 7 membered) heteroaryl, each being unsubstituted or substituted with one, two, or three $R^3$ groups;

each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;

each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);

$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;

each halo is independently —F, —Cl, —Br, or —I;

n is an integer selected from the group consisting of 0, 1, 2, 3, and 4; and each m is independently is an integer selected from the group consisting of 0, 1, 2, 3, and 4.

The present invention further encompasses compounds having the formula II(a):

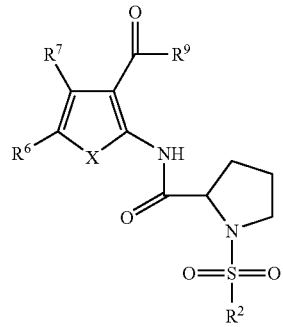

II(a)

and pharmaceutically acceptable salts and solvates thereof, wherein:

X is S or O;

$R^9$ is —($C_1$-$C_{10}$ alkyl), —NH($C_1$-$C_4$ alkyl), —N($C_1$-$C_4$ alkyl)$_2$,

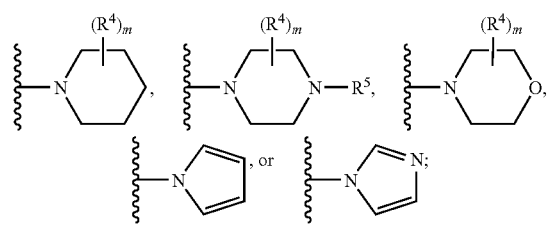

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with one, two, or three $R^3$ groups;

each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;

each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);

$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;

wherein each $R^6$ and $R^7$ is independently H, —($C_1$-$C_{10}$ alkyl), —CH$_2$O($C_1$-$C_4$ alkyl), —CH$_2$NH($C_1$-$C_4$ alkyl), —CH$_2$N($C_1$-$C_4$ alkyl)$_2$, —($C_3$-$C_8$)cycloalkyl either unsubstituted or substituted with one, two, or three $R^3$ groups, phenyl either unsubstituted or substituted with one, two, or three $R^3$ groups, or -(5 to 7 membered)heteroaryl either unsubstituted or substituted with one to three $R^3$ groups, or $R^6$ and R⁷ taken together with the carbon atoms to which they are attached form a -(5 to 7 membered)heteroaryl ring optionally substituted with one, two, or three R³ groups or R⁶ and R⁷ taken together with the carbon atoms to which they are attached form an aromatic six-membered carbocyclic ring optionally substituted with one, two, or three R³ groups;

each halo is independently —F, —Cl, —Br, or —I; and m is an integer selected from the group consisting of 0, 1, 2, 3, and 4.

The present invention further encompasses compounds of formula II(b):

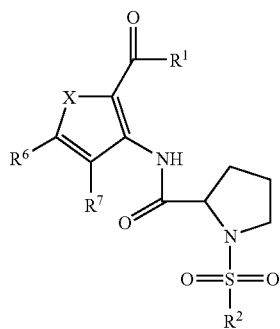

and pharmaceutically acceptable salts and solvates thereof, wherein:

X is S or O;

R¹ is —(C₁-C₁₀ alkyl), —O(C₁-C₁₀ alkyl), —NH(C₁-C₄ alkyl), —N(C₁-C₄ alkyl)₂,

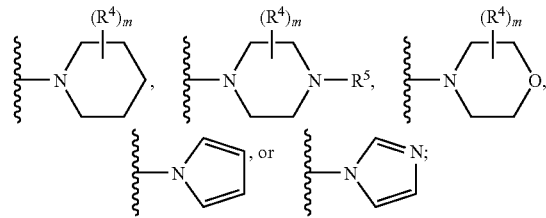

R² is —(C₁-C₁₀ alkyl), —(C₃-C₈) cycloalkyl, phenyl, naphthyl, anthryl, phenanthryl, or -(5 to 7 membered) heteroaryl, each being unsubstituted or substituted with one, two, or three R³ groups;

each R³ is independently -halo, —C(halo)₃, —CH(halo)₂, —CH₂(halo), —CN, —OH, —NO₂, —NH₂, —NH(C₁-C₄ alkyl), —N(C₁-C₄ alkyl)₂, —(C₁-C₁₀ alkyl), —O(C₁-C₄ alkyl), —CONH₂, —CONH(C₁-C₄ alkyl), or —CON(C₁-C₄ alkyl)₂;

each R⁴ is independently -halo, —C(halo)₃, —CH(halo)₂, —CH₂(halo), —OH, —(C₁-C₄ alkyl), or —O(C₁-C₄ alkyl);

R⁵ is —H, —C(halo)₃, —CH(halo)₂, —CH₂(halo), —(C₁-C₁₀ alkyl), —(CH₂)ᵣO(C₁-C₄ alkyl), —(CH₂)ᵣNH(C₁-C₄ alkyl)₇ or —(CH₂)ᵣN(C₁-C₄ alkyl)₂, where r is an integer selected from the group consisting of 1, 2, 3, and 4;

each halo is independently —F, —Cl, —Br, or —I;

wherein each R⁶ and R⁷ is independently H, —(C₁-C₁₀ alkyl), —CH₂O(C₁-C₄ alkyl), —CH₂NH(C₁-C₄ alkyl), —CH₂N(C₁-C₄ alkyl)₂, —(C₃-C₈)cycloalkyl either unsubstituted or substituted with one to three R³ groups, phenyl either unsubstituted or substituted with one, two, or three R³ groups, or -(5 to 7 membered)heteroaryl either unsubstituted or substituted with one, two, or three R³ groups, or R⁶ and R⁷ taken together with the carbon atoms to which they are attached form a -(5 to 7 membered)heteroaryl ring optionally substituted with one to three R³ groups or R⁶ and R⁷ taken together with the carbon atoms to which they are attached form an aromatic six-membered carbocyclic ring optionally substituted with one to three R³ groups; and m is an integer selected from the group consisting of 0, 1, 2, 3, and 4.

The present invention further encompasses compounds of formula X:

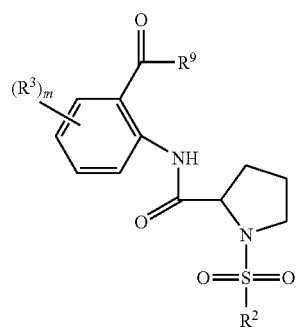

or a pharmaceutically acceptable salt or solvate thereof, wherein:

R⁹ is —(C₁-C₁₀ alkyl), —NH(C₁-C₄ alkyl), —N(C₁-C₄ alkyl)₂,

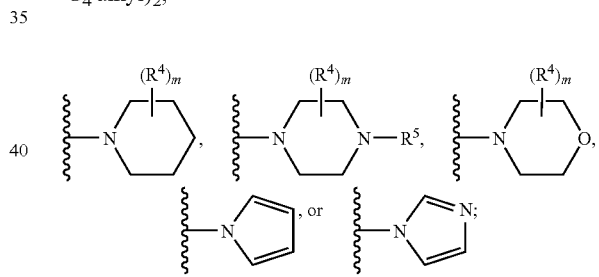

R² is —(C₁-C₁₀ alkyl), —(C₃-C₈) cycloalkyl, phenyl, naphthyl, anthryl, phenanthryl, or -(5 to 7 membered) heteroaryl, each being unsubstituted or substituted with one, two, or three R³ groups;

each R³ is independently -halo, —C(halo)₃, —CH(halo)₂, —CH₂(halo), —CN, —OH, —NO₂, —NH₂, —NH(C₁-C₄ alkyl), —N(C₁-C₄ alkyl)₂, —(C₁-C₁₀ alkyl), —O(C₁-C₄ alkyl), —CONH₂, —CONH(C₁-C₄ alkyl), or —CON(C₁-C₄ alkyl)₂;

each R⁴ is independently -halo, —C(halo)₃, —CH(halo)₂, —CH₂(halo), —OH, —(C₁-C₄ alkyl), or —O(C₁-C₄ alkyl);

R⁵ is —H, —C(halo)₃, —CH(halo)₂, —CH₂(halo), —(C₁-C₁₀ alkyl), —(CH₂)ᵣO(C₁-C₄ alkyl), —(CH₂)ᵣNH(C₁-C₄ alkyl), or —(CH₂)ᵣN(C₁-C₄ alkyl)₂, where r is an integer selected from the group consisting of 1, 2, 3, and 4;

each halo is independently —F, —Cl, —Br, or —I; and each m is independently an integer selected from the group consisting of 0, 1, 2, 3, and 4.

The present invention further encompasses compounds of formula XI:

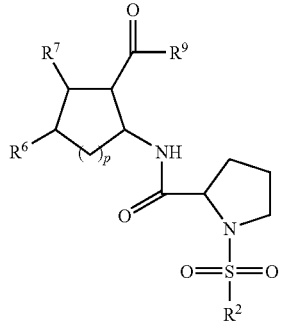

Formula XI or a pharmaceutically acceptable salt or solvate thereof, wherein:

$R^9$ is —($C_1$-$C_{10}$ alkyl), —NH($C_1$-$C_4$ alkyl), —N($C_1$-$C_4$ alkyl)$_2$,

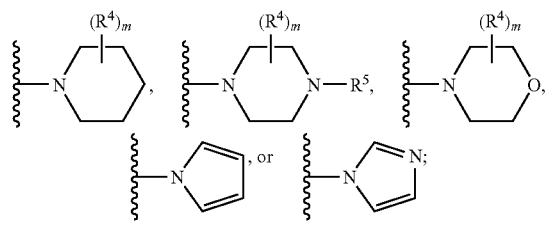

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with one, two, or three $R^3$ groups;

each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;

each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);

$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;

each halo is independently —F, —Cl, —Br, or —I;

wherein each $R^6$ and $R^7$ is independently H, —($C_1$-$C_{10}$ alkyl), —CH$_2$O($C_1$-$C_4$ alkyl), —CH$_2$NH($C_1$-$C_4$ alkyl), —CH$_2$N($C_1$-$C_4$ alkyl)$_2$, —($C_3$-$C_8$)cycloalkyl either unsubstituted or substituted with one to three $R^3$ groups, phenyl either unsubstituted or substituted with one, two, or three $R^3$ groups, or -(5 to 7 membered)heteroaryl either unsubstituted or substituted with one, two, or tree $R^3$ groups, or $R^6$ and $R^7$ taken together with the carbon atoms to which they are attached form a -(5 to 7 membered)heteroaryl ring optionally substituted with one to three $R^3$ groups or $R^6$ and $R^7$ taken together with the carbon atoms to which they are attached form an aromatic six-membered carbocyclic ring optionally substituted with one, two, or three $R^3$ groups;

p is an integer selected from the group consisting of 0, 1, 2, 3, and 4; and m is an integer selected from the group consisting of 0, 1, 2, 3, and 4.

In another embodiment the present invention also encompasses compounds of Formula II(a) and compounds of Formula II(b):

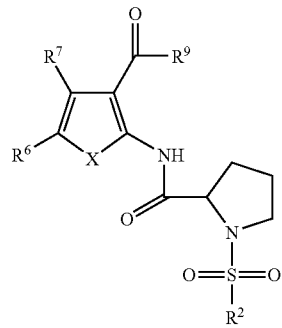

Formula II(a)

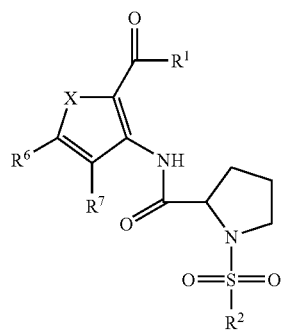

Formula II(b)

and pharmaceutically acceptable salts and solvates thereof, wherein X, $R^1$, $R^2$, $R^3$, $R^4$, $R^5$, m, and halo are as above, wherein each $R^6$ and $R^7$ is independently H, —($C_1$-$C_{10}$ alkyl), —CH$_2$O($C_1$-$C_4$ alkyl), —CH$_2$NH($C_1$-$C_4$ alkyl), —CH$_2$N($C_1$-$C_4$ alkyl)$_2$, —($C_3$-$C_8$)cycloalkyl either unsubstituted or substituted with one, two, or three $R^3$ groups, phenyl either unsubstituted or substituted with one, two, or three $R^3$ groups, or -(5 to 7 membered)heteroaryl either unsubstituted or substituted with one, two, or three $R^3$ groups, or $R^6$ and $R^7$ taken together with the carbon atoms to which they are attached form a -(5 to 7 membered)heteroaryl ring optionally substituted with one, two, or three $R^3$ groups or $R^6$ and $R^7$ taken together with the carbon atoms to which they are attached form an aromatic six-membered carbocyclic ring optionally substituted with one, two, or three $R^3$ groups; and wherein $R^9$ is —($C_1$-$C_{10}$ alkyl), —NH($C_1$-$C_4$ alkyl), —N($C_1$-$C_4$ alkyl)$_2$,

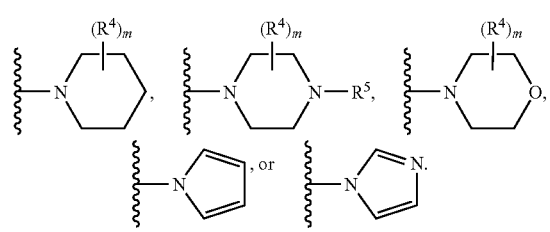

In another embodiment the present invention further encompasses compounds of Formula III(a) and compounds of Formula III(b):

Formula III(a)

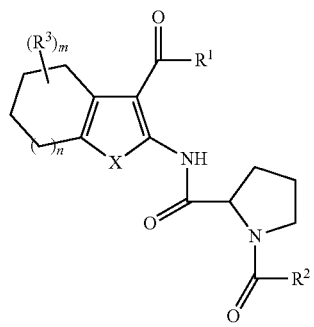

Formula III(b)

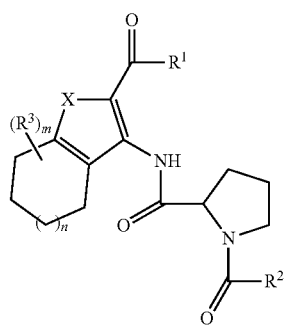

and pharmaceutically acceptable salts and solvates thereof, wherein X, $R^1$, $R^2$, $R^3$, $R^4$, $R^5$, m, n, and halo are as defined above.

Thus, the present invention encompasses compounds of Formula IV(a) and compounds of Formula V(a), as well as compounds of Formula IV(b) and compounds of Formula V(b):

Formula IV(a)

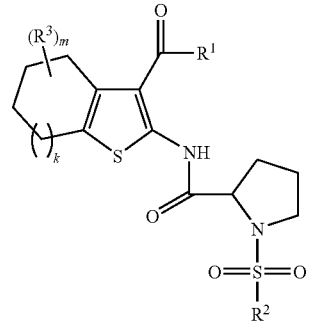

Formula V(a)

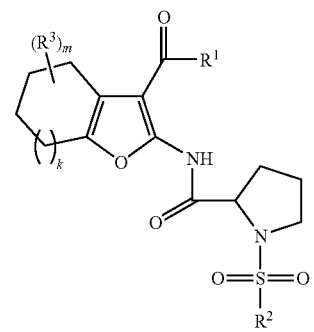

Formula IV(b)

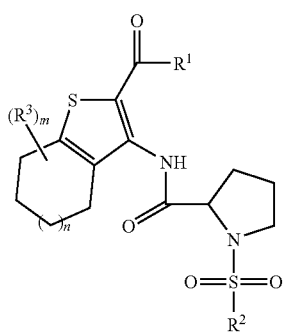

Formula V(b)

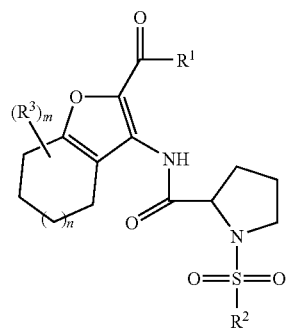

and pharmaceutically acceptable salts and solvates thereof, wherein $R^1$, $R^2$, $R^3$, $R^4$, $R^5$, k, m, n, and halo are as defined.

Similarly, the present invention also encompasses compounds of Formula VI(a) and compounds of Formula VII(a), as well as compounds of Formula VI(b) and compounds of Formula VII(b):

Formula VI(a)

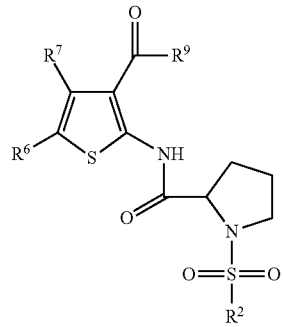

Formula VII(a)

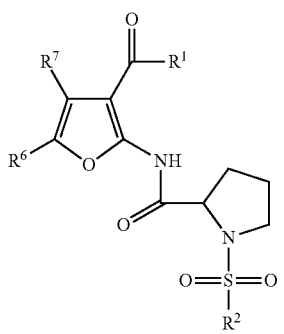

Formula VI(b)

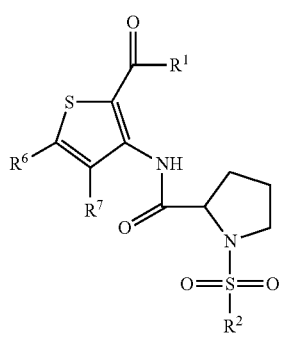

Formula VII(b)

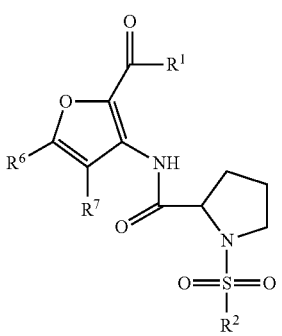

and pharmaceutically acceptable salts and solvates thereof, wherein $R^1$, $R^2$, $R^3$, $R^4$, $R^5$, $R^6$, $R^7$, $R^9$, m, and halo are as defined above.

The present invention farmer encompasses compounds of Formula VIII(a) and compounds of Formula IX(a), as well as compounds of Formula VIII(b) and compounds of Formula IX(b):

Formula VIII(a)

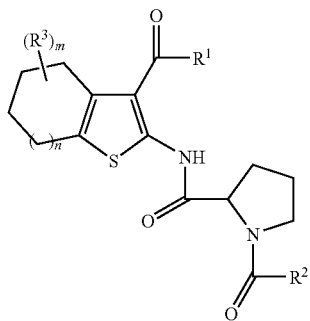

Formula IX(a)

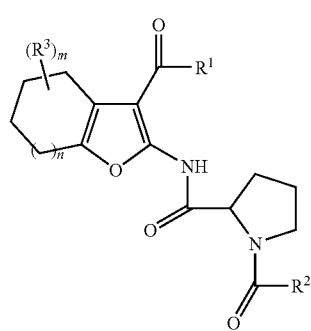

Formula VIII(b)

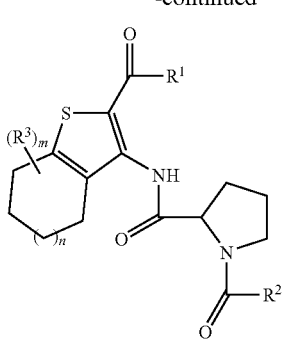

Formula IX(b)

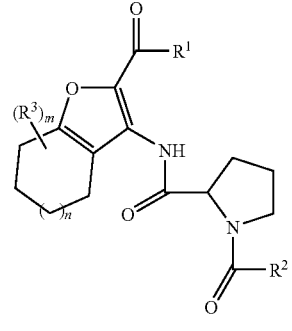

and pharmaceutically acceptable salts and solvates thereof, wherein $R^1$, $R^2$, $R^3$, $R^4$, $R^5$, m, n, and halo are as defined above.

The present invention fixer encompasses compounds of formula X:

Formula X

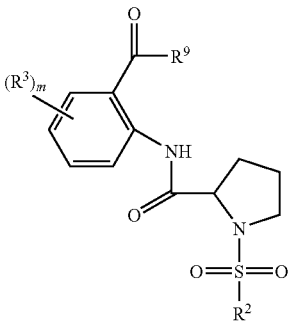

and pharmaceutically acceptable salts and solvates thereof, wherein $R^2$, $R^3$, $R^4$, $R^5$, $R^9$, m, and halo are as defined above.

The present invention also encompasses compounds of formula XI:

Formula XI

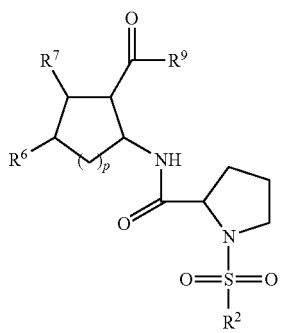

and pharmaceutically acceptable salts and solvates thereof, wherein p is an integer selected from the group consisting of 1, 2, 3, and 4, and wherein $R^2$, $R^3$, $R^4$, $R^5$, $R^6$, $R^7$, $R^9$, m, and halo are as defined above.

A compound of Formula I(a), I(b), II(a), II(b), I(a), III(b), IV(a), IV(b), V(a), V(b), VI(a), VI(h), VI(a), VII(b), VII(a), VIII(b), IX(a), IX(b), X, or XI, or a pharmaceutically acceptable salt or solvate thereof (each being a "Proline Analog Compound") is a cannabinoid receptor ligand useful for the treatment or prevention of a Condition in an animal, said condition defined below, and being treatable by modulation of an activity of a cannabinoid receptor.

In certain embodiments, the Proline Analog Compounds of the present invention are modulators of cannabinoid receptor function. In one aspect of this embodiment, a Proline Analog Compound of the present invention is a modulator of both CB1 receptor function and CB2 receptor function. In another aspect of this embodiment, a Proline Analog Compound of the present invention is a selective modulator of CB1 receptor function. In a further aspect of this embodiment, a Proline Analog Compound of the present invention is a selective modulator of CB2 receptor function. In another embodiment, a Proline Analog Compound is an agonist of a human CB1 receptor and a human CB2 receptor. In a further embodiment, a Proline Analog Compound is an antagonist or inverse agonist of a human CB1 receptor and a human CB2 receptor.

In still another embodiment, a Proline Analog Compound is an agonist of a human CB1 receptor. In a further embodiment, a Proline Analog Compound is an antagonist or inverse agonist of a human CB1 receptor.

In a still further embodiment, a Proline Analog Compound is an agonist of a human CB2 receptor. In a further embodiment, a Proline Analog Compound is an antagonist or inverse agonist of a human CB2 receptor.

The invention relates to compositions comprising a Proline Analog Compound, particularly an effective amount of a Proline Analog Compound, and a pharmaceutically acceptable carrier or excipient. The present compositions are useful for treating or preventing a Condition in an animal.

The present invention also encompasses a method of treating a Condition in an animal, comprising administering to an animal in need thereof, an effective amount of a Proline Analog Compound that is a modulator of one or more cannabinoid receptor functions.

The invention further relates to methods for preventing a Condition in an animal, comprising administering to an animal in need thereof an effective amount of a Proline Analog Compound.

The invention further relates to kits comprising a container containing an effective amount of a Proline Analog Compound and instructions for using it to treat or prevent a Condition in an animal.

The invention further relates to methods for modulating cannabinoid-receptor function in a cell, comprising contacting a cell capable of expressing a cannabinoid receptor with a Proline Analog Compound.

The invention further relates to methods for stimulating cannabinoid-receptor function in a cell, comprising contacting a cell expressing a cannabinoid receptor with a Proline Analog Compound capable of stimulating said cannabinoid receptor function.

The invention further relates to methods for inhibiting cannabinoid-receptor function in a cell, comprising contacting a cell expressing a cannabinoid receptor with a Proline Analog Compound capable of inhibiting said cannabinoid receptor function.

The invention further relates to use of a Proline Analog Compound for manufacturing a medicament useful for treating a Condition in an animal.

The invention further relates to methods for preparing a pharmaceutical composition, comprising the step of admixing a Proline Analog Compound and a pharmaceutically-acceptable carrier or excipient.

The present invention may be understood more fully by reference to the following detailed description and illustrative examples, which are intended to exemplify non-limiting embodiments of the invention.

5. DETAILED DESCRIPTION OF THE INVENTION

5.1 Definitions

As used herein, the following terms have the indicated meaning:

"—$C_1$-$C_3$ alkyl" means a straight or branched, non-cyclic, hydrocarbon chain having from 1 to 3 carbon atoms. Representative straight chain and branched chain —$C_1$-$C_3$ alkyls include -methyl, -ethyl, -n-propyl and isopropyl.

"—$C_1$-$C_4$ alkyl" means a straight or branched, non-cyclic, hydrocarbon chain having from 1 to 4 carbon atoms. Representative straight chain —$C_1$-$C_4$ alkyls include methyl, -ethyl, -n-propyl, and -n-butyl. Representative branched chain —$C_1$-$C_4$ alkyls include -isopropyl, -sec-butyl, -isobutyl, and -tert-butyl.

"Lower alkyl," as used herein, means a straight or branched, non-cyclic, hydrocarbon chain having from 1 to 5 carbon atoms. Representative lower alkyl groups include methyl, ethyl, -n-propyl, -n-butyl, and -n-pentyl, -isopropyl, -sec-butyl, -isobutyl, -tert-butyl, -2-methylbutyl, and -2,2-dimethylpropyl.

"—$C_1$-$C_6$ alkyl" means a straight or branched, non-cyclic, hydrocarbon chain having from 1 to 6 carbon atoms. Representative straight chain —$C_1$-$C_6$ alkyls include methyl, -ethyl, -n-propyl, -n-butyl, -n-pentyl and -n-hexyl. Representative branched chain —$C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl and 3,3-dimethylbutyl.

"—($C_1$-$C_{10}$)alkyl" means a straight chain or branched, non-cyclic, hydrocarbon having from 1 to 10 carbon atoms. Representative straight chain —($C_1$-$C_{10}$) alkyls include methyl, -ethyl, -n-propyl, -n-butyl, -n-pentyl, -n-hexyl, -n-heptyl, -n-octyl, -n-nonyl, and -n-decyl. Representative branched —($C_1$-$C_{10}$) alkyls include isopropyl, sec-butyl, isobutyl, -tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$C_3$-$C_8$ cycloalkyl" means a saturated cyclic hydrocarbon having from 3 to 8 carbon atoms. Representative —$C_3$-$C_8$ cycloalkyls are -cyclopropyl, -cyclobutyl, -cyclopentyl, -cyclohexyl, -cycloheptyl and -cyclooctyl.

"-(5- to 7-membered)heteroaryl" means a monocyclic aromatic heterocycle ring of 5 to 7 members, wherein at least one carbon atom of the ring is replaced with a heteroatom independently selected from nitrogen, oxygen, and sulfur. The -(5- to 7-membered)heteroaryl's ring contains at least one carbon atom. Representative -(5- to 7-membered)heteroaryls include pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, thiadiazolyl, triazinyl, a tetrazolyl.

"$CH_2$ (halo)" means a methyl group wherein one of the hydrogens of the methyl group has been replaced with a halogen. Representative —$CH_2$(halo) groups include —CHF, —$CH_2$Cl, —$CH_2$Br, and —$CH_2$I.

"CH(halo)$_2$" means a methyl group wherein two of the hydrogens of the methyl group has been replaced with a halogen. Representative —CH(halo)$_2$ groups include —$CHF_2$, —$CHCl_2$, —$CHBr_2$, and —$CHI_2$.

"C(halo)$_3$" means a methyl group wherein each of the hydrogens of the methyl group has been replaced with a halogen. Representative —C(halo)$_3$ groups include —$CF_3$, —$CCl_3$, —$CBr_3$, and —$CI_3$.

"-Halogen" or "halo" means —F, —Cl, —Br, or —I.

The term "animal," includes, but is not limited to, a cow, ape, monkey, chimpanzee, baboon, horse, sheep, pig, chicken, turkey, quail, cat, dog, mouse, rat, rabbit, guinea pig and human.

The term "solvate" means a compound formed by salvation, i.e. the combination of solvent molecules with molecules or ions of a solute. In specific embodiments, a solvate of a Proline Analog compound of the invention a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. In a specific embodiment, the solvate is a hydrate.

The term "stereoisomers" is a general term for all isomers of individual molecules that differ only in the orientation of their atoms in space. It includes enantiomers and isomers of compounds with more than one chiral center that are not mirror images of one another (diastereomers). Some Proline Analog compounds disclosed herein can contain one or more asymmetric centers and can thus give rise to enantiomers, diastereomers, and other stereoisomeric forms. The present invention is meant to encompass all such possible forms as well as the racemic and resolved forms and mixtures thereof. When the Proline Analog compounds described herein contain olefinic double bonds or other centers of geometric asymmetry, and unless specified otherwise, it is intended to include both E and Z geometric isomers. All tautomers are intended to be encompassed by the present invention as well. Thus, all stereoisomers (including but not limited to geometric isomers, optical isomers and the like) of the Proline Analog compounds of the invention (including those of the salts, solvates of the Proline Analog compounds, such as those which may exist due to asymmetric carbons on various substituents, including enantiomeric forms (which may exist even in the absence of asymmetric carbons), rotameric forms, atropisomers, and diastereomeric forms, are contemplated to be within the scope of this invention.

The phrase "pharmaceutically acceptable salt," as used herein, includes a salt formed from an acid and the basic nitrogen group of a Proline Analog Compound. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt of a Proline Analog Compound having an acidic functional group, such as a carboxylic acid functional group, and a pharmaceutically acceptable inorganic or organic base. Illustrative bases include, but are not limited to, hydroxides of alkali metals such as sodium, potassium and lithium; hydroxides of alkaline earth metal such as calcium and magnesium; hydroxides of other metals, such as aluminum and zinc; ammonia; and organic amines, such as unsubstituted or hydroxy substituted mono-, di-, or trialkylamines; dicyclohexylamine, tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N, N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

The terms "treat," "treatment of" and "treating" a Condition include the lessening of the severity, the cessation, or the reversal of the symptoms of the Condition. In one illustrative embodiment, "treat," "treating" or "treatment of" includes decreasing the overall frequency of episodes of pain.

The terms "prevent," "prevention of" and "preventing" of a Condition include the avoidance of the onset of that Condition.

The terms "a" and "an" refer to one or more.

The phrase "cannabinoid receptor" means a $CB_1$ receptor, or a $CB_2$ receptor.

The phrase "effective amount" when used in connection with a Proline Analog Compound means an amount of the Proline Analog Compound that is useful for treating or preventing a Condition in an animal, or that can modulate, stimulate, or inhibit a cannabinoid receptor function in a cell.

The phrase "effective amount" when used in connection with another therapeutic agent means an amount for providing the therapeutic effect of that therapeutic agent when administered to an animal.

The phrase "modulator of a cannabinoid receptor" refers to a compound, e.g. a Proline Analog Compound, that activates or inhibits a cannabinoid receptor. A Proline Analog Compound, which is a ligand of a cannabinoid receptor, can modulate the activity of the cannabiniod receptor by acting as an agonist, partial agonist, inverse agonist, antagonist, or partial antagonist of that cannabinoid receptor.

The phrase "cannabinoid receptor agonist," as used hereinafter, is meant to include compounds acting as full agonists or partial agonists.

The phrase "cannabinoid receptor antagonist," as used hereinafter, is meant to include compounds acting as full antagonists, partial antagonists, or as inverse agonists of a cannabinoid receptor.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonst". (See Ross and Kenaidn, *Pharmacodynamics: Mechanisms of Drug Action and the Relationship Between Drug Concentration and Effect*, Chapter 2 in Goodman & Gilman's *The Pharmacological Basis of Therapeutics* 31-32 (J. G. Hardman, L. E. Limbird and A. Goodman-Gilman eds., 10th ed 2001). The phrase "inverse agonist" as used hereinafter, is meant to include compounds that bind to the receptor and stabilize the receptor in its inactive conformation. When a first group is "substituted with one or more" second groups, each of one or more of the first group's hydrogen atoms is replaced with a second group.

In one embodiment, a first group is substituted with up to three independently selected second groups.

In another embodiment, a first group is substituted with one or two independently selected second groups.

In another embodiment, a first group is substituted with only one second group.

5.2 The Proline Analog Compounds

Illustrative Proline Analog Compounds of Formula I(a) include compounds of structure (a) and compounds of structure (b), below, as well as pharmaceutically-acceptable salts and solvates thereof:

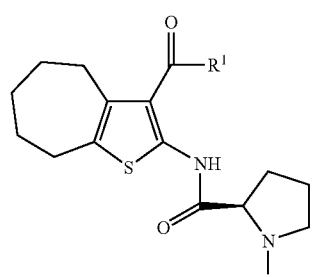

(a)

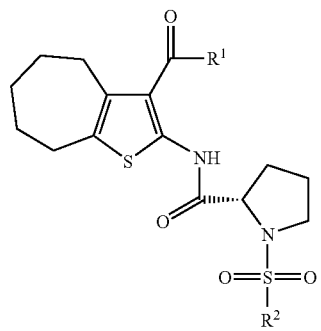

(b)

wherein $R^1$ and $R^2$ are as follows:

TABLE 1

| Compound No.: | $R^1$ | $R^2$ |
|---|---|---|
| AAA ((a) and (b)) | piperidin-1-yl | phenyl |
| AAB ((a) and (b)) | piperidin-1-yl | 4-fluorophenyl |
| AAC ((a) and (b)) | piperidin-1-yl | 4-methylphenyl |
| AAD ((a) and (b)) | piperidin-1-yl | methyl |
| AAE ((a) and (b)) | piperidin-1-yl | furan-2-yl |
| AAF ((a) and (b)) | piperidin-1-yl | thiophen-2-yl |
| AAG ((a) and (b)) | piperazin-1-yl | phenyl |
| AAH ((a) and (b)) | piperazin-1-yl | 4-fluorophenyl |
| AAI ((a) and (b)) | piperazin-1-yl | 4-methylphenyl |
| AAJ ((a) and (b)) | piperazin-1-yl | methyl |
| AAK ((a) and (b)) | piperazin-1-yl | furan-2-yl |
| AAL ((a) and (b)) | piperazin-1-yl | thiophen-2-yl |
| AAM ((a) and (b)) | morpholin-4-yl | phenyl |
| AAN ((a) and (b)) | morpholin-4-yl | 4-fluorophenyl |
| AAO ((a) and (b)) | morpholin-4-yl | 4-methylphenyl |

TABLE 1-continued

| Compound No.: | R¹ | R² |
|---|---|---|
| AAP ((a) and (b)) | N-morpholine | —CH₃ |
| AAQ ((a) and (b)) | N-morpholine | furan-2-yl |
| AAR ((a) and (b)) | N-morpholine | thien-2-yl |
| AAS ((a) and (b)) | N-pyrrole | phenyl |
| AAT ((a) and (b)) | N-pyrrole | 4-F-phenyl |
| AAU ((a) and (b)) | N-pyrrole | 4-CH₃-phenyl |
| AAV ((a) and (b)) | N-pyrrole | —CH₃ |
| AAW ((a) and (b)) | N-pyrrole | furan-2-yl |
| AAX ((a) and (b)) | N-pyrrole | thien-2-yl |
| AAY ((a) and (b)) | N-imidazole | phenyl |
| AAZ ((a) and (b)) | N-imidazole | 4-F-phenyl |
| ABA ((a) and (b)) | N-imidazole | 4-CH₃-phenyl |
| ABB ((a) and (b)) | N-imidazole | —CH₃ |
| ABC ((a) and (b)) | N-imidazole | furan-2-yl |

TABLE 1-continued

| Compound No.: | R¹ | R² |
|---|---|---|
| ABD ((a) and (b)) | N-imidazole | thien-2-yl |
| ABE ((a) and (b)) | —OCH₂CH₃ | phenyl |
| ABF ((a) and (b)) | —OCH₂CH₃ | 4-F-phenyl |
| ABG ((a) and (b)) | —OCH₂CH₃ | 4-CH₃-phenyl |
| ABH ((a) and (b)) | —OCH₂CH₃ | —CH₃ |
| ABI ((a) and (b)) | —OCH₂CH₃ | furan-2-yl |
| ABJ ((a) and (b)) | —OCH₂CH₃ | thien-2-yl |

Additional, illustrative Proline Analog Compounds of Formula I(b) include compounds of structure (a) and compounds of structure (b), below, as well as pharmaceutically-acceptable salts and solvates thereof:

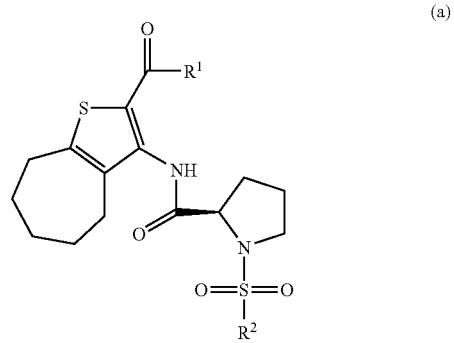

(a)

-continued

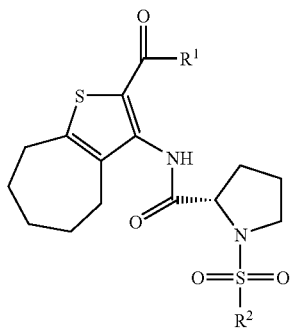

wherein R¹ and R² are as follows:

TABLE 2

| Compound No.: | R¹ | R² |
|---|---|---|
| BAA ((a) and (b)) | piperidin-1-yl | phenyl |
| BAB ((a) and (b)) | piperidin-1-yl | 4-fluorophenyl |
| BAC ((a) and (b)) | piperidin-1-yl | 4-methylphenyl |
| BAD ((a) and (b)) | piperidin-1-yl | CH₃ |
| BAE ((a) and (b)) | piperidin-1-yl | furan-2-yl |
| BAF ((a) and (b)) | piperidin-1-yl | thiophen-2-yl |
| BAG ((a) and (b)) | piperazin-1-yl | phenyl |
| BAH ((a) and (b)) | piperazin-1-yl | 4-fluorophenyl |
| BAI ((a) and (b)) | piperazin-1-yl | 4-methylphenyl |
| BAJ ((a) and (b)) | piperazin-1-yl | CH₃ |

TABLE 2-continued

| Compound No.: | R¹ | R² |
|---|---|---|
| BAK ((a) and (b)) | piperazin-1-yl | furan-2-yl |
| BAL ((a) and (b)) | piperazin-1-yl | thiophen-2-yl |
| BAM ((a) and (b)) | morpholin-4-yl | phenyl |
| BAN ((a) and (b)) | morpholin-4-yl | 4-fluorophenyl |
| BAO ((a) and (b)) | morpholin-4-yl | 4-methylphenyl |
| BAP ((a) and (b)) | morpholin-4-yl | CH₃ |
| BAQ ((a) and (b)) | morpholin-4-yl | furan-2-yl |
| BAR ((a) and (b)) | morpholin-4-yl | thiophen-2-yl |
| BAS ((a) and (b)) | pyrrol-1-yl | phenyl |
| BAT ((a) and (b)) | pyrrol-1-yl | 4-fluorophenyl |
| BAU ((a) and (b)) | pyrrol-1-yl | 4-methylphenyl |
| BAV ((a) and (b)) | pyrrol-1-yl | CH₃ |
| BAW ((a) and (b)) | pyrrol-1-yl | furan-2-yl |
| BAX ((a) and (b)) | pyrrol-1-yl | thiophen-2-yl |

TABLE 2-continued

| Compound No.: | R¹ | R² |
|---|---|---|
| BAY ((a) and (b)) | imidazol-1-yl | phenyl |
| BAZ ((a) and (b)) | imidazol-1-yl | 4-fluorophenyl |
| BBA ((a) and (b)) | imidazol-1-yl | 4-methylphenyl |
| BBB ((a) and (b)) | imidazol-1-yl | —CH₃ |
| BBC ((a) and (b)) | imidazol-1-yl | furan-2-yl |
| BBD ((a) and (b)) | imidazol-1-yl | thiophen-2-yl |
| BBE ((a) and (b)) | —OCH₂CH₃ | phenyl |
| BBF ((a) and (b)) | —OCH₂CH₃ | 4-fluorophenyl |
| BBG ((a) and (b)) | —OCH₂CH₃ | 4-methylphenyl |
| BBH ((a) and (b)) | —OCH₂CH₃ | —CH₃ |
| BBI ((a) and (b)) | —OCH₂CH₃ | furan-2-yl |
| BBJ ((a) and (b)) | —OCH₂CH₃ | thiophen-2-yl |

Illustrative Proline Analog Compounds of Formula II(a) include compounds of structure (a) and compounds of structure (b), below, as well as pharmaceutically-acceptable salts and solvates thereof:

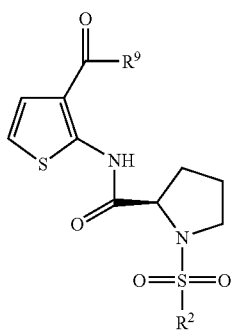

(a)

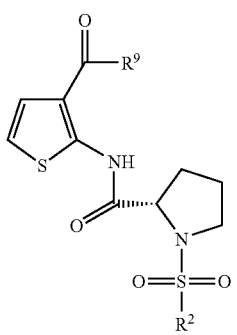

(b)

wherein R⁹ and R² are as follows:

TABLE 3

| Compound No.: | R⁹ | R² |
|---|---|---|
| CAA ((a) and (b)) | piperidin-1-yl | phenyl |
| CAB ((a) and (b)) | piperidin-1-yl | 4-fluorophenyl |
| CAC ((a) and (b)) | piperidin-1-yl | 4-methylphenyl |
| CAD ((a) and (b)) | piperidin-1-yl | —CH₃ |
| CAE ((a) and (b)) | piperidin-1-yl | furan-2-yl |
| CAF ((a) and (b)) | piperidin-1-yl | thiophen-2-yl |
| CAG ((a) and (b)) | piperazin-1-yl (NH) | phenyl |

TABLE 3-continued

| Compound No.: | R⁹ | R² |
|---|---|---|
| CAH ((a) and (b)) | piperazine (NH) | 4-F-phenyl |
| CAI ((a) and (b)) | piperazine (NH) | 4-CH₃-phenyl |
| CAJ ((a) and (b)) | piperazine (NH) | CH₃ |
| CAK ((a) and (b)) | piperazine (NH) | 2-furyl |
| CAL ((a) and (b)) | piperazine (NH) | 2-thienyl |
| CAM ((a) and (b)) | morpholine | phenyl |
| CAN ((a) and (b)) | morpholine | 4-F-phenyl |
| CAO ((a) and (b)) | morpholine | 4-CH₃-phenyl |
| CAP ((a) and (b)) | morpholine | CH₃ |
| CAQ ((a) and (b)) | morpholine | 2-furyl |
| CAR ((a) and (b)) | morpholine | 2-thienyl |
| CAS ((a) and (b)) | pyrrolyl | phenyl |
| CAT ((a) and (b)) | pyrrolyl | 4-F-phenyl |
| CAU ((a) and (b)) | pyrrolyl | 4-CH₃-phenyl |
| CAV ((a) and (b)) | pyrrolyl | CH₃ |
| CAW ((a) and (b)) | pyrrolyl | 2-furyl |
| CAX ((a) and (b)) | pyrrolyl | 2-thienyl |
| CAY ((a) and (b)) | imidazolyl | phenyl |
| CAZ ((a) and (b)) | imidazolyl | 4-F-phenyl |
| CBA ((a) and (b)) | imidazolyl | 4-CH₃-phenyl |
| CBB ((a) and (b)) | imidazolyl | CH₃ |
| CBC ((a) and (b)) | imidazolyl | 2-furyl |
| CBD ((a) and (b)) | imidazolyl | 2-thienyl |

Additional, illustrative Proline Analog Compounds of Formula II(b) include compounds of structure (a) and compounds of structure (b), below, as well as pharmaceutically-acceptable salts and solvates thereof:

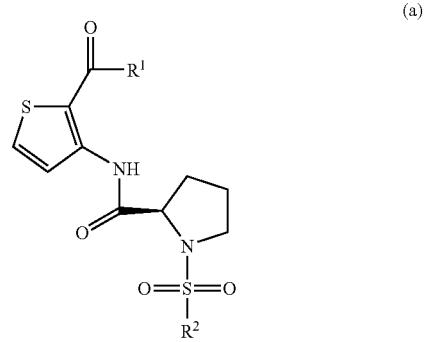

(a)

-continued

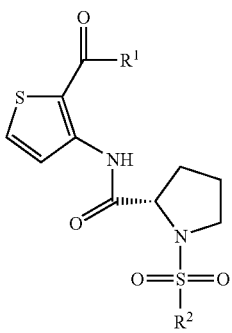
(b)

wherein R¹ and R² are as follows:

TABLE 4

| Compound No.: | R¹ | R² |
|---|---|---|
| DAA ((a) and (b)) | piperidin-1-yl | phenyl |
| DAB ((a) and (b)) | piperidin-1-yl | 4-fluorophenyl |
| DAC ((a) and (b)) | piperidin-1-yl | 4-methylphenyl |
| DAD ((a) and (b)) | piperidin-1-yl | CH₃ |
| DAE ((a) and (b)) | piperidin-1-yl | furan-2-yl |
| DAF ((a) and (b)) | piperidin-1-yl | thiophen-2-yl |
| DAG ((a) and (b)) | piperazin-1-yl | phenyl |
| DAH ((a) and (b)) | piperazin-1-yl | 4-fluorophenyl |
| DAI ((a) and (b)) | piperazin-1-yl | 4-methylphenyl |
| DAJ ((a) and (b)) | piperazin-1-yl | CH₃ |
| DAK ((a) and (b)) | piperazin-1-yl | furan-2-yl |
| DAL ((a) and (b)) | piperazin-1-yl | thiophen-2-yl |
| DAM ((a) and (b)) | morpholin-4-yl | phenyl |
| DAN ((a) and (b)) | morpholin-4-yl | 4-fluorophenyl |
| DAO ((a) and (b)) | morpholin-4-yl | 4-methylphenyl |
| DAP ((a) and (b)) | morpholin-4-yl | CH₃ |
| DAQ ((a) and (b)) | morpholin-4-yl | furan-2-yl |
| DAR ((a) and (b)) | morpholin-4-yl | thiophen-2-yl |
| DAS ((a) and (b)) | pyrrol-1-yl | phenyl |
| DAT ((a) and (b)) | pyrrol-1-yl | 4-fluorophenyl |
| DAU ((a) and (b)) | pyrrol-1-yl | 4-methylphenyl |
| DAV ((a) and (b)) | pyrrol-1-yl | CH₃ |
| DAW ((a) and (b)) | pyrrol-1-yl | furan-2-yl |
| DAX ((a) and (b)) | pyrrol-1-yl | thiophen-2-yl |

TABLE 4-continued

| Compound No.: | R¹ | R² |
|---|---|---|
| DAY ((a) and (b)) | imidazol-1-yl | phenyl |
| DAZ ((a) and (b)) | imidazol-1-yl | 4-fluorophenyl |
| DBA ((a) and (b)) | imidazol-1-yl | 4-methylphenyl |
| DBB ((a) and (b)) | imidazol-1-yl | —CH₃ |
| DBC ((a) and (b)) | imidazol-1-yl | furan-2-yl |
| DBD ((a) and (b)) | imidazol-1-yl | thiophen-2-yl |
| DBE ((a) and (b)) | —OCH₂CH₃ | phenyl |
| DBF ((a) and (b)) | —OCH₂CH₃ | 4-fluorophenyl |
| DBG ((a) and (b)) | —OCH₂CH₃ | 4-methylphenyl |
| DBH ((a) and (b)) | —OCH₂CH₃ | —CH₃ |
| DBI ((a) and (b)) | —OCH₂CH₃ | furan-2-yl |
| DBJ ((a) and (b)) | —OCH₂CH₃ | thiophen-2-yl |

Illustrative Proline Analog Compounds of Formula III(a) include compounds of structure (a) and compounds of structure (b), below, as well as pharmaceutically-acceptable salts and solvates thereof:

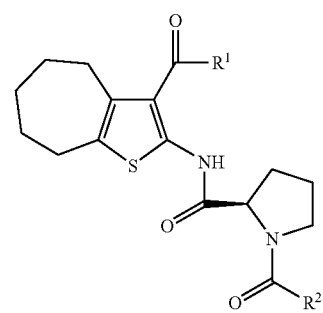
(a)

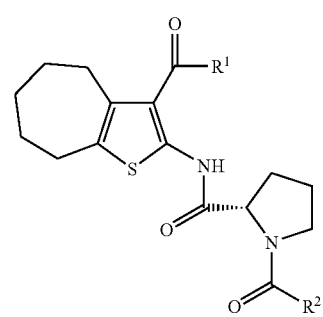
(b)

wherein R¹ and R² are as follows:

TABLE 5

| Compound No.: | R¹ | R² |
|---|---|---|
| EAA ((a) and (b)) | piperidin-1-yl | phenyl |
| EAB ((a) and (b)) | piperidin-1-yl | 4-fluorophenyl |
| EAC ((a) and (b)) | piperidin-1-yl | 4-methylphenyl |
| EAD ((a) and (b)) | piperidin-1-yl | —CH₃ |
| EAE ((a) and (b)) | piperidin-1-yl | furan-2-yl |
| EAF ((a) and (b)) | piperidin-1-yl | thiophen-2-yl |
| EAG ((a) and (b)) | piperazin-1-yl | phenyl |

TABLE 5-continued

| Compound No.: | R¹ | R² |
|---|---|---|
| EAH ((a) and (b)) | piperazine (N-NH) | 4-F-phenyl |
| EAI ((a) and (b)) | piperazine (N-NH) | 4-CH₃-phenyl |
| EAJ ((a) and (b)) | piperazine (N-NH) | CH₃ |
| EAK ((a) and (b)) | piperazine (N-NH) | 2-furyl |
| EAL ((a) and (b)) | piperazine (N-NH) | 2-thienyl |
| EAM ((a) and (b)) | morpholine (N-O) | phenyl |
| EAN ((a) and (b)) | morpholine (N-O) | 4-F-phenyl |
| EAO ((a) and (b)) | morpholine (N-O) | 4-CH₃-phenyl |
| EAP ((a) and (b)) | morpholine (N-O) | CH₃ |
| EAQ ((a) and (b)) | morpholine (N-O) | 2-furyl |
| EAR ((a) and (b)) | morpholine (N-O) | 2-thienyl |
| EAS ((a) and (b)) | pyrrolyl | phenyl |
| EAT ((a) and (b)) | pyrrolyl | 4-F-phenyl |
| EAU ((a) and (b)) | pyrrolyl | 4-CH₃-phenyl |
| EAV ((a) and (b)) | pyrrolyl | CH₃ |
| EAW ((a) and (b)) | pyrrolyl | 2-furyl |
| EAX ((a) and (b)) | pyrrolyl | 2-thienyl |
| EAY ((a) and (b)) | imidazolyl | phenyl |
| EAZ ((a) and (b)) | imidazolyl | 4-F-phenyl |
| EBA ((a) and (b)) | imidazolyl | 4-CH₃-phenyl |
| EBB ((a) and (b)) | imidazolyl | CH₃ |
| EBC ((a) and (b)) | imidazolyl | 2-furyl |
| EBD ((a) and (b)) | imidazolyl | 2-thienyl |
| EBE ((a) and (b)) | —OCH₂CH₃ | phenyl |
| EBF ((a) and (b)) | —OCH₂CH₃ | 4-F-phenyl |
| EBG ((a) and (b)) | —OCH₂CH₃ | 4-CH₃-phenyl |
| EBH ((a) and (b)) | —OCH₂CH₃ | CH₃ |
| EBI ((a) and (b)) | —OCH₂CH₃ | 2-furyl |

TABLE 5-continued

| Compound No.: | R¹ | R² |
|---|---|---|
| EBJ ((a) and (b)) | -OCH₂CH₃ | 2-thienyl |

Illustrative Proline Analog Compounds of Formula III(b) include compounds of structure (a) and compounds of structure (b), below, as well as pharmaceutically-acceptable salts and solvates thereof:

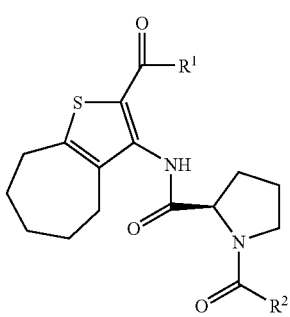
(a)

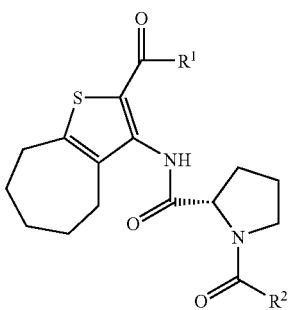
(b)

wherein R¹ and R² are as follows:

TABLE 6

| Compound No.: | R¹ | R² |
|---|---|---|
| FAA ((a) and (b)) | piperidin-1-yl | phenyl |
| FAB ((a) and (b)) | piperidin-1-yl | 4-fluorophenyl |
| FAC ((a) and (b)) | piperidin-1-yl | 4-methylphenyl |
| FAD ((a) and (b)) | piperidin-1-yl | -CH₃ |
| FAE ((a) and (b)) | piperidin-1-yl | 2-furyl |
| FAF ((a) and (b)) | piperidin-1-yl | 2-thienyl |
| FAG ((a) and (b)) | piperazin-1-yl | phenyl |
| FAH ((a) and (b)) | piperazin-1-yl | 4-fluorophenyl |
| FAI ((a) and (b)) | piperazin-1-yl | 4-methylphenyl |
| FAJ ((a) and (b)) | piperazin-1-yl | -CH₃ |
| FAK ((a) and (b)) | piperazin-1-yl | 2-furyl |
| FAL ((a) and (b)) | piperazin-1-yl | 2-thienyl |
| FAM ((a) and (b)) | morpholin-4-yl | phenyl |
| FAN ((a) and (b)) | morpholin-4-yl | 4-fluorophenyl |
| FAO ((a) and (b)) | morpholin-4-yl | 4-methylphenyl |
| FAP ((a) and (b)) | morpholin-4-yl | -CH₃ |
| FAQ ((a) and (b)) | morpholin-4-yl | 2-furyl |
| FAR ((a) and (b)) | morpholin-4-yl | 2-thienyl |

TABLE 6-continued

| Compound No.: | R¹ | R² |
|---|---|---|
| FAS ((a) and (b)) | N-pyrrolyl | phenyl |
| FAT ((a) and (b)) | N-pyrrolyl | 4-F-phenyl |
| FAU ((a) and (b)) | N-pyrrolyl | 4-CH₃-phenyl |
| FAV ((a) and (b)) | N-pyrrolyl | —CH₃ |
| FAW ((a) and (b)) | N-pyrrolyl | 2-furyl |
| FAX ((a) and (b)) | N-pyrrolyl | 2-thienyl |
| FAY ((a) and (b)) | N-imidazolyl | phenyl |
| FAZ ((a) and (b)) | N-imidazolyl | 4-F-phenyl |
| FBA ((a) and (b)) | N-imidazolyl | 4-CH₃-phenyl |
| FBB ((a) and (b)) | N-imidazolyl | —CH₃ |
| FBC ((a) and (b)) | N-imidazolyl | 2-furyl |
| FBD ((a) and (b)) | N-imidazolyl | 2-thienyl |
| FBE ((a) and (b)) | —OCH₂CH₃ | phenyl |
| FBF ((a) and (b)) | —OCH₂CH₃ | 4-F-phenyl |
| FBG ((a) and (b)) | —OCH₂CH₃ | 4-CH₃-phenyl |
| FBH ((a) and (b)) | —OCH₂CH₃ | —CH₃ |
| FBI ((a) and (b)) | —OCH₂CH₃ | 2-furyl |
| FBJ ((a) and (b)) | —OCH₂CH₃ | 2-thienyl |

Additional, illustrative Proline Analog Compounds of Formula X include compounds of structure (a) and compounds of structure (b), below, as well as pharmaceutically-acceptable salts and solvates thereof:

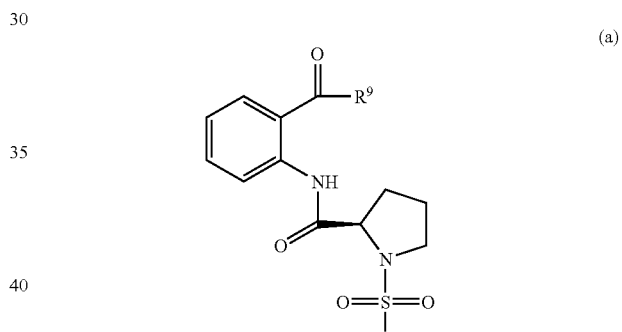

(a)

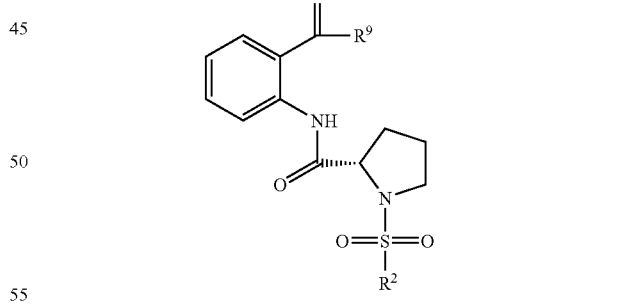

(b)

wherein R⁹ and R² are as follows:

TABLE 7

| Compound No.: | R⁹ | R² |
|---|---|---|
| GAA ((a) and (b)) | N-piperidinyl | phenyl |

TABLE 7-continued

| Compound No.: | R⁹ | R² |
|---|---|---|
| GAB ((a) and (b)) | piperidin-1-yl | 4-fluorophenyl |
| GAC ((a) and (b)) | piperidin-1-yl | 4-methylphenyl |
| GAD ((a) and (b)) | piperidin-1-yl | CH₃ |
| GAE ((a) and (b)) | piperidin-1-yl | furan-2-yl |
| GAF ((a) and (b)) | piperidin-1-yl | thiophen-2-yl |
| GAG ((a) and (b)) | piperazin-1-yl | phenyl |
| GAH ((a) and (b)) | piperazin-1-yl | 4-fluorophenyl |
| GAI ((a) and (b)) | piperazin-1-yl | 4-methylphenyl |
| GAJ ((a) and (b)) | piperazin-1-yl | CH₃ |
| GAK ((a) and (b)) | piperazin-1-yl | furan-2-yl |
| GAL ((a) and (b)) | piperazin-1-yl | thiophen-2-yl |
| GAM ((a) and (b)) | morpholin-4-yl | phenyl |
| GAN ((a) and (b)) | morpholin-4-yl | 4-fluorophenyl |
| GAO ((a) and (b)) | morpholin-4-yl | 4-methylphenyl |
| GAP ((a) and (b)) | morpholin-4-yl | CH₃ |
| GAQ ((a) and (b)) | morpholin-4-yl | furan-2-yl |
| GAR ((a) and (b)) | morpholin-4-yl | thiophen-2-yl |
| GAS ((a) and (b)) | pyrrol-1-yl | phenyl |
| GAT ((a) and (b)) | pyrrol-1-yl | 4-fluorophenyl |
| GAU ((a) and (b)) | pyrrol-1-yl | 4-methylphenyl |
| GAV ((a) and (b)) | pyrrol-1-yl | CH₃ |
| GAW ((a) and (b)) | pyrrol-1-yl | furan-2-yl |
| GAX ((a) and (b)) | pyrrol-1-yl | thiophen-2-yl |
| GAY ((a) and (b)) | imidazol-1-yl | phenyl |
| GAZ ((a) and (b)) | imidazol-1-yl | 4-fluorophenyl |
| GBA ((a) and (b)) | imidazol-1-yl | 4-methylphenyl |
| GBB ((a) and (b)) | imidazol-1-yl | CH₃ |
| GBC ((a) and (b)) | imidazol-1-yl | furan-2-yl |

TABLE 7-continued

| Compound No.: | R⁹ | R² |
|---|---|---|
| GBD ((a) and (b)) | imidazol-1-yl | thiophen-2-yl |
| GBE ((a) and (b)) | —OCH₂CH₃ | thiophen-2-yl |

Additional, illustrative Proline Analog Compounds of Formula I(a) include compounds of structure (a) and compounds of structure (b), below, as well as pharmaceutically-acceptable salts and solvates thereof:

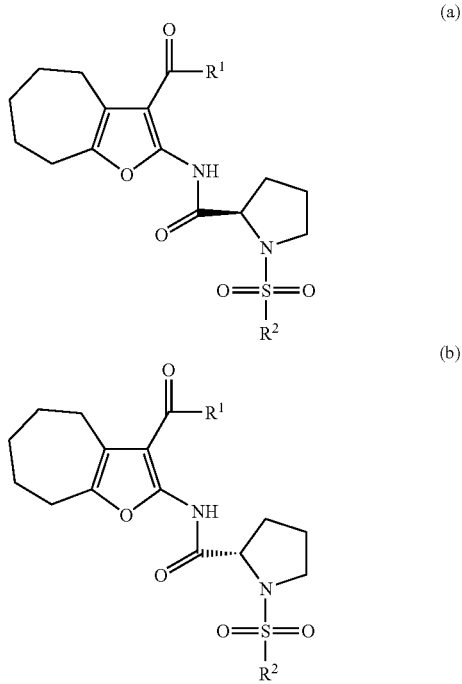

wherein $R^1$ and $R^2$ are as follows:

TABLE 8

| Compound No.: | R¹ | R² |
|---|---|---|
| HAA ((a) and (b)) | piperidin-1-yl | phenyl |
| HAB ((a) and (b)) | piperidin-1-yl | 4-F-phenyl |
| HAC ((a) and (b)) | piperidin-1-yl | 4-CH₃-phenyl |
| HAD ((a) and (b)) | piperidin-1-yl | CH₃ |
| HAE ((a) and (b)) | piperidin-1-yl | furan-2-yl |
| HAF ((a) and (b)) | piperidin-1-yl | thiophen-2-yl |
| HAG ((a) and (b)) | piperazin-1-yl | phenyl |
| HAH ((a) and (b)) | piperazin-1-yl | 4-F-phenyl |
| HAI ((a) and (b)) | piperazin-1-yl | 4-CH₃-phenyl |
| HAJ ((a) and (b)) | piperazin-1-yl | CH₃ |
| HAK ((a) and (b)) | piperazin-1-yl | furan-2-yl |
| HAL ((a) and (b)) | piperazin-1-yl | thiophen-2-yl |
| HAM ((a) and (b)) | morpholin-4-yl | phenyl |
| HAN ((a) and (b)) | morpholin-4-yl | 4-F-phenyl |
| HAO ((a) and (b)) | morpholin-4-yl | 4-CH₃-phenyl |
| HAP ((a) and (b)) | morpholin-4-yl | CH₃ |
| HAQ ((a) and (b)) | morpholin-4-yl | furan-2-yl |

TABLE 8-continued

| Compound No.: | R¹ | R² |
|---|---|---|
| HAR ((a) and (b)) | morpholinyl (N-linked) | 2-thienyl |
| HAS ((a) and (b)) | pyrrol-1-yl | phenyl |
| HAT ((a) and (b)) | pyrrol-1-yl | 4-F-phenyl |
| HAU ((a) and (b)) | pyrrol-1-yl | 4-CH₃-phenyl |
| HAV ((a) and (b)) | pyrrol-1-yl | —CH₃ |
| HAW ((a) and (b)) | pyrrol-1-yl | 2-furyl |
| HAX ((a) and (b)) | pyrrol-1-yl | 2-thienyl |
| HAY ((a) and (b)) | imidazol-1-yl | phenyl |
| HAZ ((a) and (b)) | imidazol-1-yl | 4-F-phenyl |
| HBA ((a) and (b)) | imidazol-1-yl | 4-CH₃-phenyl |
| HBB ((a) and (b)) | imidazol-1-yl | —CH₃ |
| HBC ((a) and (b)) | imidazol-1-yl | 2-furyl |
| HBD ((a) and (b)) | imidazol-1-yl | 2-thienyl |
| HBE ((a) and (b)) | —OCH₂CH₃ | phenyl |
| HBF ((a) and (b)) | —OCH₂CH₃ | 4-F-phenyl |
| HBG ((a) and (b)) | —OCH₂CH₃ | 4-CH₃-phenyl |
| HBH ((a) and (b)) | —OCH₂CH₃ | —CH₃ |
| HBI ((a) and (b)) | —OCH₂CH₃ | 2-furyl |
| HBJ ((a) and (b)) | —OCH₂CH₃ | 2-thienyl |

Illustrative Proline Analog Compounds of Formula I(b) include compounds of structure (a) and compounds of structure (b), below, as well as pharmaceutically-acceptable salts and solvates thereof:

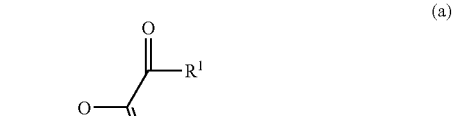

(a)

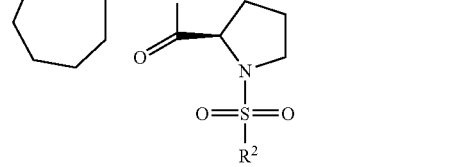

(b)

wherein R¹ and R² are as follows:

TABLE 9

| Compound No.: | R¹ | R² |
|---|---|---|
| IAA ((a) and (b)) | piperidin-1-yl | phenyl |
| IAB ((a) and (b)) | piperidin-1-yl | 4-fluorophenyl |
| IAC ((a) and (b)) | piperidin-1-yl | 4-methylphenyl |
| IAD ((a) and (b)) | piperidin-1-yl | CH₃ |
| IAE ((a) and (b)) | piperidin-1-yl | furan-2-yl |
| IAF ((a) and (b)) | piperidin-1-yl | thiophen-2-yl |
| IAG ((a) and (b)) | piperazin-1-yl | phenyl |
| IAH ((a) and (b)) | piperazin-1-yl | 4-fluorophenyl |
| IAI ((a) and (b)) | piperazin-1-yl | 4-methylphenyl |
| IAJ ((a) and (b)) | piperazin-1-yl | CH₃ |
| IAK ((a) and (b)) | piperazin-1-yl | furan-2-yl |
| IAL ((a) and (b)) | piperazin-1-yl | thiophen-2-yl |
| IAM ((a) and (b)) | morpholin-4-yl | phenyl |
| IAN ((a) and (b)) | morpholin-4-yl | 4-fluorophenyl |

TABLE 9-continued

| Compound No.: | R¹ | R² |
|---|---|---|
| IAO ((a) and (b)) | morpholin-4-yl | 4-methylphenyl |
| IAP ((a) and (b)) | morpholin-4-yl | CH₃ |
| IAQ ((a) and (b)) | morpholin-4-yl | furan-2-yl |
| IAR ((a) and (b)) | morpholin-4-yl | thiophen-2-yl |
| IAS ((a) and (b)) | pyrrol-1-yl | phenyl |
| IAT ((a) and (b)) | pyrrol-1-yl | 4-fluorophenyl |
| IAU ((a) and (b)) | pyrrol-1-yl | 4-methylphenyl |
| IAV ((a) and (b)) | pyrrol-1-yl | CH₃ |
| IAW ((a) and (b)) | pyrrol-1-yl | furan-2-yl |
| IAX ((a) and (b)) | pyrrol-1-yl | thiophen-2-yl |
| IAY ((a) and (b)) | imidazol-1-yl | phenyl |
| IAZ ((a) and (b)) | imidazol-1-yl | 4-fluorophenyl |
| IBA ((a) and (b)) | imidazol-1-yl | 4-methylphenyl |
| IBB ((a) and (b)) | imidazol-1-yl | CH₃ |

TABLE 9-continued

| Compound No.: | R¹ | R² |
|---|---|---|
| IBC ((a) and (b)) | imidazol-1-yl | furan-2-yl |
| IBD ((a) and (b)) | imidazol-1-yl | thiophen-2-yl |
| IBE ((a) and (b)) | —OCH₂CH₃ | phenyl |
| IBF ((a) and (b)) | —OCH₂CH₃ | 4-F-phenyl |
| IBG ((a) and (b)) | —OCH₂CH₃ | 4-CH₃-phenyl |
| IBH ((a) and (b)) | —OCH₂CH₃ | —CH₃ |
| IBI ((a) and (b)) | —OCH₂CH₃ | furan-2-yl |
| IBJ ((a) and (b)) | —OCH₂CH₃ | thiophen-2-yl |

Additional, illustrative Proline Analog Compounds of Formula II(a) include compounds of structure (a) and compounds of structure (b), below, as well as pharmaceutically-acceptable salts and solvates thereof:

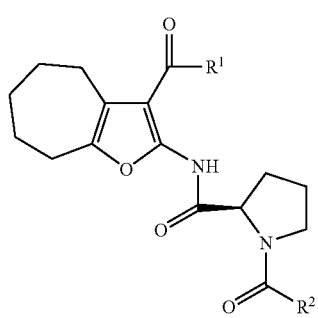

(a)

(b)

wherein R¹ and R² are as follows:

TABLE 10

| Compound No.: | R¹ | R² |
|---|---|---|
| JAA ((a) and (b)) | piperidin-1-yl | phenyl |
| JAB ((a) and (b)) | piperidin-1-yl | 4-F-phenyl |
| JAC ((a) and (b)) | piperidin-1-yl | 4-CH₃-phenyl |
| JAD ((a) and (b)) | piperidin-1-yl | —CH₃ |
| JAE ((a) and (b)) | piperidin-1-yl | furan-2-yl |
| JAF ((a) and (b)) | piperidin-1-yl | thiophen-2-yl |
| JAG ((a) and (b)) | piperazin-1-yl | phenyl |
| JAH ((a) and (b)) | piperazin-1-yl | 4-F-phenyl |
| JAI ((a) and (b)) | piperazin-1-yl | 4-CH₃-phenyl |
| JAJ ((a) and (b)) | piperazin-1-yl | —CH₃ |

TABLE 10-continued

| Compound No.: | R¹ | R² |
|---|---|---|
| JAK ((a) and (b)) | piperazinyl (N-linked, with NH) | 2-furyl |
| JAL ((a) and (b)) | piperazinyl (N-linked, with NH) | 2-thienyl |
| JAM ((a) and (b)) | morpholinyl (N-linked) | phenyl |
| JAN ((a) and (b)) | morpholinyl (N-linked) | 4-fluorophenyl |
| JAO ((a) and (b)) | morpholinyl (N-linked) | 4-methylphenyl |
| JAP ((a) and (b)) | morpholinyl (N-linked) | —CH₃ |
| JAQ ((a) and (b)) | morpholinyl (N-linked) | 2-furyl |
| JAR ((a) and (b)) | morpholinyl (N-linked) | 2-thienyl |
| JAS ((a) and (b)) | pyrrolyl (N-linked) | phenyl |
| JAT ((a) and (b)) | pyrrolyl (N-linked) | 4-fluorophenyl |
| JAU ((a) and (b)) | pyrrolyl (N-linked) | 4-methylphenyl |
| JAV ((a) and (b)) | pyrrolyl (N-linked) | —CH₃ |
| JAW ((a) and (b)) | pyrrolyl (N-linked) | 2-furyl |
| JAX ((a) and (b)) | pyrrolyl (N-linked) | 2-thienyl |
| JAY ((a) and (b)) | imidazolyl (N-linked) | phenyl |
| JAZ ((a) and (b)) | imidazolyl (N-linked) | 4-fluorophenyl |
| JBA ((a) and (b)) | imidazolyl (N-linked) | 4-methylphenyl |
| JBB ((a) and (b)) | imidazolyl (N-linked) | —CH₃ |
| JBC ((a) and (b)) | imidazolyl (N-linked) | 2-furyl |
| JBD ((a) and (b)) | imidazolyl (N-linked) | 2-thienyl |
| JBE ((a) and (b)) | —OCH₂CH₃ | phenyl |
| JBF ((a) and (b)) | —OCH₂CH₃ | 4-fluorophenyl |
| JBG ((a) and (b)) | —OCH₂CH₃ | 4-methylphenyl |
| JBH ((a) and (b)) | —OCH₂CH₃ | —CH₃ |
| JBI ((a) and (b)) | —OCH₂CH₃ | 2-furyl |
| JBJ ((a) and (b)) | —OCH₂CH₃ | 2-thienyl |

Illustrative Proline Analog Compounds of Formula III(b) include compounds of structure (a) and compounds of structure (b), below, as well as pharmaceutically-acceptable salts and solvates thereof:

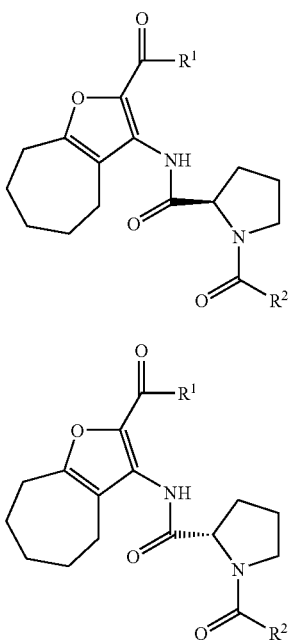

wherein R¹ and R² are as follows:

TABLE 11

| Compound No.: | R¹ | R² |
|---|---|---|
| KAA ((a) and (b)) | piperidin-1-yl | phenyl |
| KAB ((a) and (b)) | piperidin-1-yl | 4-F-phenyl |
| KAC ((a) and (b)) | piperidin-1-yl | 4-CH₃-phenyl |
| KAD ((a) and (b)) | piperidin-1-yl | CH₃ |
| KAE ((a) and (b)) | piperidin-1-yl | 2-furyl |
| KAF ((a) and (b)) | piperidin-1-yl | 2-thienyl |
| KAG ((a) and (b)) | piperazin-1-yl | phenyl |

TABLE 11-continued

| Compound No.: | R¹ | R² |
|---|---|---|
| KAH ((a) and (b)) | piperazin-1-yl | 4-F-phenyl |
| KAI ((a) and (b)) | piperazin-1-yl | 4-CH₃-phenyl |
| KAJ ((a) and (b)) | piperazin-1-yl | CH₃ |
| KAK ((a) and (b)) | piperazin-1-yl | 2-furyl |
| KAL ((a) and (b)) | piperazin-1-yl | 2-thienyl |
| KAM ((a) and (b)) | morpholin-4-yl | phenyl |
| KAN ((a) and (b)) | morpholin-4-yl | 4-F-phenyl |
| KAO ((a) and (b)) | morpholin-4-yl | 4-CH₃-phenyl |
| KAP ((a) and (b)) | morpholin-4-yl | CH₃ |
| KAQ ((a) and (b)) | morpholin-4-yl | 2-furyl |
| KAR ((a) and (b)) | morpholin-4-yl | 2-thienyl |
| KAS ((a) and (b)) | pyrrol-1-yl | phenyl |
| KAT ((a) and (b)) | pyrrol-1-yl | 4-F-phenyl |
| KAU ((a) and (b)) | pyrrol-1-yl | 4-CH₃-phenyl |

TABLE 11-continued

| Compound No.: | R¹ | R² |
|---|---|---|
| KAV ((a) and (b)) | pyrrole-N | —CH₃ |
| KAW ((a) and (b)) | pyrrole-N | furan-2-yl |
| KAX ((a) and (b)) | pyrrole-N | thiophen-2-yl |
| KAY ((a) and (b)) | imidazole-N | phenyl |
| KAZ ((a) and (b)) | imidazole-N | 4-fluorophenyl |
| KBA ((a) and (b)) | imidazole-N | 4-methylphenyl |
| KBB ((a) and (b)) | imidazole-N | —CH₃ |
| KBC ((a) and (b)) | imidazole-N | furan-2-yl |
| KBD ((a) and (b)) | imidazole-N | thiophen-2-yl |
| KBE ((a) and (b)) | —OCH₂CH₃ | phenyl |
| KBF ((a) and (b)) | —OCH₂CH₃ | 4-fluorophenyl |
| KBG ((a) and (b)) | —OCH₂CH₃ | 4-methylphenyl |
| KBH ((a) and (b)) | —OCH₂CH₃ | —CH₃ |
| KBI ((a) and (b)) | —OCH₂CH₃ | furan-2-yl |
| KBJ ((a) and (b)) | —OCH₂CH₃ | thiophen-2-yl |

Illustrative Proline Analog Compounds of Formula I(a) include compounds of structure (a) and compounds of structure (b), below, as well as pharmaceutically-acceptable salts and solvates thereof:

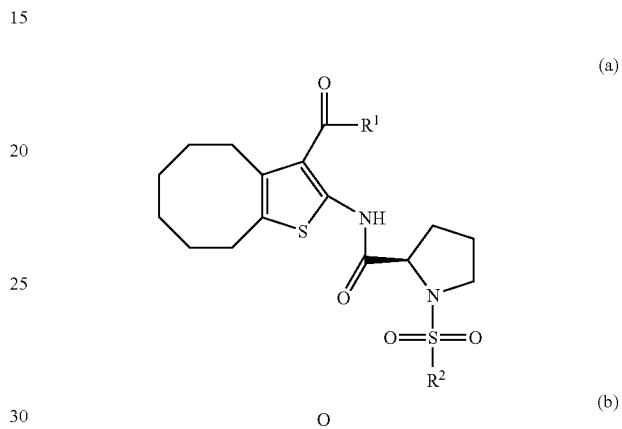

wherein R¹ and R² are as follows:

TABLE 12

| Compound No.: | R¹ | R² |
|---|---|---|
| LAA ((a) and (b)) | piperidine-N | phenyl |
| LAB ((a) and (b)) | piperidine-N | 4-fluorophenyl |
| LAC ((a) and (b)) | piperidine-N | 4-methylphenyl |
| LAD ((a) and (b)) | piperidine-N | —CH₃ |

TABLE 12-continued

| Compound No.: | R¹ | R² |
|---|---|---|
| LAE ((a) and (b)) | piperidine (N) | 2-furyl |
| LAF ((a) and (b)) | piperidine (N) | 2-thienyl |
| LAG ((a) and (b)) | piperazine (N-NH) | phenyl |
| LAH ((a) and (b)) | piperazine (N-NH) | 4-fluorophenyl |
| LAI ((a) and (b)) | piperazine (N-NH) | 4-methylphenyl |
| LAJ ((a) and (b)) | piperazine (N-NH) | —CH₃ |
| LAK ((a) and (b)) | piperazine (N-NH) | 2-furyl |
| LAL ((a) and (b)) | piperazine (N-NH) | 2-thienyl |
| LAM ((a) and (b)) | morpholine (N-O) | phenyl |
| LAN ((a) and (b)) | morpholine (N-O) | 4-fluorophenyl |
| LAO ((a) and (b)) | morpholine (N-O) | 4-methylphenyl |
| LAP ((a) and (b)) | morpholine (N-O) | —CH₃ |
| LAQ ((a) and (b)) | morpholine (N-O) | 2-furyl |
| LAR ((a) and (b)) | morpholine (N-O) | 2-thienyl |
| LAS ((a) and (b)) | pyrrol-1-yl | phenyl |
| LAT ((a) and (b)) | pyrrol-1-yl | 4-fluorophenyl |
| LAU ((a) and (b)) | pyrrol-1-yl | 4-methylphenyl |
| LAV ((a) and (b)) | pyrrol-1-yl | —CH₃ |
| LAW ((a) and (b)) | pyrrol-1-yl | 2-furyl |
| LAX ((a) and (b)) | pyrrol-1-yl | 2-thienyl |
| LAY ((a) and (b)) | imidazol-1-yl | phenyl |
| LAZ ((a) and (b)) | imidazol-1-yl | 4-fluorophenyl |
| LBA ((a) and (b)) | imidazol-1-yl | 4-methylphenyl |
| LBB ((a) and (b)) | imidazol-1-yl | —CH₃ |
| LBC ((a) and (b)) | imidazol-1-yl | 2-furyl |
| LBD ((a) and (b)) | imidazol-1-yl | 2-thienyl |
| LBE ((a) and (b)) | —OCH₂CH₃ | phenyl |
| LBF ((a) and (b)) | —OCH₂CH₃ | 4-fluorophenyl |

TABLE 12-continued

| Compound No.: | R¹ | R² |
|---|---|---|
| LBG ((a) and (b)) | —OCH₂CH₃ | -C₆H₄-CH₃ (para) |
| LBH ((a) and (b)) | —OCH₂CH₃ | —CH₃ |
| LBI ((a) and (b)) | —OCH₂CH₃ | 2-furyl |
| LBJ ((a) and (b)) | —OCH₂CH₃ | 2-thienyl |

Additional, illustrative Proline Analog Compounds of Formula I(b) include compounds of structure (a) and compounds of structure (b), below, as well as pharmaceutically-acceptable salts and solvates thereof:

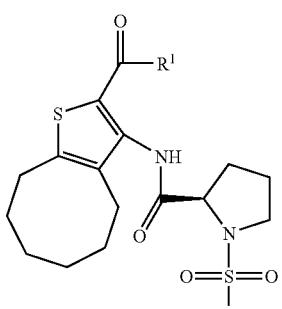

(a)

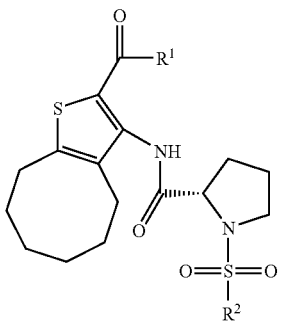

(b)

wherein R¹ and R² are as follows:

TABLE 13

| Compound No.: | R¹ | R² |
|---|---|---|
| MAA ((a) and (b)) | piperidin-1-yl | phenyl |
| MAB ((a) and (b)) | piperidin-1-yl | 4-F-C₆H₄ |
| MAC ((a) and (b)) | piperidin-1-yl | 4-CH₃-C₆H₄ |
| MAD ((a) and (b)) | piperidin-1-yl | —CH₃ |
| MAE ((a) and (b)) | piperidin-1-yl | 2-furyl |
| MAF ((a) and (b)) | piperidin-1-yl | 2-thienyl |
| MAG ((a) and (b)) | piperazin-1-yl | phenyl |
| MAH ((a) and (b)) | piperazin-1-yl | 4-F-C₆H₄ |
| MAI ((a) and (b)) | piperazin-1-yl | 4-CH₃-C₆H₄ |
| MAJ ((a) and (b)) | piperazin-1-yl | —CH₃ |
| MAK ((a) and (b)) | piperazin-1-yl | 2-furyl |
| MAL ((a) and (b)) | piperazin-1-yl | 2-thienyl |
| MAM ((a) and (b)) | morpholin-4-yl | phenyl |
| MAN ((a) and (b)) | morpholin-4-yl | 4-F-C₆H₄ |
| MAO ((a) and (b)) | morpholin-4-yl | 4-CH₃-C₆H₄ |

TABLE 13-continued

| Compound No.: | R¹ | R² |
|---|---|---|
| MAP ((a) and (b)) | morpholine-N | —CH₃ |
| MAQ ((a) and (b)) | morpholine-N | 2-furyl |
| MAR ((a) and (b)) | morpholine-N | 2-thienyl |
| MAS ((a) and (b)) | pyrrol-1-yl | phenyl |
| MAT ((a) and (b)) | pyrrol-1-yl | 4-fluorophenyl |
| MAU ((a) and (b)) | pyrrol-1-yl | 4-methylphenyl |
| MAV ((a) and (b)) | pyrrol-1-yl | —CH₃ |
| MAW ((a) and (b)) | pyrrol-1-yl | 2-furyl |
| MAX ((a) and (b)) | pyrrol-1-yl | 2-thienyl |
| MAY ((a) and (b)) | imidazol-1-yl | phenyl |
| MAZ ((a) and (b)) | imidazol-1-yl | 4-fluorophenyl |
| MBA ((a) and (b)) | imidazol-1-yl | 4-methylphenyl |
| MBB ((a) and (b)) | imidazol-1-yl | —CH₃ |
| MBC ((a) and (b)) | imidazol-1-yl | 2-furyl |
| MBD ((a) and (b)) | imidazol-1-yl | 2-thienyl |
| MBE ((a) and (b)) | —OCH₂CH₃ | phenyl |
| MBF ((a) and (b)) | —OCH₂CH₃ | 4-fluorophenyl |
| MBG ((a) and (b)) | —OCH₂CH₃ | 4-methylphenyl |
| MBH ((a) and (b)) | —OCH₂CH₃ | —CH₃ |
| MBI ((a) and (b)) | —OCH₂CH₃ | 2-furyl |
| MBJ ((a) and (b)) | —OCH₂CH₃ | 2-thienyl |

Illustrative Proline Analog Compounds of Formula III(a) include compounds of structure (a) and compounds of structure (b), below, as well as pharmaceutically-acceptable salts and solvates thereof:

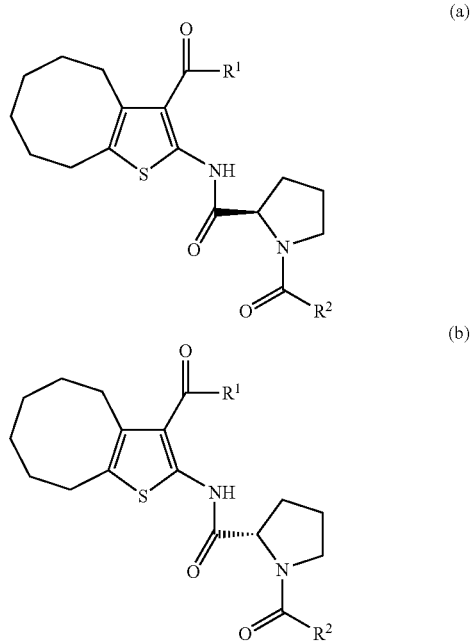

wherein R¹ and R² are as follows:
TABLE 14
| Compound No.: | R¹ | R² |
|---|---|---|
| NAA ((a) and (b)) | 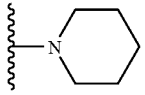 | 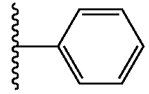 |
| NAB ((a) and (b)) | 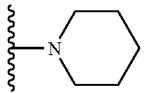 | 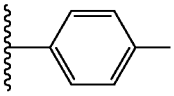 |
| NAC ((a) and (b)) | 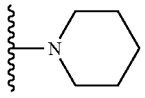 | 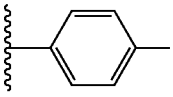 |
| NAD ((a) and (b)) | 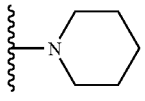 | 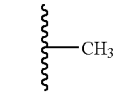 |
| NAE ((a) and (b)) | 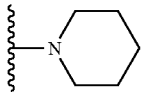 | 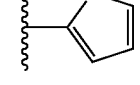 |
| NAF ((a) and (b)) | 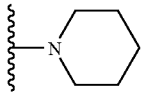 | 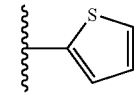 |
| NAG ((a) and (b)) | 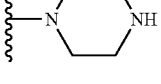 | 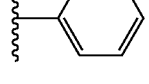 |
| NAH ((a) and (b)) | 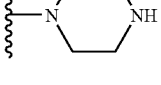 | 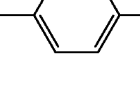 |
| NAI ((a) and (b)) | 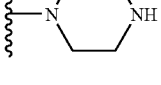 | 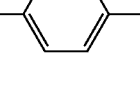 |
| NAJ ((a) and (b)) | 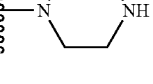 | 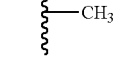 |
| NAK ((a) and (b)) | 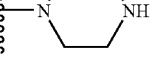 | 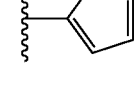 |
| NAL ((a) and (b)) | 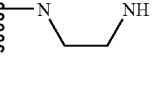 | 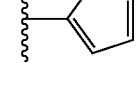 |
| NAM ((a) and (b)) | 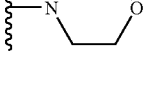 | 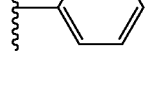 |
TABLE 14-continued
| Compound No.: | R¹ | R² |
|---|---|---|
| NAN ((a) and (b)) | 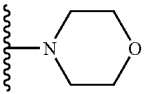 | 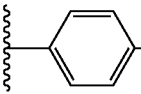 |
| NAO ((a) and (b)) | 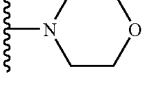 | 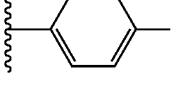 |
| NAP ((a) and (b)) | 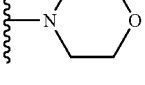 | 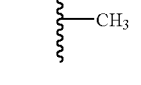 |
| NAQ ((a) and (b)) | 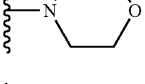 | 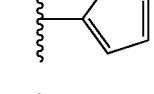 |
| NAR ((a) and (b)) | 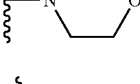 | 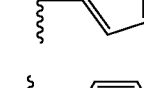 |
| NAS ((a) and (b)) | 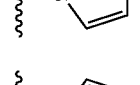 | 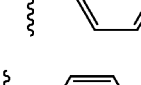 |
| NAT ((a) and (b)) | 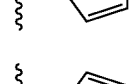 | 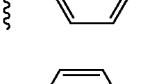 |
| NAU ((a) and (b)) | 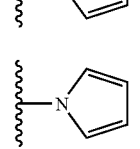 | 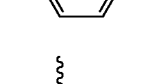 |
| NAV ((a) and (b)) |  | 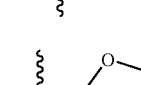 |
| NAW ((a) and (b)) | 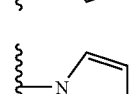 | 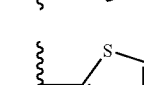 |
| NAX ((a) and (b)) | 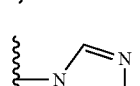 | 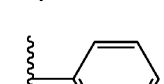 |
| NAY ((a) and (b)) | 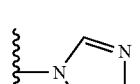 | 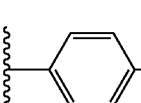 |
| NAZ ((a) and (b)) | 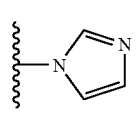 | 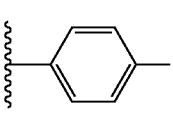 |
| NBA ((a) and (b)) | | |

TABLE 14-continued

| Compound No.: | R¹ | R² |
|---|---|---|
| NBB ((a) and (b)) | imidazol-1-yl | —CH₃ |
| NBC ((a) and (b)) | imidazol-1-yl | furan-2-yl |
| NBD ((a) and (b)) | imidazol-1-yl | thiophen-2-yl |
| NBE ((a) and (b)) | —OCH₂CH₃ | phenyl |
| NBF ((a) and (b)) | —OCH₂CH₃ | 4-fluorophenyl |
| NBG ((a) and (b)) | —OCH₂CH₃ | 4-methylphenyl |
| NBH ((a) and (b)) | —OCH₂CH₃ | —CH₃ |
| NBI ((a) and (b)) | —OCH₂CH₃ | furan-2-yl |
| NBJ ((a) and (b)) | —OCH₂CH₃ | thiophen-2-yl |

Additional, illustrative Proline Analog Compounds of Formula III(b) include compounds of structure (a) and compounds of structure (b), below, as well as pharmaceutically-acceptable salts and solvates thereof:

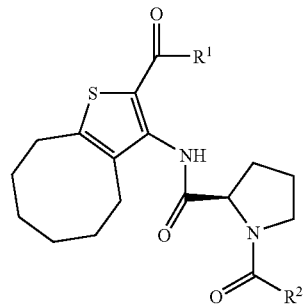
(a)

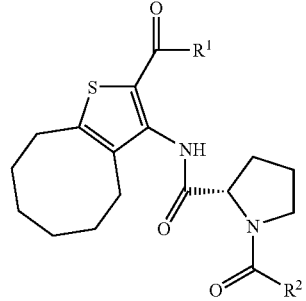
(b)

wherein R¹ and R² are as follows:

TABLE 15

| Compound No.: | R¹ | R² |
|---|---|---|
| OAA ((a) and (b)) | piperidin-1-yl | phenyl |
| OAB ((a) and (b)) | piperidin-1-yl | 4-fluorophenyl |
| OAC ((a) and (b)) | piperidin-1-yl | 4-methylphenyl |
| OAD ((a) and (b)) | piperidin-1-yl | —CH₃ |
| OAE ((a) and (b)) | piperidin-1-yl | furan-2-yl |
| OAF ((a) and (b)) | piperidin-1-yl | thiophen-2-yl |
| OAG ((a) and (b)) | piperazin-1-yl | phenyl |
| OAH ((a) and (b)) | piperazin-1-yl | 4-fluorophenyl |
| OAI ((a) and (b)) | piperazin-1-yl | 4-methylphenyl |
| OAJ ((a) and (b)) | piperazin-1-yl | —CH₃ |

TABLE 15-continued

| Compound No.: | R¹ | R² |
|---|---|---|
| OAK ((a) and (b)) | piperazinyl (N-NH) | 2-furyl |
| OAL ((a) and (b)) | piperazinyl (N-NH) | 2-thienyl |
| OAM ((a) and (b)) | morpholinyl | phenyl |
| OAN ((a) and (b)) | morpholinyl | 4-F-phenyl |
| OAO ((a) and (b)) | morpholinyl | 4-CH₃-phenyl |
| OAP ((a) and (b)) | morpholinyl | —CH₃ |
| OAQ ((a) and (b)) | morpholinyl | 2-furyl |
| OAR ((a) and (b)) | morpholinyl | 2-thienyl |
| OAS ((a) and (b)) | pyrrolyl | phenyl |
| OAT ((a) and (b)) | pyrrolyl | 4-F-phenyl |
| OAU ((a) and (b)) | pyrrolyl | 4-CH₃-phenyl |
| OAV ((a) and (b)) | pyrrolyl | —CH₃ |
| OAW ((a) and (b)) | pyrrolyl | 2-furyl |
| OAX ((a) and (b)) | pyrrolyl | 2-thienyl |
| OAY ((a) and (b)) | imidazolyl | phenyl |
| OAZ ((a) and (b)) | imidazolyl | 4-F-phenyl |
| OBA ((a) and (b)) | imidazolyl | 4-CH₃-phenyl |
| OBB ((a) and (b)) | imidazolyl | —CH₃ |
| OBC ((a) and (b)) | imidazolyl | 2-furyl |
| OBD ((a) and (b)) | imidazolyl | 2-thienyl |
| OBE ((a) and (b)) | —OCH₂CH₃ | phenyl |
| OBF ((a) and (b)) | —OCH₂CH₃ | 4-F-phenyl |
| OBG ((a) and (b)) | —OCH₂CH₃ | 4-CH₃-phenyl |
| OBH ((a) and (b)) | —OCH₂CH₃ | —CH₃ |
| OBI ((a) and (b)) | —OCH₂CH₃ | 2-furyl |
| OBJ ((a) and (b)) | —OCH₂CH₃ | 2-thienyl |

Illustrative Proline Analog Compounds of Formula I(a) include compounds of structure (a) and compounds of structure (b), below, as well as pharmaceutically-acceptable salts and solvates thereof:

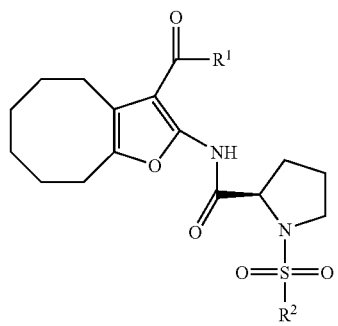
(a)

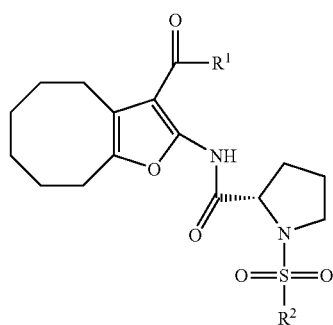
(b)

wherein R¹ and R² are as follows:

TABLE 16

| Compound No.: | R¹ | R² |
|---|---|---|
| PAA ((a) and (b)) | piperidin-1-yl | phenyl |
| PAB ((a) and (b)) | piperidin-1-yl | 4-fluorophenyl |
| PAC ((a) and (b)) | piperidin-1-yl | 4-methylphenyl |
| PAD ((a) and (b)) | piperidin-1-yl | CH₃ |
| PAE ((a) and (b)) | piperidin-1-yl | furan-2-yl |
| PAF ((a) and (b)) | piperidin-1-yl | thiophen-2-yl |
| PAG ((a) and (b)) | piperazin-1-yl | phenyl |

TABLE 16-continued

| Compound No.: | R¹ | R² |
|---|---|---|
| PAH ((a) and (b)) | piperazin-1-yl | 4-fluorophenyl |
| PAI ((a) and (b)) | piperazin-1-yl | 4-methylphenyl |
| PAJ ((a) and (b)) | piperazin-1-yl | CH₃ |
| PAK ((a) and (b)) | piperazin-1-yl | furan-2-yl |
| PAL ((a) and (b)) | piperazin-1-yl | thiophen-2-yl |
| PAM ((a) and (b)) | morpholin-4-yl | phenyl |
| PAN ((a) and (b)) | morpholin-4-yl | 4-fluorophenyl |
| PAO ((a) and (b)) | morpholin-4-yl | 4-methylphenyl |
| PAP ((a) and (b)) | morpholin-4-yl | CH₃ |
| PAQ ((a) and (b)) | morpholin-4-yl | furan-2-yl |
| PAR ((a) and (b)) | morpholin-4-yl | thiophen-2-yl |
| PAS ((a) and (b)) | pyrrol-1-yl | phenyl |
| PAT ((a) and (b)) | pyrrol-1-yl | 4-fluorophenyl |
| PAU ((a) and (b)) | pyrrol-1-yl | 4-methylphenyl |

TABLE 16-continued

| Compound No.: | R¹ | R² |
|---|---|---|
| PAV ((a) and (b)) | pyrrole-N | —CH₃ |
| PAW ((a) and (b)) | pyrrole-N | 2-furyl |
| PAX ((a) and (b)) | pyrrole-N | 2-thienyl |
| PAY ((a) and (b)) | imidazole-N | phenyl |
| PAZ ((a) and (b)) | imidazole-N | 4-F-phenyl |
| PBA ((a) and (b)) | imidazole-N | 4-CH₃-phenyl |
| PBB ((a) and (b)) | imidazole-N | —CH₃ |
| PBC ((a) and (b)) | imidazole-N | 2-furyl |
| PBD ((a) and (b)) | imidazole-N | 2-thienyl |
| PBE ((a) and (b)) | —OCH₂CH₃ | phenyl |
| PBF ((a) and (b)) | —OCH₂CH₃ | 4-F-phenyl |
| PBG ((a) and (b)) | —OCH₂CH₃ | 4-CH₃-phenyl |
| PBH ((a) and (b)) | —OCH₂CH₃ | —CH₃ |
| PBI ((a) and (b)) | —OCH₂CH₃ | 2-furyl |
| PBJ ((a) and (b)) | —OCH₂CH₃ | 2-thienyl |

Additional, illustrative Proline Analog Compounds of Formula I(b) include compounds of structure (a) and compounds of structure (b), below, as well as pharmaceutically-acceptable salts and solvates thereof:

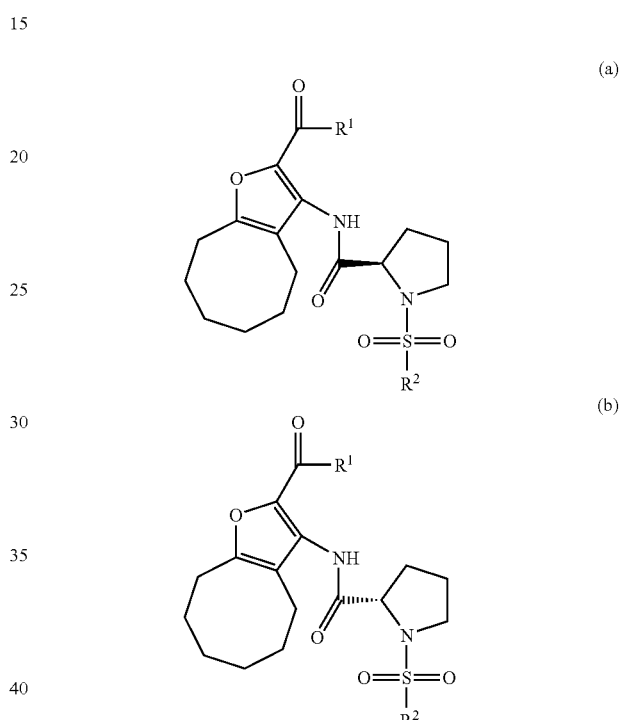

wherein R¹ and R² are as follows:

TABLE 17

| Compound No.: | R¹ | R² |
|---|---|---|
| QAA ((a) and (b)) | piperidine-N | phenyl |
| QAB ((a) and (b)) | piperidine-N | 4-F-phenyl |
| QAC ((a) and (b)) | piperidine-N | 4-CH₃-phenyl |
| QAD ((a) and (b)) | piperidine-N | —CH₃ |

TABLE 17-continued

| Compound No.: | R¹ | R² |
|---|---|---|
| QAE ((a) and (b)) | piperidinyl (N) | 2-furyl |
| QAF ((a) and (b)) | piperidinyl (N) | 2-thienyl |
| QAG ((a) and (b)) | piperazinyl (N–NH) | phenyl |
| QAH ((a) and (b)) | piperazinyl (N–NH) | 4-fluorophenyl |
| QAI ((a) and (b)) | piperazinyl (N–NH) | 4-methylphenyl |
| QAJ ((a) and (b)) | piperazinyl (N–NH) | CH₃ |
| QAK ((a) and (b)) | piperazinyl (N–NH) | 2-furyl |
| QAL ((a) and (b)) | piperazinyl (N–NH) | 2-thienyl |
| QAM ((a) and (b)) | morpholinyl | phenyl |
| QAN ((a) and (b)) | morpholinyl | 4-fluorophenyl |
| QAO ((a) and (b)) | morpholinyl | 4-methylphenyl |
| QAP ((a) and (b)) | morpholinyl | CH₃ |
| QAQ ((a) and (b)) | morpholinyl | 2-furyl |
| QAR ((a) and (b)) | morpholinyl | 2-thienyl |
| QAS ((a) and (b)) | pyrrolyl | phenyl |
| QAT ((a) and (b)) | pyrrolyl | 4-fluorophenyl |
| QAU ((a) and (b)) | pyrrolyl | 4-methylphenyl |
| QAV ((a) and (b)) | pyrrolyl | CH₃ |
| QAW ((a) and (b)) | pyrrolyl | 2-furyl |
| QAX ((a) and (b)) | pyrrolyl | 2-thienyl |
| QAY ((a) and (b)) | imidazolyl | phenyl |
| QAZ ((a) and (b)) | imidazolyl | 4-fluorophenyl |
| QBA ((a) and (b)) | imidazolyl | 4-methylphenyl |
| QBB ((a) and (b)) | imidazolyl | CH₃ |
| QBC ((a) and (b)) | imidazolyl | 2-furyl |
| QBD ((a) and (b)) | imidazolyl | 2-thienyl |
| QBE ((a) and (b)) | —OCH₂CH₃ | phenyl |
| QBF ((a) and (b)) | —OCH₂CH₃ | 4-fluorophenyl |

TABLE 17-continued

| Compound No.: | R¹ | R² |
|---|---|---|
| QBG ((a) and (b)) | —OCH₂CH₃ | 4-CH₃-phenyl |
| QBH ((a) and (b)) | —OCH₂CH₃ | —CH₃ |
| QBI ((a) and (b)) | —OCH₂CH₃ | 2-furyl |
| QBJ ((a) and (b)) | —OCH₂CH₃ | 2-thienyl |

Illustrative Proline Analog Compounds of Formula III(a) include compounds of structure (a) and compounds of structure (b), below, as well as pharmaceutically-acceptable salts and solvates thereof:

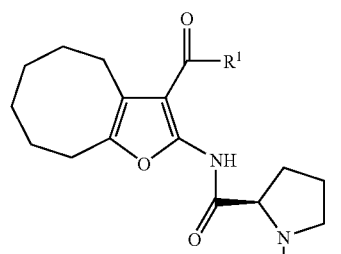

(a)

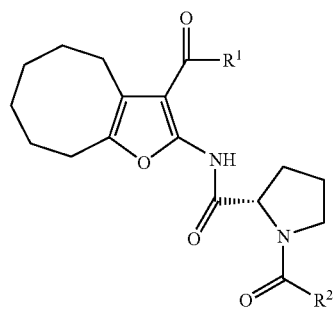

(b)

wherein R¹ and R² are as follows:

TABLE 18

| Compound No.: | R¹ | R² |
|---|---|---|
| RAA ((a) and (b)) | piperidin-1-yl | phenyl |
| RAB ((a) and (b)) | piperidin-1-yl | 4-F-phenyl |
| RAC ((a) and (b)) | piperidin-1-yl | 4-CH₃-phenyl |
| RAD ((a) and (b)) | piperidin-1-yl | —CH₃ |
| RAE ((a) and (b)) | piperidin-1-yl | 2-furyl |
| RAF ((a) and (b)) | piperidin-1-yl | 2-thienyl |
| RAG ((a) and (b)) | piperazin-1-yl | phenyl |
| RAH ((a) and (b)) | piperazin-1-yl | 4-F-phenyl |
| RAI ((a) and (b)) | piperazin-1-yl | 4-CH₃-phenyl |
| RAJ ((a) and (b)) | piperazin-1-yl | —CH₃ |
| RAK ((a) and (b)) | piperazin-1-yl | 2-furyl |
| RAL ((a) and (b)) | piperazin-1-yl | 2-thienyl |
| RAM ((a) and (b)) | morpholin-4-yl | phenyl |
| RAN ((a) and (b)) | morpholin-4-yl | 4-F-phenyl |
| RAO ((a) and (b)) | morpholin-4-yl | 4-CH₃-phenyl |

TABLE 18-continued

| Compound No.: | R¹ | R² |
|---|---|---|
| RAP ((a) and (b)) | N-morpholine | —CH₃ |
| RAQ ((a) and (b)) | N-morpholine | 2-furyl |
| RAR ((a) and (b)) | N-morpholine | 2-thienyl |
| RAS ((a) and (b)) | N-pyrrolyl | phenyl |
| RAT ((a) and (b)) | N-pyrrolyl | 4-F-phenyl |
| RAU ((a) and (b)) | N-pyrrolyl | 4-CH₃-phenyl |
| RAV ((a) and (b)) | N-pyrrolyl | —CH₃ |
| RAW ((a) and (b)) | N-pyrrolyl | 2-furyl |
| RAX ((a) and (b)) | N-pyrrolyl | 2-thienyl |
| RAY ((a) and (b)) | N-imidazolyl | phenyl |
| RAZ ((a) and (b)) | N-imidazolyl | 4-F-phenyl |
| RBA ((a) and (b)) | N-imidazolyl | 4-CH₃-phenyl |
| RBB ((a) and (b)) | N-imidazolyl | —CH₃ |
| RBC ((a) and (b)) | N-imidazolyl | 2-furyl |
| RBD ((a) and (b)) | N-imidazolyl | 2-thienyl |
| RBE ((a) and (b)) | —OCH₂CH₃ | phenyl |
| RBF ((a) and (b)) | —OCH₂CH₃ | 4-F-phenyl |
| RBG ((a) and (b)) | —OCH₂CH₃ | 4-CH₃-phenyl |
| RBH ((a) and (b)) | —OCH₂CH₃ | —CH₃ |
| RBI ((a) and (b)) | —OCH₂CH₃ | 2-furyl |
| RBJ ((a) and (b)) | —OCH₂CH₃ | 2-thienyl |

Additional, illustrative Proline Analog Compounds of Formula III(b) include compounds of structure (a) and compounds of structure (b), below, as well as pharmaceutically-acceptable salts and solvates thereof;

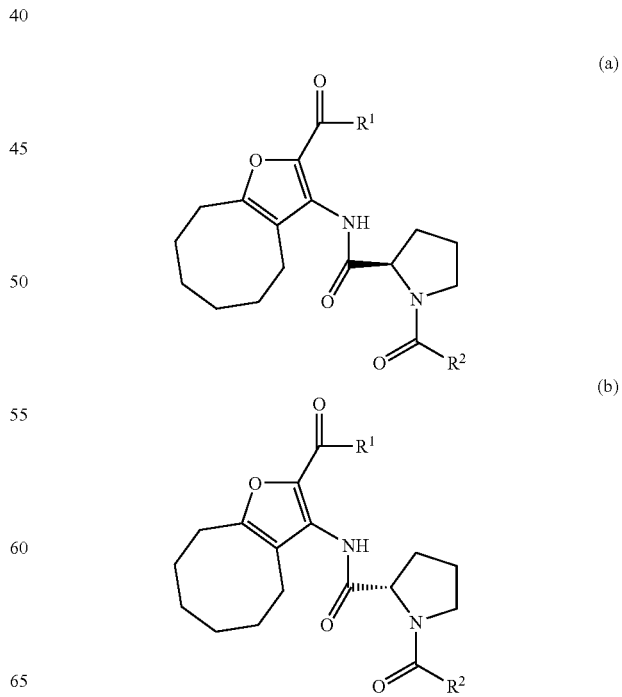

wherein R¹ and R² are as follows:

TABLE 19

| Compound No.: | R¹ | R² |
|---|---|---|
| SAA ((a) and (b)) | piperidine (N-linked) | phenyl |
| SAB ((a) and (b)) | piperidine (N-linked) | 4-fluorophenyl |
| SAC ((a) and (b)) | piperidine (N-linked) | 4-methylphenyl |
| SAD ((a) and (b)) | piperidine (N-linked) | CH₃ |
| SAE ((a) and (b)) | piperidine (N-linked) | 2-furyl |
| SAF ((a) and (b)) | piperidine (N-linked) | 2-thienyl |
| SAG ((a) and (b)) | piperazine (N-linked, NH) | phenyl |
| SAH ((a) and (b)) | piperazine (N-linked, NH) | 4-fluorophenyl |
| SAI ((a) and (b)) | piperazine (N-linked, NH) | 4-methylphenyl |
| SAJ ((a) and (b)) | piperazine (N-linked, NH) | CH₃ |
| SAK ((a) and (b)) | piperazine (N-linked, NH) | 2-furyl |
| SAL ((a) and (b)) | piperazine (N-linked, NH) | 2-thienyl |
| SAM ((a) and (b)) | morpholine (N-linked) | phenyl |
| SAN ((a) and (b)) | morpholine (N-linked) | 4-fluorophenyl |

TABLE 19-continued

| Compound No.: | R¹ | R² |
|---|---|---|
| SAO ((a) and (b)) | morpholine (N-linked) | 4-methylphenyl |
| SAP ((a) and (b)) | morpholine (N-linked) | CH₃ |
| SAQ ((a) and (b)) | morpholine (N-linked) | 2-furyl |
| SAR ((a) and (b)) | morpholine (N-linked) | 2-thienyl |
| SAS ((a) and (b)) | pyrrolyl (N-linked) | phenyl |
| SAT ((a) and (b)) | pyrrolyl (N-linked) | 4-fluorophenyl |
| SAU ((a) and (b)) | pyrrolyl (N-linked) | 4-methylphenyl |
| SAV ((a) and (b)) | pyrrolyl (N-linked) | CH₃ |
| SAW ((a) and (b)) | pyrrolyl (N-linked) | 2-furyl |
| SAX ((a) and (b)) | pyrrolyl (N-linked) | 2-thienyl |
| SAY ((a) and (b)) | imidazolyl (N-linked) | phenyl |
| SAZ ((a) and (b)) | imidazolyl (N-linked) | 4-fluorophenyl |
| SBA ((a) and (b)) | imidazolyl (N-linked) | 4-methylphenyl |
| SBB ((a) and (b)) | imidazolyl (N-linked) | CH₃ |

TABLE 19-continued

| Compound No.: | R¹ | R² |
|---|---|---|
| SBC ((a) and (b)) | imidazol-1-yl | furan-2-yl |
| SBD ((a) and (b)) | imidazol-1-yl | thien-2-yl |
| SBE ((a) and (b)) | —OCH₂CH₃ | phenyl |
| SBF ((a) and (b)) | —OCH₂CH₃ | 4-fluorophenyl |
| SBG ((a) and (b)) | —OCH₂CH₃ | 4-methylphenyl |
| SBH ((a) and (b)) | —OCH₂CH₃ | —CH₃ |
| SBI ((a) and (b)) | —OCH₂CH₃ | furan-2-yl |
| SBJ ((a) and (b)) | —OCH₂CH₃ | thien-2-yl |

Illustrative Proline Analog Compounds of Formula I(b) include compounds of structure (a) and compounds of structure (b), below, as well as pharmaceutically-acceptable salts and solvates thereof:

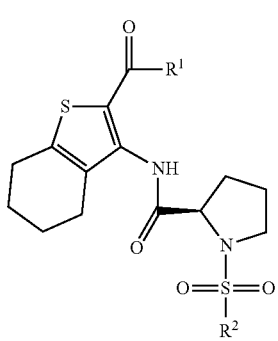
(a)

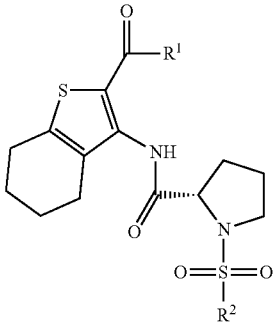
(b)

wherein R¹ and R² are as follows:

TABLE 20

| Compound No.: | R¹ | R² |
|---|---|---|
| TAA ((a) and (b)) | piperidin-1-yl | phenyl |
| TAB ((a) and (b)) | piperidin-1-yl | 4-fluorophenyl |
| TAC ((a) and (b)) | piperidin-1-yl | 4-methylphenyl |
| TAD ((a) and (b)) | piperidin-1-yl | —CH₃ |
| TAE ((a) and (b)) | piperidin-1-yl | furan-2-yl |
| TAF ((a) and (b)) | piperidin-1-yl | thien-2-yl |
| TAG ((a) and (b)) | piperazin-1-yl | phenyl |
| TAH ((a) and (b)) | piperazin-1-yl | 4-fluorophenyl |
| TAI ((a) and (b)) | piperazin-1-yl | 4-methylphenyl |
| TAJ ((a) and (b)) | piperazin-1-yl | —CH₃ |

TABLE 20-continued

| Compound No.: | R¹ | R² |
|---|---|---|
| TAK ((a) and (b)) | piperazine (N-NH) | 2-furyl |
| TAL ((a) and (b)) | piperazine (N-NH) | 2-thienyl |
| TAM ((a) and (b)) | morpholine | phenyl |
| TAN ((a) and (b)) | morpholine | 4-F-phenyl |
| TAO ((a) and (b)) | morpholine | 4-CH₃-phenyl |
| TAP ((a) and (b)) | morpholine | —CH₃ |
| TAQ ((a) and (b)) | morpholine | 2-furyl |
| TAR ((a) and (b)) | morpholine | 2-thienyl |
| TAS ((a) and (b)) | pyrrolyl | phenyl |
| TAT ((a) and (b)) | pyrrolyl | 4-F-phenyl |
| TAU ((a) and (b)) | pyrrolyl | 4-CH₃-phenyl |
| TAV ((a) and (b)) | pyrrolyl | —CH₃ |
| TAW ((a) and (b)) | pyrrolyl | 2-furyl |
| TAX ((a) and (b)) | pyrrolyl | 2-thienyl |
| TAY ((a) and (b)) | imidazolyl | phenyl |
| TAZ ((a) and (b)) | imidazolyl | 4-F-phenyl |
| TBA ((a) and (b)) | imidazolyl | 4-CH₃-phenyl |
| TBB ((a) and (b)) | imidazolyl | —CH₃ |
| TBC ((a) and (b)) | imidazolyl | 2-furyl |
| TBD ((a) and (b)) | imidazolyl | 2-thienyl |
| TBE ((a) and (b)) | —OCH₂CH₃ | phenyl |
| TBF ((a) and (b)) | —OCH₂CH₃ | 4-F-phenyl |
| TBG ((a) and (b)) | —OCH₂CH₃ | 4-CH₃-phenyl |
| TBH ((a) and (b)) | —OCH₂CH₃ | —CH₃ |
| TBI ((a) and (b)) | —OCH₂CH₃ | 2-furyl |
| TBJ ((a) and (b)) | —OCH₂CH₃ | 2-thienyl |

Additional, illustrative Proline Analog Compounds of the Formula III(a) include compounds of structure (a) and compounds of structure (b), below, as well as pharmaceutically-acceptable salts and solvates thereof:

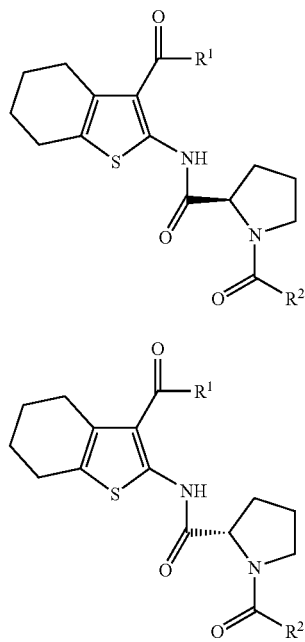

wherein R[1] and R[2] are as follows:

TABLE 21

| Compound No.: | R[1] | R[2] |
|---|---|---|
| UAA ((a) and (b)) | N-piperidinyl | phenyl |
| UAB ((a) and (b)) | N-piperidinyl | 4-F-phenyl |
| UAC ((a) and (b)) | N-piperidinyl | 4-CH₃-phenyl |
| UAD ((a) and (b)) | N-piperidinyl | CH₃ |
| UAE ((a) and (b)) | N-piperidinyl | 2-furyl |
| UAF ((a) and (b)) | N-piperidinyl | 2-thienyl |
| UAG ((a) and (b)) | piperazinyl | phenyl |

TABLE 21-continued

| Compound No.: | R[1] | R[2] |
|---|---|---|
| UAH ((a) and (b)) | piperazinyl | 4-F-phenyl |
| UAI ((a) and (b)) | piperazinyl | 4-CH₃-phenyl |
| UAJ ((a) and (b)) | piperazinyl | CH₃ |
| UAK ((a) and (b)) | piperazinyl | 2-furyl |
| UAL ((a) and (b)) | piperazinyl | 2-thienyl |
| UAM ((a) and (b)) | morpholinyl | phenyl |
| UAN ((a) and (b)) | morpholinyl | 4-F-phenyl |
| UAO ((a) and (b)) | morpholinyl | 4-CH₃-phenyl |
| UAP ((a) and (b)) | morpholinyl | CH₃ |
| UAQ ((a) and (b)) | morpholinyl | 2-furyl |
| UAR ((a) and (b)) | morpholinyl | 2-thienyl |
| UAS ((a) and (b)) | pyrrolyl | phenyl |
| UAT ((a) and (b)) | pyrrolyl | 4-F-phenyl |
| UAU ((a) and (b)) | pyrrolyl | 4-CH₃-phenyl |

TABLE 21-continued

| Compound No.: | R¹ | R² |
|---|---|---|
| UAV ((a) and (b)) | pyrrole-N | —CH₃ |
| UAW ((a) and (b)) | pyrrole-N | furan-2-yl |
| UAX ((a) and (b)) | pyrrole-N | thiophene-2-yl |
| UAY ((a) and (b)) | imidazole-N | phenyl |
| UAZ ((a) and (b)) | imidazole-N | 4-F-phenyl |
| UBA ((a) and (b)) | imidazole-N | 4-CH₃-phenyl |
| UBB ((a) and (b)) | imidazole-N | —CH₃ |
| UBC ((a) and (b)) | imidazole-N | furan-2-yl |
| UBD ((a) and (b)) | imidazole-N | thiophene-2-yl |
| UBE ((a) and (b)) | —OCH₂CH₃ | phenyl |
| UBF ((a) and (b)) | —OCH₂CH₃ | 4-F-phenyl |
| UBG ((a) and (b)) | —OCH₂CH₃ | 4-CH₃-phenyl |
| UBH ((a) and (b)) | —OCH₂CH₃ | —CH₃ |
| UBI ((a) and (b)) | —OCH₂CH₃ | furan-2-yl |
| UBJ ((a) and (b)) | —OCH₂CH₃ | thiophene-2-yl |

Illustrative Proline Analog Compounds of the Formula III(b) include compounds of structure (a) and compounds of structure (b), below, as well as pharmaceutically-acceptable salts and solvates thereof:

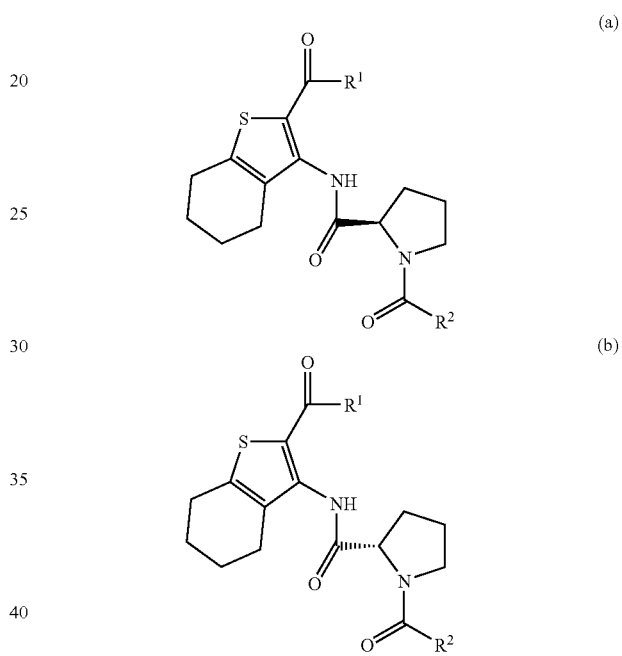

wherein R¹ and R² are as follows:

TABLE 22

| Compound No.: | R¹ | R² |
|---|---|---|
| VAA ((a) and (b)) | piperidine-N | phenyl |
| VAB ((a) and (b)) | piperidine-N | 4-F-phenyl |
| VAC ((a) and (b)) | piperidine-N | 4-CH₃-phenyl |
| VAD ((a) and (b)) | piperidine-N | —CH₃ |

TABLE 22-continued

| Compound No.: | R¹ | R² |
|---|---|---|
| VAF ((a) and (b)) | piperidinyl (N) | 2-furyl |
| VAF ((a) and (b)) | piperidinyl (N) | 2-thienyl |
| VAG ((a) and (b)) | piperazinyl (N-NH) | phenyl |
| VAH ((a) and (b)) | piperazinyl (N-NH) | 4-F-phenyl |
| VAI ((a) and (b)) | piperazinyl (N-NH) | 4-CH₃-phenyl |
| VAJ ((a) and (b)) | piperazinyl (N-NH) | CH₃ |
| VAK ((a) and (b)) | piperazinyl (N-NH) | 2-furyl |
| VAL ((a) and (b)) | piperazinyl (N-NH) | 2-thienyl |
| VAM ((a) and (b)) | morpholinyl | phenyl |
| VAN ((a) and (b)) | morpholinyl | 4-F-phenyl |
| VAO ((a) and (b)) | morpholinyl | 4-CH₃-phenyl |
| VAP ((a) and (b)) | morpholinyl | CH₃ |
| VAQ ((a) and (b)) | morpholinyl | 2-furyl |
| VAR ((a) and (b)) | morpholinyl | 2-thienyl |
| VAS ((a) and (b)) | pyrrolyl | phenyl |
| VAT ((a) and (b)) | pyrrolyl | 4-F-phenyl |
| VAU ((a) and (b)) | pyrrolyl | 4-CH₃-phenyl |
| VAV ((a) and (b)) | pyrrolyl | CH₃ |
| VAW ((a) and (b)) | pyrrolyl | 2-furyl |
| VAX ((a) and (b)) | pyrrolyl | 2-thienyl |
| VAY ((a) and (b)) | imidazolyl | phenyl |
| VAZ ((a) and (b)) | imidazolyl | 4-F-phenyl |
| VBA ((a) and (b)) | imidazolyl | 4-CH₃-phenyl |
| VBB ((a) and (b)) | imidazolyl | CH₃ |
| VBC ((a) and (b)) | imidazolyl | 2-furyl |
| VBD ((a) and (b)) | imidazolyl | 2-thienyl |
| VBE ((a) and (b)) | —OCH₂CH₃ | phenyl |
| VBF ((a) and (b)) | —OCH₂CH₃ | 4-F-phenyl |

TABLE 22-continued

| Compound No.: | R¹ | R² |
|---|---|---|
| VBG ((a) and (b)) | —OCH₂CH₃ | -C₆H₄-CH₃ (para) |
| VBH ((a) and (b)) | —OCH₂CH₃ | —CH₃ |
| VBI ((a) and (b)) | —OCH₂CH₃ | 2-furyl |
| VBJ ((a) and (b)) | —OCH₂CH₃ | 2-thienyl |

Additional, illustrative Proline Analog Compounds of Formula I(b) include compounds of structure (a) and compounds of structure (b), below, as well as pharmaceutically-acceptable salts and solvates thereof:

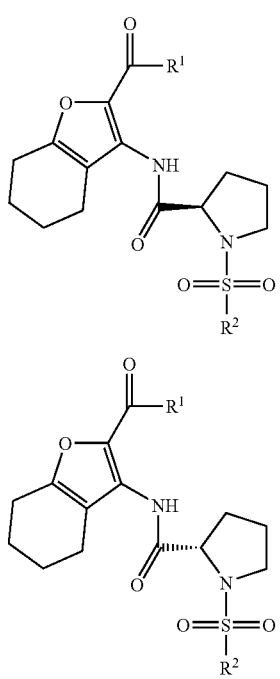

wherein R¹ and R² are as follows:

TABLE 23

| Compound No.: | R¹ | R² |
|---|---|---|
| WAA ((a) and (b)) | piperidin-1-yl | phenyl |
| WAB ((a) and (b)) | piperidin-1-yl | 4-fluorophenyl |
| WAC ((a) and (b)) | piperidin-1-yl | 4-methylphenyl |
| WAD ((a) and (b)) | piperidin-1-yl | —CH₃ |
| WAE ((a) and (b)) | piperidin-1-yl | 2-furyl |
| WAF ((a) and (b)) | piperidin-1-yl | 2-thienyl |
| WAG ((a) and (b)) | piperazin-1-yl | phenyl |
| WAH ((a) and (b)) | piperazin-1-yl | 4-fluorophenyl |
| WAI ((a) and (b)) | piperazin-1-yl | 4-methylphenyl |
| WAJ ((a) and (b)) | piperazin-1-yl | —CH₃ |
| WAK ((a) and (b)) | piperazin-1-yl | 2-furyl |
| WAL ((a) and (b)) | piperazin-1-yl | 2-thienyl |
| WAM ((a) and (b)) | morpholin-4-yl | phenyl |
| WAN ((a) and (b)) | morpholin-4-yl | 4-fluorophenyl |
| WAO ((a) and (b)) | morpholin-4-yl | 4-methylphenyl |

TABLE 23-continued

| Compound No.: | R¹ | R² |
|---|---|---|
| WAP ((a) and (b)) | morpholin-4-yl (N-linked) | —CH₃ |
| WAQ ((a) and (b)) | morpholin-4-yl (N-linked) | furan-2-yl |
| WAR ((a) and (b)) | morpholin-4-yl (N-linked) | thiophen-2-yl |
| WAS ((a) and (b)) | pyrrol-1-yl | phenyl |
| WAT ((a) and (b)) | pyrrol-1-yl | 4-fluorophenyl |
| WAU ((a) and (b)) | pyrrol-1-yl | 4-methylphenyl |
| WAV ((a) and (b)) | pyrrol-1-yl | —CH₃ |
| WAW ((a) and (b)) | pyrrol-1-yl | furan-2-yl |
| WAX ((a) and (b)) | pyrrol-1-yl | thiophen-2-yl |
| WAY ((a) and (b)) | imidazol-1-yl | phenyl |
| WAZ ((a) and (b)) | imidazol-1-yl | 4-fluorophenyl |
| WBA ((a) and (b)) | imidazol-1-yl | 4-methylphenyl |
| WBB ((a) and (b)) | imidazol-1-yl | —CH₃ |
| WBC ((a) and (b)) | imidazol-1-yl | furan-2-yl |
| WBD ((a) and (b)) | imidazol-1-yl | thiophen-2-yl |
| WBE ((a) and (b)) | —OCH₂CH₃ | phenyl |
| WBF ((a) and (b)) | —OCH₂CH₃ | 4-fluorophenyl |
| WBG ((a) and (b)) | —OCH₂CH₃ | 4-methylphenyl |
| WBH ((a) and (b)) | —OCH₂CH₃ | —CH₃ |
| WBI ((a) and (b)) | —OCH₂CH₃ | furan-2-yl |
| WBJ ((a) and (b)) | —OCH₂CH₃ | thiophen-2-yl |

Illustrative Proline Analog Compounds of Formula III(a) include compounds of structure (a) and compounds of structure (b), below, as well as pharmaceutically-acceptable salts and solvates thereof:

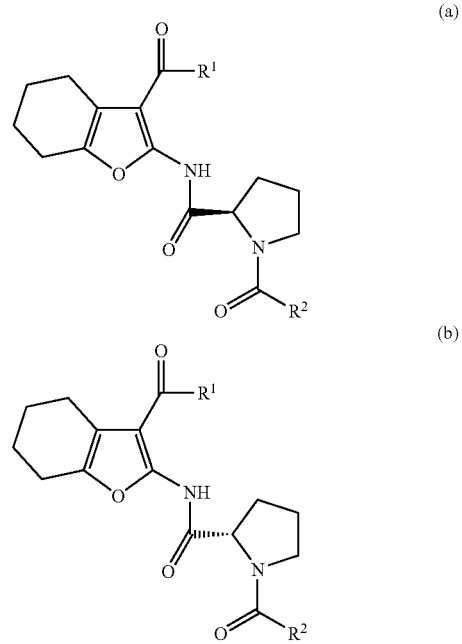

wherein R[1] and R[2] are as follows:

TABLE 24

| Compound No.: | R[1] | R[2] |
|---|---|---|
| XAA ((a) and (b)) | piperidin-1-yl | phenyl |
| XAB ((a) and (b)) | piperidin-1-yl | 4-fluorophenyl |
| XAC ((a) and (b)) | piperidin-1-yl | 4-methylphenyl |
| XAD ((a) and (b)) | piperidin-1-yl | CH$_3$ |
| XAE ((a) and (b)) | piperidin-1-yl | furan-2-yl |
| XAF ((a) and (b)) | piperidin-1-yl | thiophen-2-yl |
| XAG ((a) and (b)) | piperazin-1-yl | phenyl |
| XAH ((a) and (b)) | piperazin-1-yl | 4-fluorophenyl |
| XAI ((a) and (b)) | piperazin-1-yl | 4-methylphenyl |
| XAJ ((a) and (b)) | piperazin-1-yl | CH$_3$ |
| XAK ((a) and (b)) | piperazin-1-yl | furan-2-yl |
| XAL ((a) and (b)) | piperazin-1-yl | thiophen-2-yl |
| XAM ((a) and (b)) | morpholin-4-yl | phenyl |
| XAN ((a) and (b)) | morpholin-4-yl | 4-fluorophenyl |
| XAO ((a) and (b)) | morpholin-4-yl | 4-methylphenyl |
| XAP ((a) and (b)) | morpholin-4-yl | CH$_3$ |
| XAQ ((a) and (b)) | morpholin-4-yl | furan-2-yl |
| XAR ((a) and (b)) | morpholin-4-yl | thiophen-2-yl |
| XAS ((a) and (b)) | pyrrol-1-yl | phenyl |
| XAT ((a) and (b)) | pyrrol-1-yl | 4-fluorophenyl |
| XAU ((a) and (b)) | pyrrol-1-yl | 4-methylphenyl |
| XAV ((a) and (b)) | pyrrol-1-yl | CH$_3$ |
| XAW ((a) and (b)) | pyrrol-1-yl | furan-2-yl |
| XAX ((a) and (b)) | pyrrol-1-yl | thiophen-2-yl |
| XAY ((a) and (b)) | imidazol-1-yl | phenyl |
| XAZ ((a) and (b)) | imidazol-1-yl | 4-fluorophenyl |
| XBA ((a) and (b)) | imidazol-1-yl | 4-methylphenyl |
| XBB ((a) and (b)) | imidazol-1-yl | CH$_3$ |

TABLE 24-continued

| Compound No.: | R¹ | R² |
|---|---|---|
| XBC ((a) and (b)) | imidazolyl | 2-furyl |
| XBD ((a) and (b)) | imidazolyl | 2-thienyl |
| XBE ((a) and (b)) | —OCH₂CH₃ | phenyl |
| XBF ((a) and (b)) | —OCH₂CH₃ | 4-fluorophenyl |
| XBG ((a) and (b)) | —OCH₂CH₃ | 4-methylphenyl |
| XBH ((a) and (b)) | —OCH₂CH₃ | —CH₃ |
| XBI ((a) and (b)) | —OCH₂CH₃ | 2-furyl |
| XBJ ((a) and (b)) | —OCH₂CH₃ | 2-thienyl |

Additional, illustrative Proline Analog Compounds of the Formula III(b) include compounds of structure (a) and compounds of structure (b), below, as well as pharmaceutically-acceptable salts and solvates thereof:

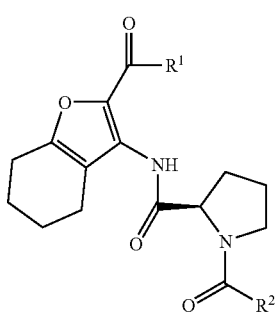

(a)

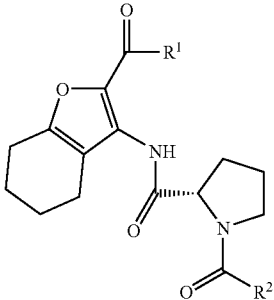

(b)

wherein R¹ and R² are as follows:

TABLE 25

| Compound No.: | R¹ | R² |
|---|---|---|
| YAA ((a) and (b)) | piperidinyl | phenyl |
| YAP ((a) and (b)) | piperidinyl | 4-fluorophenyl |
| YAC ((a) and (b)) | piperidinyl | 4-methylphenyl |
| YAD ((a) and (b)) | piperidinyl | —CH₃ |
| YAE ((a) and (b)) | piperidinyl | 2-furyl |
| YAF ((a) and (b)) | piperidinyl | 2-thienyl |
| YAG ((a) and (b)) | piperazinyl | phenyl |
| YAH ((a) and (b)) | piperazinyl | 4-fluorophenyl |
| YAI ((a) and (b)) | piperazinyl | 4-methylphenyl |
| YAJ ((a) and (b)) | piperazinyl | —CH₃ |

TABLE 25-continued

| Compound No.: | R¹ | R² |
|---|---|---|
| YAK ((a) and (b)) | piperazine (N-linked, NH) | 2-furyl |
| YAL ((a) and (b)) | piperazine (N-linked, NH) | 2-thienyl |
| YAM ((a) and (b)) | morpholine (N-linked) | phenyl |
| YAN ((a) and (b)) | morpholine (N-linked) | 4-F-phenyl |
| YAO ((a) and (b)) | morpholine (N-linked) | 4-CH₃-phenyl |
| YAP ((a) and (b)) | morpholine (N-linked) | CH₃ |
| YAQ ((a) and (b)) | morpholine (N-linked) | 2-furyl |
| YAR ((a) and (b)) | morpholine (N-linked) | 2-thienyl |
| YAS ((a) and (b)) | pyrrol-1-yl | phenyl |
| YAT ((a) and (b)) | pyrrol-1-yl | 4-F-phenyl |
| YAU ((a) and (b)) | pyrrol-1-yl | 4-CH₃-phenyl |
| YAV ((a) and (b)) | pyrrol-1-yl | CH₃ |
| YAW ((a) and (b)) | pyrrol-1-yl | 2-furyl |
| YAX ((a) and (b)) | pyrrol-1-yl | 2-thienyl |
| YAY ((a) and (b)) | imidazol-1-yl | phenyl |
| YAZ ((a) and (b)) | imidazol-1-yl | 4-F-phenyl |
| YBA ((a) and (b)) | imidazol-1-yl | 4-CH₃-phenyl |
| YBB ((a) and (b)) | imidazol-1-yl | CH₃ |
| YBC ((a) and (b)) | imidazol-1-yl | 2-furyl |
| YBD ((a) and (b)) | imidazol-1-yl | 2-thienyl |
| YBE ((a) and (b)) | —OCH₂CH₃ | phenyl |
| YBF ((a) and (b)) | —OCH₂CH₃ | 4-F-phenyl |
| YBG ((a) and (b)) | —OCH₂CH₃ | 4-CH₃-phenyl |
| YBH ((a) and (b)) | —OCH₂CH₃ | CH₃ |
| YBI ((a) and (b)) | —OCH₂CH₃ | 2-furyl |
| YBJ ((a) and (b)) | —OCH₂CH₃ | 2-thienyl |

In certain embodiments, the Proline Analog Compounds of Formulae I(a), I(b), II(a), II(b), III(a), and III(b), are those wherein X is S.

In certain embodiments, the Proline Analog Compounds of Formulae I(a), I(b), II(a), II(b), III(a), and III(b), are those wherein X is O.

In certain embodiments, the Proline Analog Compounds of Formulae I(a), I(b), II(a), II(b), III(a), and III(b) are those wherein R¹ is —(C₁-C₁₀ alkyl), —O(C₁-C₁₀ alkyl), —NH(C₁-C₄ alkyl), —N(C₁-C₄ alkyl)₂,

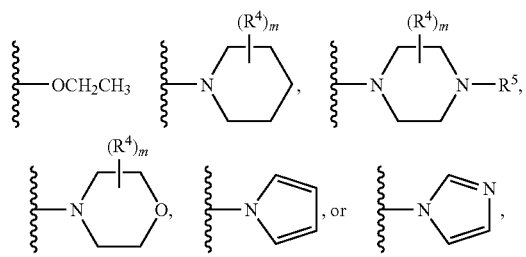

wherein m is an integer selected from the group consisting of 0, 1, 2, 3, and 4, and each $R^4$ is independently -halo, —C(halo)$_3$, —CH(halo)$_2$, —CH$_2$(halo), —OH, —(C$_1$-C$_4$ alkyl), or —O(C$_1$-C$_4$ alkyl), while $R^5$ is —H, —C(halo)$_3$, —CH(halo)$_2$, —CH$_2$(halo), —(C$_1$-C$_{10}$ alkyl), —(CH$_2$)$_r$O (C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4, and where each halo is independently —F, —Cl, —Br, or —I.

In certain embodiments, the Proline Analog Compounds of Formulae II(a), X and XI, are those wherein $R^9$ is —(C$_1$-C$_{10}$ alkyl), —NH(C$_1$-C$_4$ alkyl), —N(C$_1$-C$_4$ alkyl)$_2$,

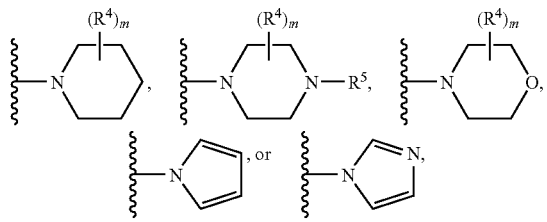

wherein m is an integer selected from the group consisting of 0, 1, 2, 3, and 4, and each $R^4$ is independently -halo, —C(halo)$_3$, —CH(halo)$_2$, —CH$_2$(halo), —OH, —(C$_1$-C$_4$ alkyl), or —O(C$_1$-C$_4$ alkyl), while $R^5$ is —H, —C(halo)$_3$, —CH(halo)$_2$, —CH$_2$(halo), —(C$_1$-C$_{10}$ alkyl), —(CH$_2$)$_r$O (C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4, and where each halo is independently —F, —Cl, —Br, or —I.

In certain embodiments, the Proline Analog Compounds of Formulae I(a), II(b), III(a), and III(b) are those wherein $R^1$ is

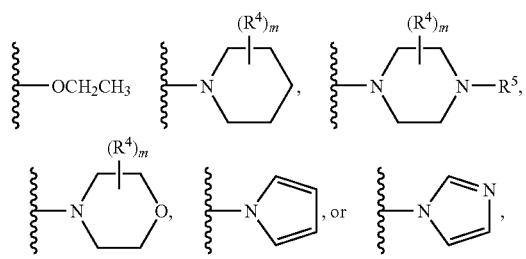

wherein m is an integer selected from the group consisting of 0, 1, 2, 3, and 4, and each $R^4$ is independently -halo, —C(halo)$_3$, —CH(halo)$_2$, —CH$_2$(halo), —OH, —(C$_1$-C$_4$ alkyl), or —O(C$_1$-C$_4$ alkyl), while $R^5$ is —H, —C(halo)$_3$, —CH(halo)$_2$, —CH$_2$(halo), —(C$_1$-C$_{10}$ alkyl), —(CH$_2$)$_r$O (C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4, and where each halo is independently —F, —Cl, —Br, or —I.

In certain embodiments, the Proline Analog Compounds of Formulae II(a), X and XI, are those wherein $R^9$ is

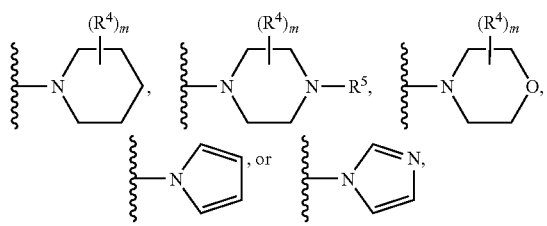

wherein m is an integer selected from the group consisting of 0, 1, 2, 3, and 4, and each $R^4$ is independently -halo, —C(halo)$_3$, —CH(halo)$_2$, —CH$_2$(halo), —OH, —(C$_1$-C$_4$ alkyl), or —O(C$_1$-C$_4$ alkyl), while $R^5$ is —H, —C(halo)$_3$, —CH(halo)$_2$, —CH$_2$(halo), —(C$_1$-C$_{10}$ alkyl), —(CH$_2$)$_r$O (C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4, and where each halo is independently —F, —Cl, —Br, or —I.

In certain embodiments, the Proline Analog Compounds of Formulae I(a), I(b), II(b), III(a), and III(b), are those wherein $R^1$ is

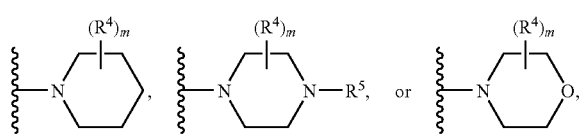

wherein m is 1, $R^4$ is -halo, —C(halo)$_3$, —CH(halo)$_2$, —CH$_2$(halo), —OH, —(C$_1$-C$_4$ alkyl), or —O(C$_1$-C$_4$ alkyl), and $R^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4, and where each halo is independently —F, —Cl, —Br, or —I.

In certain embodiments, the Proline Analog Compounds of Formulae II(a), X and XI, are those wherein $R^9$ is wherein m is 1 and $R^4$ is -halo, —C(halo)$_3$, —CH(halo)$_2$, —CH$_2$(halo), —OH, —(C$_1$-C$_4$ alkyl), or —O(C$_1$-C$_4$ alkyl), while $R^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4, and where each halo is independently —F, —Cl, —Br, or —I.

In certain embodiments, the Proline Analog Compounds of Formulae I(a), I(b), III(b), III(a), and III(b), are those wherein $R^1$ is wherein m is 1, $R^4$ is —OH or —O($C_1$-$C_4$ alkyl), and $R^5$ is —($C_1$-$C_{10}$ alkyl), —$CH_2NH(C_1$-$C_4$ alkyl), or —$CH_2N(C_1$-$C_4$ alkyl)$_2$.

In certain embodiments, the Proline Analog Compounds of Formulae II(a), X, and XI, are those wherein $R^9$ is

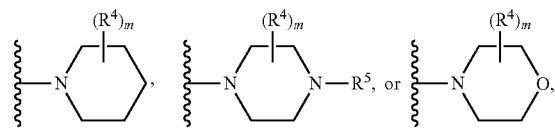

wherein m is 1, $R^4$ is —OH or —O($C_1$-$C_4$ alkyl), and $R^5$ is —($C_1$-$C_{10}$ alkyl), —$CH_2NH(C_1$-$C_4$ alkyl), or —$CH_2N(C_1$-$C_4$ alkyl)$_2$.

In certain embodiments, the Proline Analog Compounds of Formulae I(a), I(b), II(b), I(a), and II(b), are those wherein $R^1$ is

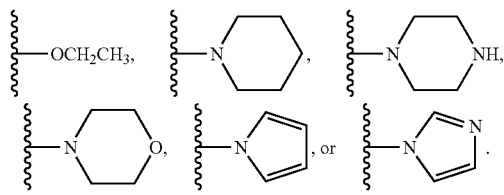

In certain embodiments, the Proline Analog Compounds of Formulae II(a), X, and XI, are those wherein $R^9$ is

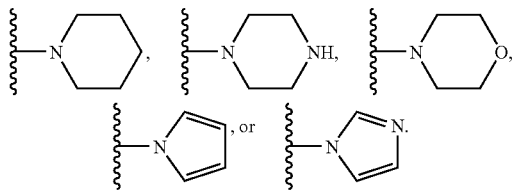

In certain embodiments, the Proline Analog Compounds of Formulae I(a), I(b), II(b), III(a), and III(b), are those wherein $R^1$ is

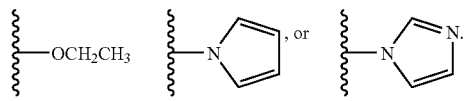

In certain embodiments, the Proline Analog Compounds of Formulae II(a), X and A, are those wherein $R^9$ is

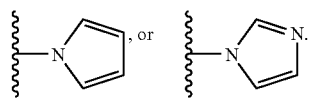

In certain embodiments, the Proline Analog Compounds of Formulae I(a), I(b), II(b), III(a), and III(b) are those wherein $R^1$ is —($C_1$-$C_{10}$ alkyl), —O($C_1$-$C_{10}$ alkyl), —NH($C_1$-$C_4$ alkyl), or —N($C_1$-$C_4$ alkyl)$_2$.

In certain embodiments, the Proline Analog Compounds of Formulae I(a), I(b), II(b), III(a), and III(b), are those wherein $R^1$ is —($C_1$-$C_{10}$ alkyl)

In certain embodiments, the Proline Analog Compounds of Formulae I(a), I(b), II(b), III(a), and III(b), are those wherein $R^1$ is —($C_1$-$C_6$ alkyl).

In certain embodiments, the Proline Analog Compounds of Formulae I(a), I(b), II(b), III(a), and III(b), are those wherein $R^1$ is lower alkyl.

In certain embodiments, the Proline Analog Compounds of Formulae I(a), I(b), II(b), III(a), and III(b), are those wherein $R^1$ is —($C_1$-$C_4$ alkyl).

In certain embodiments, the Proline Analog Compounds of Formulae I(a), I(b), II(b), III(a), and III(b), are those wherein $R^1$ is —($C_1$-$C_3$ alkyl).

In certain embodiments, the Proline Analog Compounds of Formulae II(a), X and XI, are those wherein $R^9$ is —($C_1$-$C_{10}$ alkyl), —NH($C_1$-$C_4$ alkyl), or —N($C_1$-$C_4$ alkyl)$_2$.

In certain embodiments, the Proline Analog Compounds of Formulae II(a), X and XI, are those wherein $R^9$ is —($C_1$-$C_{10}$ alkyl)

In certain embodiments, the Proline Analog Compounds of Formulae II(a), X and XI, are those wherein $R^9$ is —($C_1$-$C_6$ alkyl).

In certain embodiments the Proline Analog Compounds of Formulae II(a), X and A, are those wherein $R^9$ is lower alkyl.

In certain embodiments, the Proline Analog Compounds of Formulae II(a), X and XI, are those wherein $R^9$ is —($C_1$-$C_4$ alkyl).

In certain embodiments, the Proline Analog Compounds of Formulae II(a), X and M, are those wherein $R^9$ is —($C_1$-$C_3$ alkyl).

In certain embodiments, the Proline Analog Compounds of Formulae I(a), I(b), II(a), II(b), III(a), III(b), X and A, are those wherein $R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups, wherein each $R^3$ is independently -halo, —C(halo)$_3$, —CH$_2$(halo)$_2$, —C(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH, —CONH($C_1$-$C_4$ alkyl), or —CON($C_1$-$C_4$ alkyl)$_2$.

In certain embodiments, the Proline Analog Compounds of Formulae I(a), I(b), II(a), II(b), III(a), III(b), X and AU, are those wherein $R^2$ is

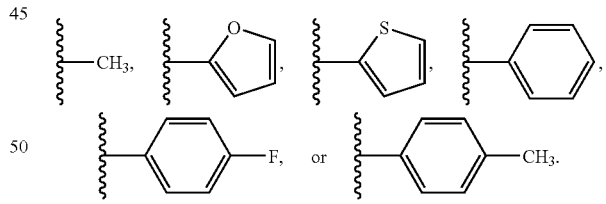

In certain embodiments, the Proline Analog Compounds of Formulae I(a), I(b), II(a), II(b), III(a), III(b), X and XI, are those wherein $R^2$ is

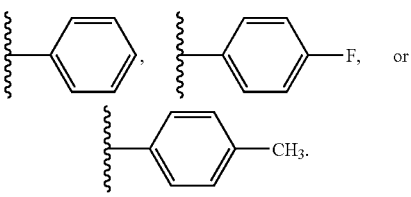

In certain embodiments, the Proline Analog Compounds of Formulae I(a), I(b), II(a), II(b), III(a), II(b), X and XI, are those wherein $R^2$ is —($C_1$-$C_{10}$ alkyl).

In certain embodiments, the Proline Analog Compounds of Formulae I(a), I(b), II(a), II(b), III(a), II(b), X and XI, are those wherein $R^2$ is —($C_1$-$C_6$ alkyl).

In certain embodiments, the Proline Analog Compounds of Formulae I(a), I(b), II(a), II(b), II(a), III(b), X and XI, are those wherein $R^2$ is lower alkyl.

In certain embodiments, the Proline Analog Compounds of Formulae I(a), I(b), II(a), II(b), III(a), III(b), X and XI, are those wherein $R^2$ is —($C_1$-$C_4$ alkyl).

In certain embodiments, the Proline Analog Compounds of Formulae I(a), I(b), II(a), II(b), III(a), II(b), X and XI, are those wherein $R^2$ is —($C_1$-$C_3$ alkyl).

In certain embodiments, the Proline Analog Compounds of Formulae I(b), III(a), and III(b) are those wherein n is 1, 2, or 3.

In certain embodiments, the Proline Analog Compounds of Formulae I(b), III(a), and III(b) are those wherein n is 2.

In certain embodiments, the Proline Analog Compounds of Formulae I(a), are those wherein k is 2 or 3.

In certain embodiments, the Proline Analog Compounds of Formulae I(a), are those wherein k is 2.

In certain embodiments, the Proline Analog Compounds of Formula X are those in which p is 1, 2, or 3.

In certain embodiments, the Proline Analog Compounds of Formula X are those in which p is 2.

In one embodiment the compound is a compound of formula II(a) provided that when X is S, $R^6$ is —H, $R^7$ is —H, and $R^9$ is —NH($C_1$-$C_4$)alkyl, then $R^2$ is not thienyl.

In one embodiment the compound is a compound of formula X provided that when $R^2$ is phenyl substituted with one —O($C_1$-$C_4$ alkyl), then $R^9$ is not —$CH_3$.

In certain embodiments, the Proline Analog Compounds of Formulae II(a), II(b), and XI, are those wherein $R^6$ and $R^7$ are each independently H, —($C_1$-$C_{10}$ alkyl), —$CH_2$O($C_1$-$C_4$ alkyl), —$CH_2$NH($C_1$-$C_4$ alkyl), —$CH_2$N($C_1$-$C_4$ alkyl)$_2$, or —($C_3$-$C_8$)cycloalkyl either unsubstituted or substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —$NH_2$, —NH($C_1$-$C_4$ alkyl), —N($C_1$-$C_4$ alkyl), —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae II(a), II(b), and XI, are those wherein $R^6$ and $R^7$ are each independently H, or —($C_1$-$C_{10}$ alkyl) either unsubstituted or substituted with 1, 2, or 3 $R^3$ groups, wherein each $R^3$ is independently -halo, —CN, —OH, —$NO_2$, —$NH_2$, —NH($C_1$-$C_4$ alkyl), or —N($C_1$-$C_4$ alkyl)$_2$.

In certain embodiments, the Proline Analog Compounds of Formulae II(a), II(b), and XI, are those wherein each $R^6$ and $R^7$ is independently phenyl either unsubstituted or substituted with one 1, 2, or 3 $R^3$ groups, or -(5 to 7 membered)heteroaryl either unsubstituted or substituted with 1, 2, or 3 $R^3$ groups, wherein each $R^3$ is independently -halo, —C(halo)$_3$, —CH(halo)$_2$, —C(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —CON, —CONH($C_1$-$C_4$ alkyl), or —CON($C_1$-$C_4$ alkyl)$_2$.

In certain embodiments, the Proline Analog Compounds of Formulae II(a), II(b), and XI, are those wherein $R^6$ and $R^7$ are taken together with the carbon atoms to which they are attached form a -(5 to 7 membered)heteroaryl ring optionally substituted with 1, 2, or 3 $R^3$ groups, wherein each $R^3$ is independently halo, —C(halo)$_3$, —CH(halo)$_2$, —$CH_2$(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae II(a), II(b), and XI, are those wherein $R^6$ and $R^7$ are taken together with the carbon atoms to which they are attached form an aromatic six-membered carbocyclic ring optionally substituted with 1, 2, or 3 $R^3$ groups, wherein each $R^3$ is independently -halo, —C(halo)$_3$, —CH(halo)$_2$, —$CH_4$(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In one embodiment, the Proline Analog Compounds of Formula IV(a) and IV(b) are those wherein $R^1$ is

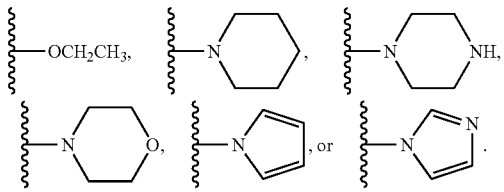

In one embodiment, the Proline Analog Compounds of Formula IV(a) and IV(b) are those wherein $R^1$ is

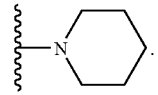

In one embodiment, the Proline Analog Compounds of Formula IV(a) and IV(b) are those wherein $R^1$ is —($C_1$-$C_{10}$ alkyl), —O($C_1$-$C_{10}$ alkyl), —NH($C_1$-$C_4$ alkyl), or —N($C_1$-$C_4$ alkyl)$_2$.

In one embodiment, the Proline Analog Compounds of Formula IV(a) and IV(b) are those wherein $R^1$ is —($C_1$-$C_{10}$ alkyl) or —O($C_1$-$C_{10}$ alkyl).

In one embodiment, the Proline Analog Compounds of Formula IV(a) and IV(b) are those wherein $R^1$ is —($C_1$-$C_{10}$ alkyl).

In one embodiment, the Proline Analog Compounds of Formula IV(a) and W(b) are those wherein $R^1$ is —($C_1$-$C_6$ alkyl).

In one embodiment, the Proline Analog Compounds of Formula IV(a) and IV(b) are those wherein $R^1$ is lower alkyl.

In one embodiment, the Proline Analog Compounds of Formula IV(a) and IV(b) are those wherein $R^1$ is —($C_1$-$C_4$ alkyl).

In one embodiment, the Proline Analog Compounds of Formula IV(a) and IV(b) are those wherein $R^1$ is —($C_1$-$C_3$ alkyl).

In one embodiment, the Proline Analog Compounds of Formula IV(a) and IV(b) are those wherein $R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups, wherein each $R^3$ is independently -halo, —C(halo)$_3$, —C(halo)$_2$, -(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In one embodiment, the Proline Analog Compounds of Formula IV(a) and IV(b) are those wherein $R^1$ is

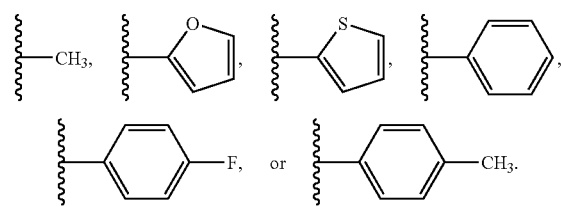

In one embodiment, the Proline Analog Compounds of Formula IV(a) and IV(b) are those wherein $R^2$ is

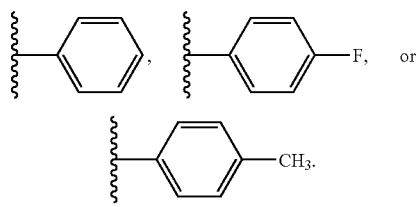

In one embodiment, the Proline Analog Compounds of Formula IV(a) and IV(b) are those wherein $R^2$ is —($C_1$-$C_{10}$ alkyl).

In one embodiment, the Proline Analog Compounds of Formula IV(a) and IV(b) are those wherein $R^2$ is —($C_1$-$C_6$ alkyl).

In one embodiment, the Proline Analog Compounds of Formula IV(a) and IV(b) are those wherein $R^2$ is lower alkyl.

In one embodiment, the Proline Analog Compounds of Formula IV(a) and IV(b) are those wherein $R^2$ is —($C_1$-$C_4$ alkyl).

In one embodiment, the Proline Analog Compounds of Formula IV(a) and IV(b) are those wherein $R^2$ is —($C_1$-$C_3$ alkyl).

In one embodiment, the Proline Analog Compounds of Formula IV(a) are those wherein k=2 or 3.

In one embodiment, the Proline Analog Compounds of Formula IV(a) are those wherein k=2.

In one embodiment, the Proline Analog Compounds of Formula IV(b) are those wherein n=1, 2, or 3.

In one embodiment, the Proline Analog Compounds of Formula IV(b) are those wherein n=2.

In one embodiment, the Proline Analog Compounds of Formula V(a) and Vi) are those wherein $R^1$ is

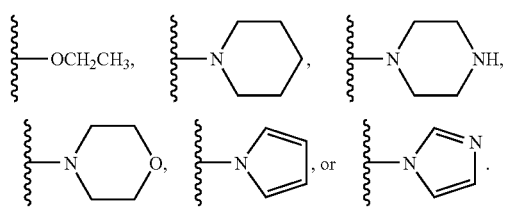

In one embodiment, the Proline Analog Compounds of Formula V(a) and V(b) are those wherein $R^1$ is

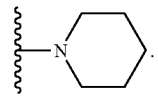

In one embodiment, the Proline Analog Compounds of Formula V(a) and V(b) are those wherein $R^1$ is —($C_1$-$C_{10}$ alkyl), —O($C_1$-$C_{10}$ alkyl), —NH($C_1$-$C_4$ alkyl), or —N($C_1$-$C_4$ alkyl)$_2$.

In one embodiment, the Proline Analog Compounds of Formula V(a) and V(b) are those wherein $R^1$ is —($C_1$-$C_{10}$ alkyl) or —O($C_1$-$C_{10}$ alkyl).

In one embodiment, the Proline Analog Compounds of Formula V(a) and V(b) are those wherein $R^1$ is —($C_1$-$C_{11}$ alkyl).

In one embodiment, the Proline Analog Compounds of Formula V(a) and V(b) are those wherein $R^1$ is —($C_1$-$C_6$ alkyl).

In one embodiment, the Proline Analog Compounds of Formula V(a) and V(b) are those wherein $R^1$ is lower alkyl.

In one embodiment, the Proline Analog Compounds of Formula V(a) and IV(b) are those wherein $R^1$ is —($C_1$-$C_4$ alkyl).

In one embodiment, the Proline Analog Compounds of Formula V(a) and V(b) are those wherein $R^1$ is —($C_1$-$C_3$ alkyl).

In one embodiment, the Proline Analog Compounds of Formula V(a) and V(b) are those wherein $R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups, wherein each $R^3$ is independently -halo, —C(halo)$_3$, —CH(halo)$_2$, —CH$_2$(halo), —CN, —OH, —NO$_2$, —N, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$.

In one embodiment, the Proline Analog Compounds of Formula V(a) and V(b) are those wherein $R^2$ is

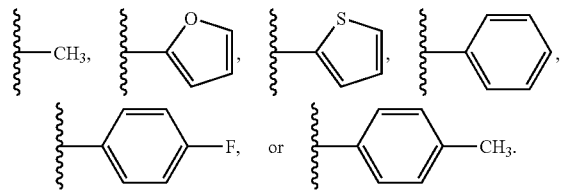

In one embodiment, the Proline Analog Compounds of Formula V(a) and V(b) are those wherein $R^2$ is

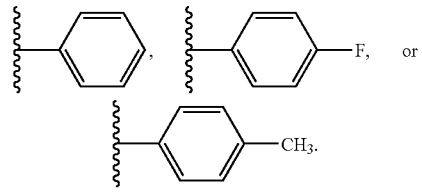

In one embodiment, the Proline Analog Compounds of Formula V(a) and V(b) are those wherein $R^2$ is —($C_1$-$C_{10}$ alkyl).

In one embodiment, the Proline Analog Compounds of Formula V(a) and V(b) are those wherein R² is —(C₁-C₆ alkyl).

In one embodiment, the Proline Analog Compounds of Formula V(a) and Vi) are those wherein R² is lower alkyl.

In one embodiment, the Proline Analog Compounds of Formula V(a) and V(b) are those wherein R² is —(C₁-C₄ alkyl).

In one embodiment, the Proline Analog Compounds of Formula V(a) and V(b) are those wherein R² is —(C₁-C₃ alkyl).

In one embodiment, the Proline Analog Compounds of Formula V(a) and V(b) are those wherein n=1, 2, or 3.

In one embodiment, the Proline Analog Compounds of Formula V(a) and V(b) are those wherein n=2.

In one embodiment, the Proline Analog Compounds of Formula V(a) are those wherein R⁹ is

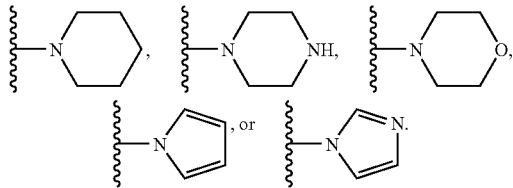

In one embodiment, the Proline Analog Compounds of Formula VI(a) are those wherein R⁹ is

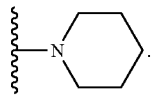

In one embodiment, the Proline Analog Compounds of Formula VI(a) are those wherein R⁹ is —(C₁-C₁₀ alkyl), —NH(C₁-C₄ alkyl), or —N(C₁-C₄ alkyl)₂.

In one embodiment, the Proline Analog Compounds of Formula VI(a) are those wherein R⁹ is —(C₁-C₁₀ alkyl).

In one embodiment, the Proline Analog Compounds of Formula VI(a) are those wherein R⁹ is —(C₁-C₆ alkyl).

In one embodiment, the Proline Analog Compounds of Formula VI(a) are those wherein R⁹ is lower alkyl.

In one embodiment, the Proline Analog Compounds of Formula VI(a) are those wherein R⁹ is —(C₁-C₄ alkyl).

In one embodiment, the Proline Analog Compounds of Formula VI(a) are those wherein R⁹ is —(C₁-C₃ alkyl).

In one embodiment, the Proline Analog Compounds of Formula VI(a) are those wherein R⁹ is —(C₁-C₁₀ alkyl), —(C₃-C₈) cycloalkyl, phenyl, naphthyl, anthryl, phenanthryl, or -(5 to 7 membered) heteroaryl, each being unsubstituted or substituted with 1, 2, or 3 R³ groups, wherein each R³ is independently -halo, —C(halo)₃, —CH(halo)₂, —C(halo), —CN, —OH, —NO₂, —NH₂, —NH(C₁-C₄ alkyl), —N(C₁-C₄ alkyl)₂, —(C₁-C₁₀ alkyl), —O(C₁-C₄ alkyl), —CONH₂, —CONH(C₁-C₄ alkyl), or —CON(C₁-C₄ alkyl)₂.

In one embodiment, the Proline Analog Compounds of Formula VI (b) and VIII (b) are those wherein R¹ is

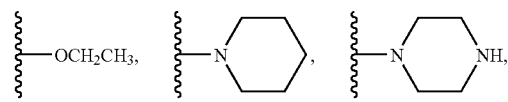

In one embodiment, the Proline Analog Compounds of Formula VI (b) and VIII (b) are those wherein R¹ is

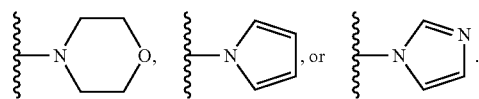

In one embodiment, the Proline Analog Compounds of Formula VI (b) and VIII (b) are those wherein R¹ is

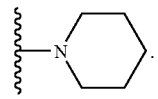

In one embodiment, the Proline Analog Compounds of Formula VI (b) and VIII (b) are those wherein R¹ is —(C₁-C₁₀ alkyl), —O(C₁-C₁₀ alkyl), —NH(C₁-C₄ alkyl), or —N(C₁-C₄ alkyl)₂.

In one embodiment, the Proline Analog Compounds of Formula VI (b) and VIII (b) are those wherein R¹ is —(C₁-C₁₀ alkyl) or —O(C₁-C₁₀ alkyl).

In one embodiment, the Proline Analog Compounds of Formula VI (b) and VIII ) are those wherein R¹ is —(C₁-C₁₁ alkyl).

In one embodiment, the Proline Analog Compounds of Formula VI (b) and VIII (b) are those wherein R¹ is —(C₁-C₆ alkyl).

In one embodiment, the Proline Analog Compounds of Formula VI (b) and VIII (b) are those wherein R¹ is lower alkyl.

In one embodiment, the Proline Analog Compounds of Formula VI (b) and VIII (b) are those wherein R¹ is —(C₁-C₄ alkyl).

In one embodiment, the Proline Analog Compounds of Formula VI (b) and VIII (b) are those wherein R¹ is —(C₁-C₃ alkyl).

In one embodiment, the Proline Analog Compounds of Formula VI (a) and VI (b) are those wherein R² is —(C₁-C₁₀ alkyl), —(C₃-C₈) cycloalkyl, phenyl, naphthyl, anthryl, phenanthryl, or -(5 to 7 membered) heteroaryl, each being unsubstituted or substituted with 1, 2, or 3 R³ groups, wherein each R³ is independently -halo, —C(halo)₃, —CH(halo)₂, —CH₂(halo), —CN, —OH, —NO₂, —NH₂, —NH(C₁-C₄ alkyl), —N(C₁-C₄ alkyl)₂, —(C₁-C₁₀ alkyl), —O(C₁-C₄ alkyl), —CONH₂, —CONH(C₁-C₄ alkyl), or —CON(C₁-C₄ alkyl)₂.

In one embodiment, the Proline Analog Compounds of Formula VI (a) and VI (b) are those wherein R² is

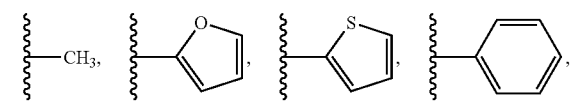

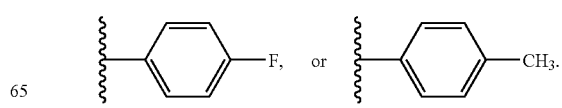

In one embodiment, the Proline Analog Compounds of Formula VI (a) and VI (b) are those wherein $R^2$ is

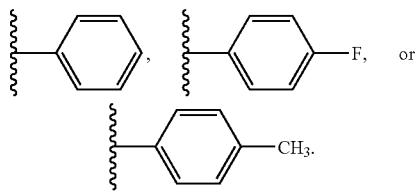

In one embodiment, the Proline Analog Compounds of Formula VI (a) and VI (b) are those wherein $R^1$ is —($C_1$-$C_{10}$ alkyl).

In one embodiment, the Proline Analog Compounds of Formula VI (a) and VI (b) are those wherein $R^2$ is —($C_1$-$C_6$ alkyl).

In one embodiment, the Proline Analog Compounds of Formula VI (a) and VI (b) are those wherein $R^2$ is lower alkyl.

In one embodiment, the Proline Analog Compounds of Formula VI (a) and VI (b) are those wherein $R^2$ is —($C_1$-$C_4$ alkyl).

In one embodiment, the Proline Analog Compounds of Formula VI (a) and VI (b) are those wherein $R^2$ is —($C_1$-$C_3$ alkyl).

In certain embodiments, the Proline Analog Compounds of Formulae VI(a) and VI (b) are those wherein $R^6$ and $R^7$ are each independently H, —($C_1$-$C_{10}$ alkyl), —$CH_2O$($C_1$-$C_4$ alkyl), —CH($C_1$-$C_4$ alkyl), —$CH_2N$($C_1$-$C_4$ alkyl)$_2$, or —($C_3$-$C_8$)cycloalkyl either unsubstituted or substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH ($C_1$-$C_4$ alkyl), or —CON($C_1$-$C_4$ alkyl)$_2$.

In certain embodiments, the Proline Analog Compounds of Formulae VI(a) and VI (b) are those wherein $R^6$ and $R^7$ are each independently H, or —($C_1$-$C_{10}$ alkyl) either unsubstituted or substituted with 1, 2, or 3 $R^3$ groups, wherein each $R^3$ is independently -halo, —CN, —OH, —$NO_2$, —NH, —NH ($C_1$-$C_4$ alkyl), or —N($C_1$-$C_4$ alkyl)$_2$.

In certain embodiments, the Proline Analog Compounds of Formulae VI(a) and VI (b) are those wherein each $R^6$ and $R^7$ is independently phenyl either unsubstituted or substituted with 1, 2, or 3 $R^3$ groups, or -(5 to 7 membered)heteroaryl either unsubstituted or substituted with 1, 2, or 3 $R^3$ groups, wherein each $R^3$ is independently -halo, —C(halo)$_2$, —CH(halo)$_2$, —$CH_2$(halo), —CN, —OH, —NO, —NH, —NH ($C_1$-$C_4$ alkyl), —N($C_1$-$C_4$ alkyl), —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae VI(a) and VI (b) are those wherein $R^6$ and $R^7$ are taken together with the carbon atoms to which they are attached to form a -(5 to 7 membered)heteroaryl ring optionally substituted with 1, 2, or 3 $R^3$ groups, wherein each $R^3$ is independently -halo, —C(halo)$_3$, —CH(halo)$_2$, —CH(halo), —CN, —OH, —$NO_2$, —$NH_2$, —NH($C_1$-$C_4$ alkyl), —N($C_1$-$C_4$ alkyl)$_2$, —($C_1$-$C_4$, alkyl)$_2$, —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae VI(a) and VI (b) are those wherein $R^6$ and $R^7$ are taken together with the carbon atoms to which they are attached to form an aromatic six-membered carbocyclic ring optionally substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —NH, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In one embodiment, the Proline Analog Compounds of Formula VII (a) and VII (b) are those wherein $R^1$ is

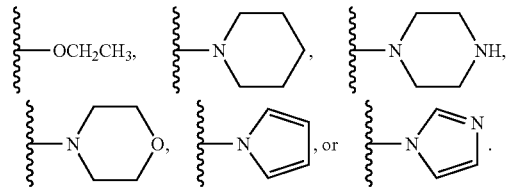

In one embodiment, the Proline Analog Compounds of Formula VII (a) and VII (b) are those wherein $R^1$ is

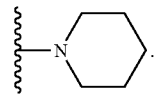

In one embodiment, the Proline Analog Compounds of Formula VII (a) and VII (b) are those wherein $R^1$ is —($C_1$-$C_{10}$ alkyl), —O($C_1$-$C_{10}$ alkyl), —NH($C_1$-$C_4$ alkyl), or —N($C_1$-$C_4$ alkyl)$_2$.

In one embodiment, the Proline Analog Compounds of Formula VII (a) and VII (b) are those wherein $R^1$ is —($C_1$-$C_{10}$ alkyl) or —O($C_1$-$C_{10}$ alkyl).

In one embodiment, the Proline Analog Compounds of Formula VII (a) and VII (b) are those wherein $R^1$ is —($C_1$-$C_{10}$ alkyl).

In one embodiment, the Proline Analog Compounds of Formula VII (a) and VII (b) are those wherein $R^1$ is —($C_1$-$C_6$ alkyl).

In one embodiment, the Proline Analog Compounds of Formula VII (a) and VII (b) are those wherein $R^1$ is lower alkyl.

In one embodiment, the Proline Analog Compounds of Formula VII (a) and VII (b) are those wherein $R^1$ is —($C_1$-$C_4$ alkyl).

In one embodiment, the Proline Analog Compounds of Formula VII (a) and VII (b) are those wherein $R^1$ is —($C_1$-$C_3$ alkyl).

In one embodiment, the Proline Analog Compounds of Formula VII (a) and VII (b) are those wherein $R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups, wherein each $R^3$ is independently -halo, —C(halo)$_3$, —CH(halo)$_2$, —C(halo), —CN, —OH, —$NO_2$, —$NH_2$, —NH($C_1$-$C_4$ alkyl), —N($C_1$-$C_4$ alkyl), —($C_1$-$C_4$ alkyl), —O($C_1$-$C_4$ alkyl), —$CONH_2$, —CONH($C_1$-$C_4$ alkyl), or —CON($C_1$-$C_4$ alkyl)$_2$.

In one embodiment, the Proline Analog Compounds of Formula VII (a) and VII (b) are those wherein $R^2$ is

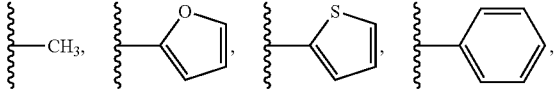

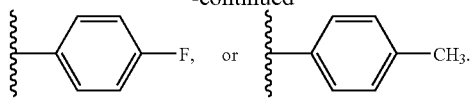

In one embodiment, the Proline Analog Compounds of Formula IX (a) and IX (b) are those wherein $R^2$ is

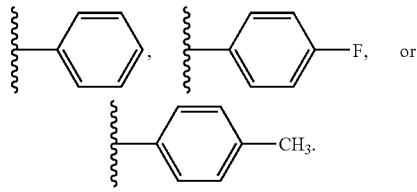

In one embodiment, the Proline Analog Compounds of Formula VII (a) and VII (b) are those wherein $R^2$ is —($C_1$-$C_{10}$ alkyl).

In one embodiment, the Proline Analog Compounds of Formula VII (a) and VII (b) are those wherein $R^2$ is —($C_1$-$C_6$ alkyl).

In one embodiment, the Proline Analog Compounds of Formula VII (a) and VII (b) are those wherein $R^2$ is lower alkyl.

In one embodiment, the Proline Analog Compounds of Formula VII (a) and VII (b) are those wherein $R^2$ is —($C_1$-$C_4$ alkyl).

In one embodiment, the Proline Analog Compounds of Formula VII (a) and VII (b) are those wherein $R^2$ is —($C_1$-$C_3$ alkyl).

In certain embodiments, the Proline Analog Compounds of Formulae VII (a) and VII (b) are those wherein $R^6$ and $R^7$ are each independently H, —($C_1$-$C_{10}$ alkyl), —$CH_2O$($C_1$-$C_4$ alkyl), —$CH_2NH$($C_1$-$C_4$ alkyl), —$CH_2N$($C_1$-$C_4$ alkyl)$_2$, or —($C_3$-$C_8$)cycloalkyl either unsubstituted or substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae VII (a) and VII (b) are those wherein $R^6$ and $R^7$ are each independently H, or —($C_1$-$C_{10}$ alkyl) either unsubstituted or substituted with 1, 2, or 3 $R^3$ groups, wherein each $R^3$ is independently -halo, —CN, —OH, —$NO_2$, —$NH_2$, —NH($C_1$-$C_4$ alkyl), or —N($C_1$-$C_4$ alkyl)$_2$.

In certain embodiments, the Proline Analog Compounds of Formulae VII (a) and VII (b) are those wherein each $R^6$ and $R^7$ is independently phenyl either unsubstituted or substituted with 1, 2 or 3 $R^3$ groups, or -(5 to 7 membered)heteroaryl either unsubstituted or substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae VII (a) and VII (b) are those wherein $R^6$ and $R^7$ are taken together with the carbon atoms to which they are attached to form a -(5 to 7 membered)heteroaryl ring optionally substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —NH, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In certain embodiments, the Proline Analog Compounds of Formulae VII (a) and VII (b) are those wherein $R^6$ and $R^7$ are taken together with the carbon atoms to which they are attached to form an aromatic six-membered carbocyclic ring optionally substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —$NH_2$, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In one embodiment, the Proline Analog Compounds of Formula VIII(a) and VIII (b) are those wherein $R^1$ is

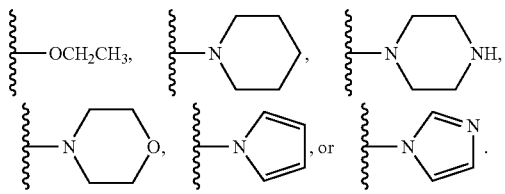

In one embodiment, the Proline Analog Compounds of Formula VIII (a) and VIII (b) are those wherein $R^1$ is

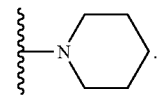

In one embodiment, the Proline Analog Compounds of Formula VIII (a) and VIII (b) are those wherein $R^1$ is —($C_1$-$C_{10}$ alkyl), —O($C_1$-$C_{10}$ alkyl), —NH($C_1$-$C_4$ alkyl), or —N($C_1$-$C_4$ alkyl)$_2$.

In one embodiment, the Proline Analog Compounds of Formula VIII (a) and VIII (b) are those wherein $R^1$ is —($C_1$-$C_{10}$ alkyl) or —O($C_1$-$C_{10}$ alkyl).

In one embodiment, the Proline Analog Compounds of Formula VIII (a) and VIII (b) are those wherein $R^1$ is —($C_1$-$C_{10}$ alkyl).

In one embodiment, the Proline Analog Compounds of Formula VIII (a) and VIII (b) are those wherein $R^1$ is —($C_1$-$C_6$ alkyl).

In one embodiment, the Proline Analog Compounds of Formula VIII (a) and VIII (b) are those wherein $R^1$ is lower alkyl.

In one embodiment, the Proline Analog Compounds of Formula VIII (a) and VIII (b) are those wherein $R^1$ is —($C_1$-$C_4$ alkyl).

In one embodiment, the Proline Analog Compounds of Formula VIII (a) and VIII (b) are those wherein $R^1$ is —($C_1$-$C_4$ alkyl).

In one embodiment, the Proline Analog Compounds of Formula VIII (a) and VIII (b) are those wherein $R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups, wherein each $R^3$ is independently -halo, —C(halo)$_3$, —CH(halo)$_2$, —$CH_2$(halo), —CN, —OH, —$NO_2$, —NH, —NH($C_1$-$C_4$ alkyl), —N($C_1$-$C_4$ alkyl)$_2$, —($C_1$-$C_{10}$ alkyl), —O($C_1$-$C_4$ alkyl), —$CONH_2$, —CONH($C_1$-$C_4$ alkyl), or —CON($C_1$-$C_4$ alkyl)$_2$.

In one embodiment, the Proline Analog Compounds of Formula VIII (a) and VIII (b) are those wherein $R^2$ is

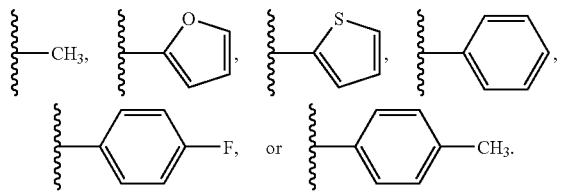

In one embodiment, the Proline Analog Compounds of Formula VIII (a) and VIII (b) are those wherein $R^2$ is

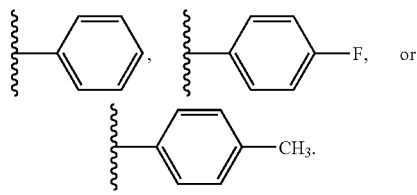

In one embodiment, the Proline Analog Compounds of Formula VIII (a) and VIII (b) are those wherein $R^2$ is —($C_1$-$C_{10}$ alkyl).

In one embodiment, the Proline Analog Compounds of Formula VIII (a) and VIII (b) are those wherein $R^2$ is —($C_1$-$C_6$ alkyl).

In one embodiment, the Proline Analog Compounds of Formula VIII (a) and VIII (b) are those wherein $R^2$ is lower alkyl.

In one embodiment, the Proline Analog Compounds of Formula VIII (a) and VIII (b) are those wherein $R^2$ is —($C_1$-$C_4$ alkyl).

In one embodiment, the Proline Analog Compounds of Formula VIII (a) and VIII (b) are those wherein $R^2$ is —($C_1$-$C_3$ alkyl).

In one embodiment, the Proline Analog Compounds of Formula VIII (a) and VIII (b) are those wherein n=1, 2, or 3.

In one embodiment, the Proline Analog Compounds of Formula VIII (a) and VIII (b) are those wherein n=2.

In one embodiment, the Proline Analog Compounds of Formula IX (a) and IX (b) are those wherein $R^1$ is

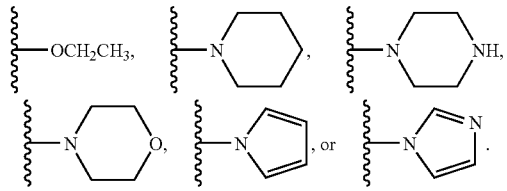

In one embodiment, the Proline Analog Compounds of Formula IX (a) and IX (b) are those wherein $R^1$ is

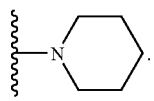

In one embodiment, the Proline Analog Compounds of Formula IX (a) and IX (b) are those wherein $R^1$ is —($C_1$-$C_{10}$ alkyl), —O($C_1$-$C_{10}$ alkyl), —NH($C_1$-$C_4$ alkyl), or —N($C_1$-$C_4$ alkyl)$_2$.

In one embodiment, the Proline Analog Compounds of Formula IX (a) and IX (b) are those wherein $R^1$ is —($C_1$-$C_{10}$ alkyl) or —O($C_1$-$C_{10}$ alkyl).

In one embodiment, the Proline Analog Compounds of Formula IX (a) and IX (b) are those wherein $R^1$ is —($C_1$-$C_{11}$ alkyl).

In one embodiment, the Proline Analog Compounds of Formula IX (a) and IX (b) are those wherein $R^1$ is —($C_1$-$C_6$ alkyl).

In one embodiment, the Proline Analog Compounds of Formula IX (a) and IX (b) are those wherein $R^1$ is lower alkyl.

In one embodiment, the Proline Analog Compounds of Formula IX (a) and IX (b) are those wherein $R^1$ is —($C_1$-$C_4$ alkyl).

In one embodiment, the Proline Analog Compounds of Formula IX (a) and IX (b) are those wherein $R^1$ is —($C_1$-$C_3$ alkyl).

In one embodiment, the Proline Analog Compounds of Formula IX (a) and IX (b) are those wherein $R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups, wherein each $R^3$ is independently -halo, —C(halo)$_3$, —CH(halo)$_2$, —CH$_2$(halo), —CN, —OH, —NO$_2$, —NH, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$.

In one embodiment, the Proline Analog Compounds of Formula IX (a) and IX (b) are those wherein $R^2$ is

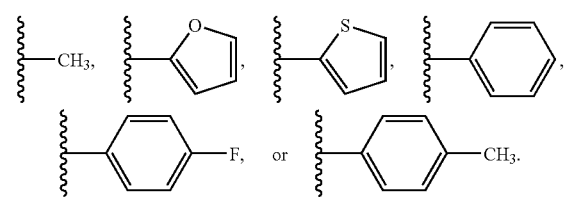

In one embodiment, the Proline Analog Compounds of Formula IX (a) and IX (b) are those wherein $R^2$ is

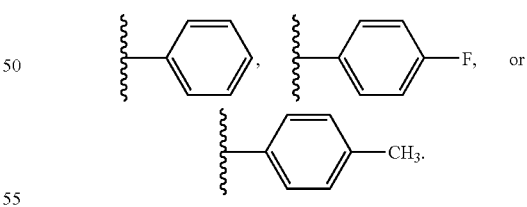

In one embodiment, the Proline Analog Compounds of Formula IX (a) and IX (b) are those wherein $R^2$ is —($C_1$-$C_{10}$ alkyl).

In one embodiment, the Proline Analog Compounds of Formula IX (a) and IX (b) are those wherein $R^2$ is —($C_1$-$C_6$ alkyl).

In one embodiment, the Proline Analog Compounds of Formula IX (a) and IX (b) are those wherein $R^2$ is lower alkyl.

In one embodiment, the Proline Analog Compounds of Formula IX (a) and IX (b) are those wherein $R^2$ is —($C_1$-$C_4$ alkyl).

In one embodiment, the Proline Analog Compounds of Formula IX (a) and IX (b) are those wherein $R^2$ is —($C_1$-$C_3$ alkyl).

In one embodiment, the Proline Analog Compounds of Formula IX (a) and IX (b) are those wherein n=1, 2, or 3.

In one embodiment, the Proline Analog Compounds of Formula IX (a) and IX (b) are those wherein n=2.

Particular embodiments of Proline Analog Compounds of the present disclosure are provided in the following 39 enumerated paragraphs:

1. A compound of formula I(a):

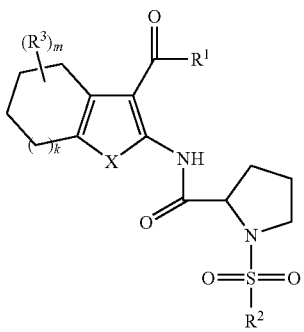

or a pharmaceutically acceptable salt or solvate thereof, wherein:
X is S or O;
$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

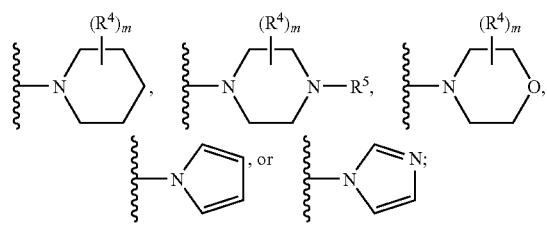

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups;
each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_6$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;
each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);
$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;
each halo is independently —F, —Cl, —Br, or —I;
k is an integer selected from the group consisting of 2, 3, and 4; and
each m is independently an integer selected from the group consisting of 0, 1, 2, 3, and 4.

2. A compound of formula I(b):

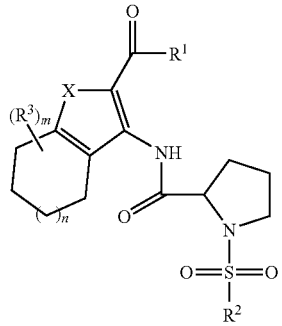

or a pharmaceutically acceptable salt or solvate thereof, wherein:
X is S or O;
$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

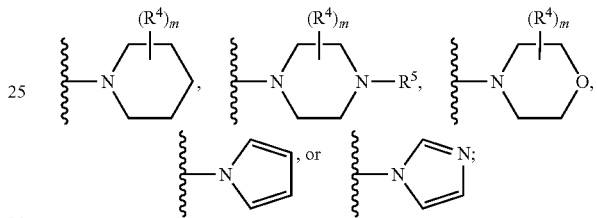

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups;
each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;
each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);
$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;
each halo is independently —F, —Cl, —Br, or —I;
n is an integer selected from the group consisting of 0, 1, 2, 3, and 4; and
each m is independently an integer selected from the group consisting of 0, 1, 2, 3, and 4.

3. A compound of formula III(a):

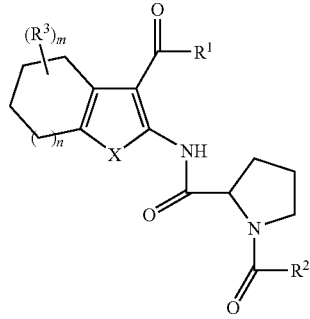

or a pharmaceutically acceptable salt or solvate thereof, wherein:

X is S or O;

R$^1$ is —(C$_1$-C$_{10}$ alkyl), —O(C$_1$-C$_{10}$ alkyl), —NH(C$_1$-C$_4$ alkyl), —N(C$_1$-C$_4$ alkyl)$_2$,

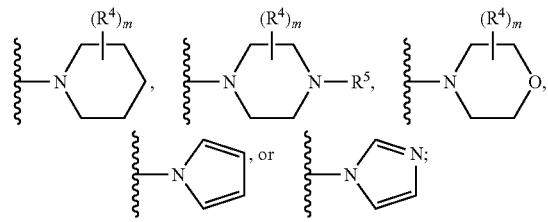

R$^2$ is —(C$_1$-C$_{10}$ alkyl), —(C$_3$-C$_8$) cycloakyl, phenyl, naphthyl, anthryl, phenanthryl, or -(5 to 7 membered) heteroaryl, each being unsubstituted or substituted with 1, 2, or 3 R$^3$ groups;

each R$^3$ is independently -halo, —C(halo)$_3$, —CH(halo)$_2$, —CH$_2$(halo), —CN, —OH, —NO$_2$, —NH$_2$, —NH(C$_1$-C$_4$ alkyl), —N(C$_1$-C$_4$ alkyl)$_2$, —(C$_1$-C$_{10}$ alkyl), —O(C$_1$-C$_4$ alkyl), —CONH$_2$, —CONH(C$_1$-C$_4$ alkyl), or —CON(C$_1$-C$_4$ alkyl)$_2$;

each R$^4$ is independently -halo, —C(halo)$_3$, —CH(halo)$_2$, —CH$_2$(halo), —OH, —(C$_1$-C$_4$ alkyl), or —O(C$_1$-C$_4$ alkyl);

R$^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4;

each halo is independently —F, —Cl, —Br, or —I;

n is an integer selected from the group consisting of 0, 1, 2, 3, and 4; and each m is independently an integer selected from the group consisting of 0, 1, 2, 3, and 4.

4. A compound of formula III(b):

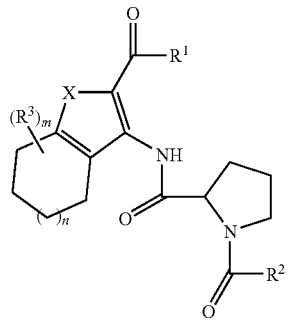

or a pharmaceutically acceptable salt or solvate thereof, wherein:

X is S or O;

R$^1$ is —(C$_1$-C$_{10}$ alkyl), —O(C$_1$-C$_{10}$ alkyl), —NH(C$_1$-C$_4$ alkyl), —N(C$_1$-C$_4$ alkyl)$_2$,

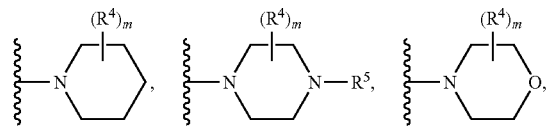

R$^2$ is —(C$_1$-C$_{10}$ alkyl), —(C$_3$-C$_8$) cycloakyl, phenyl, napthyl, anthryl, phenanthryl, or -(5 to 7 membered) heteroaryl, each being unsubstituted or substituted with 1, 2, or 3 R$^3$ groups;

each R$^3$ is independently -halo, —C(halo)$_3$, —CH(halo)$_2$, —CH$_2$(halo), —CN, —OH, —NO$_2$, —NH$_2$, —NH(C$_1$-C$_4$ alkyl), —N(C$_1$-C$_4$ alkyl)$_2$, —(C$_1$-C$_{10}$ alkyl), —O(C$_1$-C$_4$ alkyl), —CONH$_2$, —CONH(C$_1$-C$_4$ alkyl), or —CON(C$_1$-C$_4$ alkyl)$_2$;

each R$^4$ is independently -halo, —C(halo)$_3$, —CH(halo)$_2$, —CH$_2$(halo), —OH, —(C$_1$-C$_4$ alkyl), or —O(C$_1$-C$_4$ alkyl);

R$^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4;

each halo is independently —F, —Cl, —Br, or —I;

n is an integer selected from the group consisting of 0, 1, 2, 3, and 4; and each m is independently is an integer selected from the group consisting of 0, 1, 2, 3, and 4.

5. A compound of formula II(a):

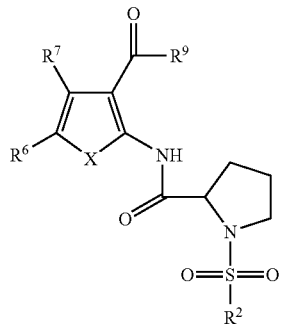

or a pharmaceutically acceptable salt or solvate thereof, wherein:

X is S or O;

R$^9$ is —(C$_1$-C$_{10}$ alkyl), —NH(C$_1$-C$_4$ alkyl), —N(C$_1$-C$_4$ alkyl)$_2$,

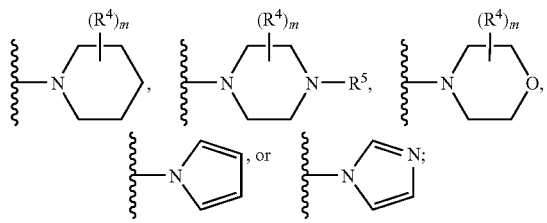

R$^2$ is —(C$_1$-C$_{10}$ alkyl), —(C$_3$-C$_8$) cycloakyl, phenyl, naphthyl, anthryl, phenanthryl, or -(5 to 7 membered) heteroaryl, each being unsubstituted or substituted with 1, 2, or 3 R$^3$ groups;

each R$^3$ is independently -halo, —C(halo)$_3$, —CH(halo)$_2$, —CH$_2$(halo), —CN, —OH, —N$_2$, —NH$_2$, —NH(C$_1$-C$_4$ alkyl), —N(C₁-C₄ alkyl)₂, —(C₁-C₁₀ alkyl), —O(C₁-C₄ alkyl), —CONH₂, —CONH(C₁-C₄ alkyl), or —CON(C₁-C₄ alkyl)₂;

each R⁴ is independently -halo, —C(halo)₃, —CH(halo)₂, —CH₂(halo), —OH, —(C₁-C₄ alkyl), or —O(C₁-C₄ alkyl);

R⁵ is —H, —C(halo)₃, —CH(halo)₂, —CH₂(halo), —(C₁-C₁₀ alkyl), —(CH₂)ᵣO(C₁-C₄ alkyl), —(CH₂)ᵣNH(C₁-C₄ alkyl), or —(CH₂)ᵣN(C₁-C₄ alkyl)₂, where r is an integer selected from the group consisting of 1, 2, 3, and 4;

wherein each R⁶ and R⁷ is independently
(a) H,
(b) —(C₁-C₁₀ alkyl), —CH₂O(C₁-C₄ alkyl), —CH₂NH(C₁-C₄ alkyl), —CH₂N(C₁-C₄ alkyl)₂, —(C₃-C₈)cycloalkyl, phenyl, or -(5 to 7 membered)heteroaryl, each of which is either unsubstituted or substituted with 1, 2, or 3 independently selected R³ groups, or
(c) R⁶ and R⁷ taken together with the carbon atoms to which they are attached form a -(5 to 7 membered) heteroaryl ring or R⁶ and R⁷ taken together with the carbon atoms to which they are attached form an aromatic six-membered carbocyclic ring each of which is unsubstituted or substituted with 1, 2, or 3 independently selected R³ groups; and each halo is independently —F, —Cl, —Br, or —I; and
m is an integer selected from the group consisting of 0, 1, 2, 3, and 4.

6. A compound of formula II(b):

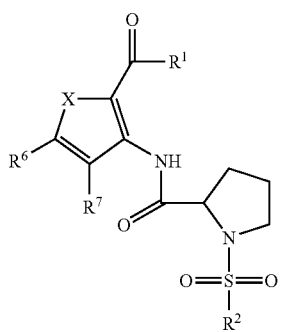

or a pharmaceutically acceptable salt or solvate thereof, wherein:

X is S or O;

R¹ is —(C₁-C₁₀ alkyl), —O(C₁-C₁₀ alkyl), —NH(C₁-C₄ alkyl), —N(C₁-C₄ alkyl)₂,

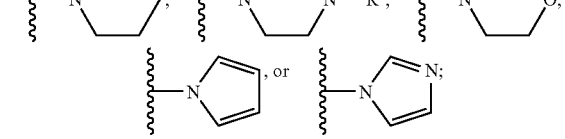

R² is —(C₁-C₁₀ alkyl), —(C₃-C₈) cycloalkyl, phenyl, naphthyl, anthryl, phenanthryl, or -(5 to 7 membered) heteroaryl, each being unsubstituted or substituted with 1, 2, or 3 R³ groups;

each R³ is independently -halo, —C(halo)₃, —CH(halo), —CH₂(halo), —CN, —OH, —NQ, —NH₂, —NH(C₁-C₄ alkyl), —N(C₁-C₄ alkyl)₂, —(C₁-C₁₀ alkyl), —O(C₁-C₄ alkyl), —CONH₂, —CONH(C₁-C₄ alkyl), or —CON(C₁-C₄ alkyl)₂;

each R⁴ is independently -halo, —C(halo)₃, —CH(halo)₂, —CH₂(halo), —OH, —(C₁-C₄ alkyl), or —O(C₁-C₄ alkyl);

R¹ is —H, —C(halo)₃, —CH(halo)₂, —CH₂(halo), —(C₁-C₁₀ alkyl), —(CH₂)ᵣO(C₁-C₄ alkyl), —(CH₂)ᵣNH(C₁-C₄ alkyl), or —(CH₂)ᵣN(C₁-C₄ alkyl)₂, where r is an integer selected from the
group consisting of 1, 2, 3, and 4;

each halo is independently —F, —Cl, —Br, or —I;

wherein each R⁶ and R⁷ is independently
(a) H,
(b) —(C₁-C₁₀ alkyl), —CH₂O(C₁-C₄ alkyl), —CH₂NH(C₁-C₄ alkyl), —CH₂N(C₁-C₄ alkyl)₂, —(C₃-C₈)cycloalkyl, phenyl, or -(5 to 7 membered)heteroaryl, each of which is either unsubstituted or substituted with 1, 2, or 3 independently selected R³ groups, or
(c) R⁶ and R⁷ taken together with the carbon atoms to which they are attached form a -(5 to 7 membered) heteroaryl ring or R⁶ and R⁷ taken together with the carbon atoms to which they are attached form an aromatic six-membered carbocyclic ring each of which is unsubstituted or substituted with 1, 2, or 3 independently selected R³ groups; and and m is an integer selected from the group consisting of 0, 1, 2, 3, and 4.

7. A compound of formula X:

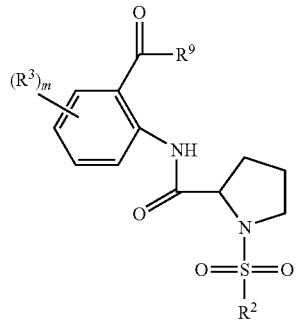

or a pharmaceutically acceptable salt or solvate thereof, wherein:

R⁹ is —(C₁-C₁₀ alkyl), —NH(C₁-C₄ alkyl), —N(C₁-C₄ alkyl)₂,

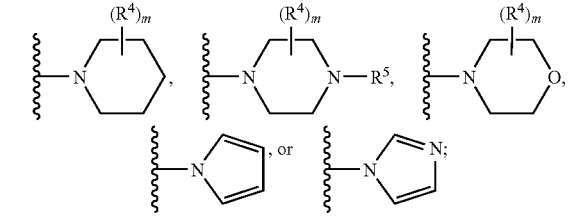

R² is —(C₁-C₁₀ alkyl), —(C₃-C₈) cycloalkyl, phenyl, naphthyl, anthryl, phenanthryl, or -(5 to 7 membered) heteroaryl, each being unsubstituted or substituted with 1, 2, or 3 R³ groups;

each R³ is independently -halo, —C(halo)₃, —CH(halo)₂, —CH₂(halo), —CN, —OH, —NO₂, —NH₂, —NH(C₁-C₄ alkyl), —N(C$_1$-C$_4$ alkyl)$_2$, —(C$_1$-C$_{10}$ alkyl), —O(C$_1$-C$_4$ alkyl), —CONH$_2$, —CONH(C$_1$-C$_4$ alkyl), or —CON(C$_1$-C$_4$ alkyl)$_2$;

each R$^4$ is independently -halo, —C(halo)$_3$, —CH(halo)$_2$, —CH$_2$(halo), —OH, —(C$_1$-C$_4$ alkyl), or —O(C$_1$-C$_4$ alkyl);

R$^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4;

each halo is independently —F, —Cl, —Br, or —I; and each m is independently an integer selected from the group consisting of 0, 1, 2, 3, and 4.

8. A compound of formula XI:

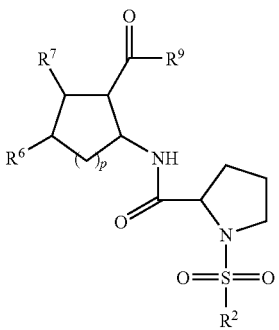

or a pharmaceutically acceptable salt or solvate thereof, wherein:

R$^9$ is —(C$_1$-C$_{10}$ alkyl), —NH(C$_1$-C$_4$ alkyl), —N(C$_1$-C$_4$ alkyl)$_2$,

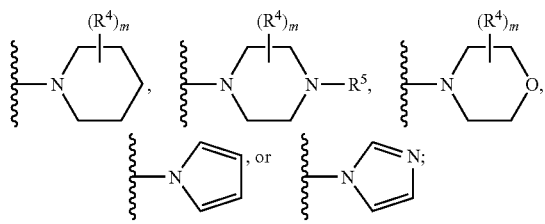

R$^2$ is —(C$_1$-C$_{10}$ alkyl), —(C$_3$-C$_8$) cycloalkyl, phenyl, naphthyl, anthryl, phenanthryl, or -(5 to 7 membered) heteroaryl, each being unsubstituted or substituted with 1, 2, or 3 R$^3$ groups;

each R$^3$ is independently -halo, —C(halo)$_3$, —CH(halo)$_2$, —CH$_2$(halo), —CN, —OH, —NO$_2$, —NH$_2$, —NH(C$_1$-C$_4$ alkyl), —N(C$_1$-C$_4$ alkyl)$_2$, —(C$_1$-C$_{10}$ alkyl), —O(C$_1$-C$_4$ alkyl), —CONH$_2$, —CONH(C$_1$-C$_4$ alkyl), or —CON(C$_1$-C$_4$ alkyl);

each R$^4$ is independently -halo, —C(halo)$_3$, —C(halo)$_2$, —CH$_2$(halo), —OH, —(C$_1$-C$_4$ alkyl), or —O(C$_1$-C$_4$ alkyl);

R$^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4;

each halo is independently —F, —Cl, —Br, or —I;

wherein each R$^6$ and R$^7$ is independently (a) H, (b) —(C$_1$-C$_{10}$ alkyl), —CH$_2$O(C$_1$-C$_4$ alkyl), —CH$_2$NH(C$_1$-C$_4$ alkyl), —CH$_2$N(C$_1$-C$_4$ alkyl)$_2$, —(C$_3$-C$_8$)cycloalkyl, phenyl, or -(5 to 7 membered)heteroaryl, each of which is either unsubstituted or substituted with 1, 2, or 3 independently selected R$^3$ groups, or (c) R$^6$ and R$^7$ taken together with the carbon atoms to which they are attached form a -(5 to 7 membered) heteroaryl ring or R$^6$ and R$^7$ taken together with the carbon atoms to which they are attached form an aromatic six-membered carbocyclic ring each of which is unsubstituted or substituted with 1, 2, or 3 independently selected R$^3$ groups;

p is an integer selected from the group consisting of 0, 1, 2, 3, and 4; and m is an integer selected from the group consisting of 0, 1, 2, 3, and 4.

9. The compound of paragraph 5 wherein the compound is a compound of formula II(a) provided that when X is S, R$^6$ is —H, 7 is —H, and R$^9$ is —NH(C$_1$-C$_4$)alkyl then R$^2$ is not thienyl.

10. The compound of paragraph 7 wherein the compound is a compound of formula X provided that when R$^2$ is phenyl substituted with one —O(C$_1$-C$_4$ alkyl) then R$^9$ is not —CH$_3$.

11. The compound of any one of paragraphs 1, 2, 3, 4, or 6, wherein R$^1$ is —O(CH$_2$CH$_3$).

12. The compound of any one of paragraphs 1, 2, 3, 4, or 6, wherein R$^1$ is

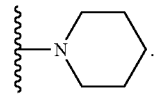

13. The compound of any one of paragraphs 5, 7, or 8, wherein R$^9$ is

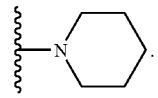

14. The compound of any one of paragraphs 2, 3, or 4, wherein n is 2.

15. The compound of paragraph 1 wherein k is 2.

16. The compound of any one of paragraphs 1, 2, 3, 4, 5, 6, 7, or 8, wherein m is 0.

17. The compound of any one of paragraphs 1, 2, 3, 4, 5, 6, 7, or 8, wherein R$^2$ is

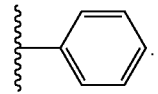

18. The compound of any one of paragraphs 1, 2, 3, 4, 5, 6, 7, or 8, wherein R² is
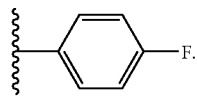
19. The compound of any one of paragraphs 1, 2, 3, 4, 5, 6, 7, or 8, wherein R² is
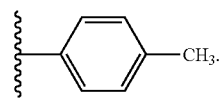
20. The compound of any one of paragraphs 1, 2, 3, 4, 5, 6, 7, or 8, wherein R² is
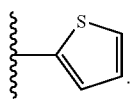
21. The compound of any one of paragraphs 1, 2, 3, 4, 5, 6, 7, or 8 wherein R² is
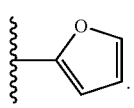
22. The compound of any one of paragraphs 1, 2, 3, 4, 5, 6, 7, or 8, wherein R² is
23. A compound of paragraph 1 selected from the group consisting of,
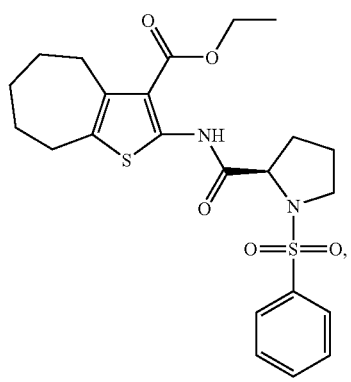
-continued
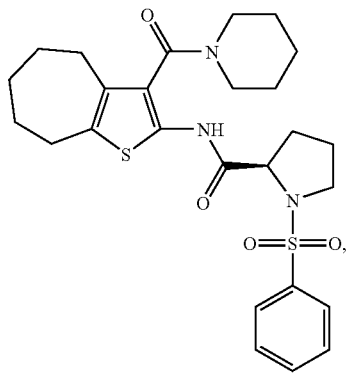
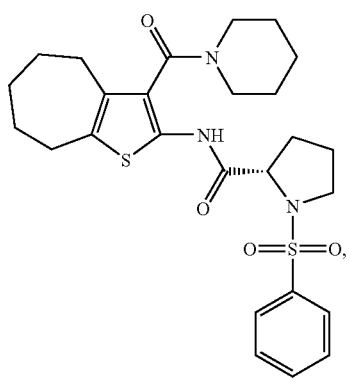
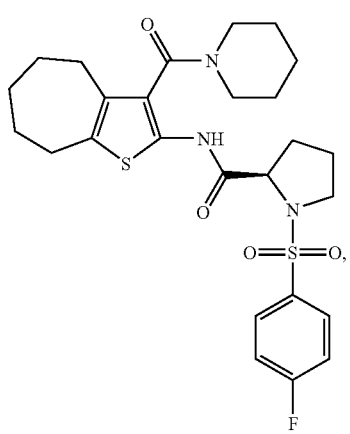
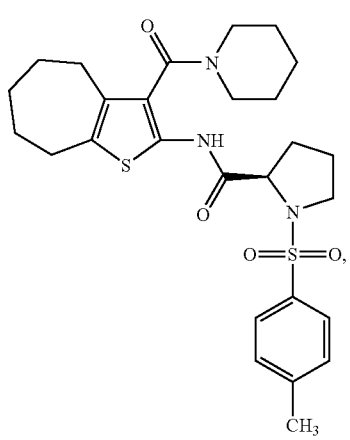

-continued

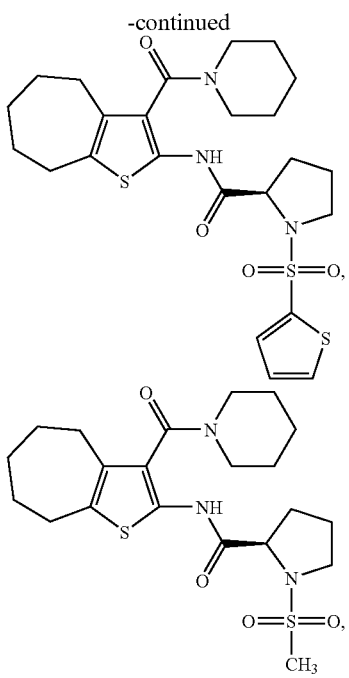

or a pharmaceutically acceptable salt or solvate thereof.

24. The compound of any one of paragraphs 1, 2, 3, 4, 5, or 6, wherein X is S.
25. The compound of any one of paragraphs 1, 2, 3, 4, 5, or 6, wherein X is O.
26. A composition comprising a compound of any one of paragraphs 1, 2, 3, 4, 5, 6, 7, or 8, or a pharmaceutically-acceptable salt or solvate thereof and a pharmaceutically acceptable excipient.
27. A method for modulating a human cannabinoid receptor function in a cell, comprising contacting a cell expressing a cannabinoid receptor with an effective amount of a compound of any one of paragraphs 1, 2, 3, 4, 5, 6, 7, or 8, or a pharmaceutically acceptable salt or solvate thereof
28. The method of paragraph 27, wherein the cannabinoid receptor is a human CB1 cannabinoid receptor.
29. The method of paragraph 27, wherein the cannabinoid receptor is a human CB2 cannabinoid receptor.
30. The method of paragraph 27, wherein said modulation comprises agonizing the cannabinoid receptor function in the cell.
31. The method of paragraph 27, wherein said modulation comprises antagonizing the cannabinoid receptor function in the cell.
32. A method of treating or preventing a Condition in an animal, comprising administering to an animal in need thereof an effective amount of a compound of any one of paragraphs 1, 2, 3, 4, 5, 6, 7, or 8, or a pharmaceutically-acceptable salt or solvate thereof.
33. The method of paragraph 32, wherein the Condition is selected from the group consisting of pain, nausea, vomiting, an eating disorder, an impulse-control disorder, Parkinson's disease, parkinsonism, muscle spasm, epilepsy, a seizure disorder, pruritus, stroke, retinopathy, Huntington's chorea, amyotrophic lateral sclerosis, migraine, dyskinesia, a cognitive disorder, a psychosis, anxiety, and depression.
34. The method of paragraph 33, wherein the Condition is pain.
35. The method of paragraph 34, wherein the pain is selected from the group consisting of acute pain, chronic pain, and pain associated with inflammation.
36. A method for preparing a composition comprising the step of admixing a compound or a pharmaceutically acceptable salt of a compound of any one of paragraphs 1, 2, 3, 4, 5, 6, 7, or 8, and a pharmaceutically acceptable excipient.
37. Use of a compound of any one of paragraphs 1, 2, 3, 4, 5, 6, 7, or 8 or a pharmaceutically acceptable salt or solvate thereof in the manufacture of a medicament to treat a Condition.
38. The use of paragraph 37, wherein the Condition is selected from the group consisting of pain, nausea, vomiting, an eating disorder, an impulse-control disorder, Parkinson's disease, parkinsonism, muscle spasm, epilepsy, a seizure disorder, pruritus, stroke, retinopathy, Huntington's chorea, amyotrophic lateral sclerosis, migraine, dyskinesia, a cognitive disorder, a psychosis, anxiety, and depression.
39. A kit comprising a container containing a compound or a pharmaceutically acceptable salt of a compound of any one of paragraphs 1, 2, 3, 4, 5, 6, 7, or 8.

5.3 Methods for Making the Proline Analog Compounds

Proline Analog Compounds of the present invention can be synthesized according to the methods disclosed herein as well as according to other, analogous synthetic routes disclosed in the art in view of the present disclosure. Reagents and starting materials employed in these syntheses are either available from commercial sources such as Aldrich Chemicals (Milwaukee, Wis.) or they are readily prepared from commercially-available reagents using methods disclosed in the an (see e.g. Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin).

The reaction schemes depicted below illustrate routes for synthesizing representative Proline Analog Compounds of the present invention. Section 6, below, provides a more detailed description of individual reactions as well as a description and characterization of certain Proline Analog Compounds synthesized generally according to the methods disclosed herein.

Separation and purification of the Proline Analog Compounds, as well as the precursors and intermediates thereof disclosed below, can be carried out using methods, procedures, and equipment known in the art in view of the present disclosure including without limitation, appropriate types of chromatography (including e.g. high performance liquid chromatography (HPLC), silica gel column chromatography, and thin-layer chromatography), as well as crystallizations and differential (i.e., liquid-liquid) extraction methods.

Proline Analog Compounds of the present invention contain asymmetric or chiral centers and therefore, exist in different stereoisomeric forms. It is intended that all such stereoisomeric forms of the Proline Analog Compounds of the present invention, as well as mixtures thereof, are included within the scope of the present invention. Where necessary or desired, diastereomeric mixtures can be separated into their individual diastereoisomers according to methods disclosed in the art, including but not limited to separation on a chiral chromatographic matrix or fractional crystallization.

Scheme 1, below, depicts one illustrative approach to the synthesis of Proline Analog Compounds of Formula I, which are compounds of Formula I(a) in which X is S, and $R^1$ is a piperidine moiety.
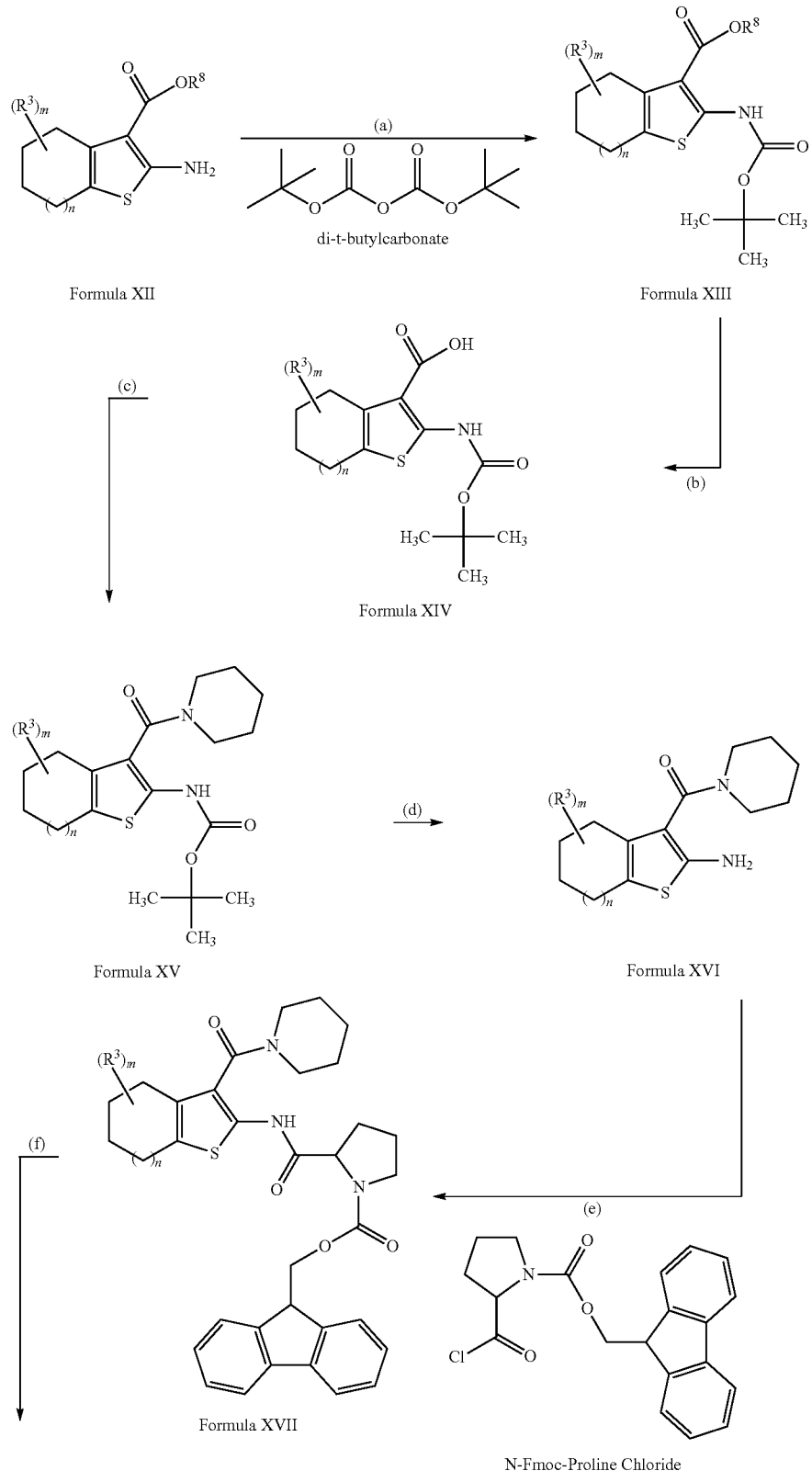

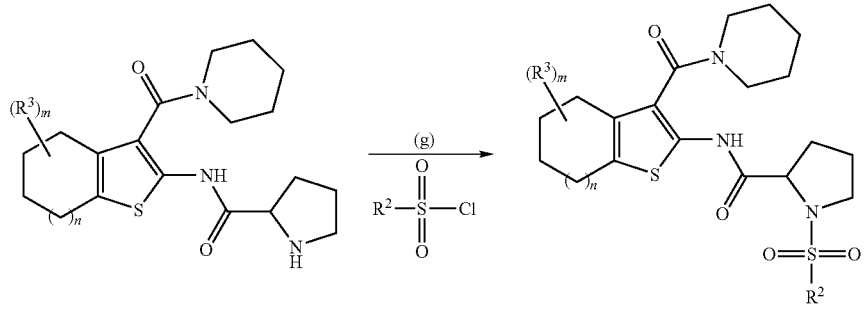

Formula XVIII      Formula XIX

According to Scheme 1, amino esters of Formula XII are reacted with di-t-butyl carbonate (reaction (a)) to provide the N-boc protected compounds of Formula XIII. The ester moiety (in which $R^8$ is a $C_1$-$C_3$ alkyl group; i.e. $R^8$ is methyl, ethyl, n-propyl, or i-propyl) of the compounds of Formula XIII is hydrolyzed in aqueous sodium hydroxide (reaction (b)) to provide the free acid of Formula MV. In reaction (c) the carboxyl group of the compounds of Formula XIV is activated by reaction with di-isopropylcarbodiimide (DIC) and 1-hydroxybenzotriazole (HOBt) and then condensed with piperidine to provide the N-boc-protected compounds of Formula XV. The piperidine-containing compounds of Formula XV are treated with acid (reaction (d)) to remove the boc protecting group, thereby providing compounds of Formula XVI. The free amine of the compounds of Formula XVI is condensed with N-Fmoc-proline chloride in reaction (e) of Scheme 1 to provide intermediates of Formula XVII. The Fmoc protecting group of the compounds of Formula XVII is subsequently removed with base (piperidine) (reaction (f)) to provide the proline-containing compounds of Formula XVIII. Reaction of compounds of Formula XVIII with an appropriate sulfonyl chloride derivative ($R^2$—$SO_2Cl$) provides compounds of Formula XIX (which are compounds of Formula I(a) in which X is S and $R^1$ is piperidine) (reaction (g)).

For example, in specific embodiments, the reactions of Scheme 1 are carried out in which $R^2$ of the sulfonyl chloride reagent of reaction (g) is methyl, phenyl, p-F-phenyl, p-methyl-phenyl, or 2-thiophene, thereby providing, respectively, the following compounds of Formula I(a) in which, for example, m=0, and k=2:

AAD(a)

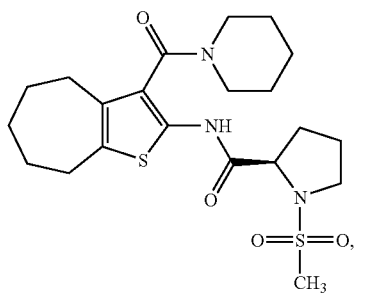

AAA(a)

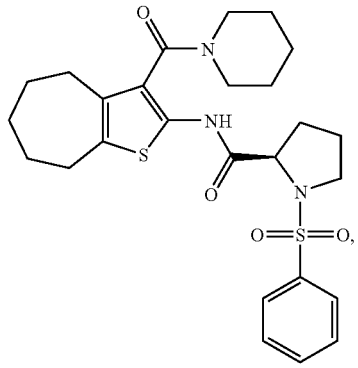

AAB(a)

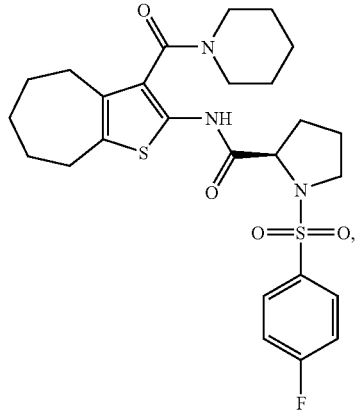

AAC(a)

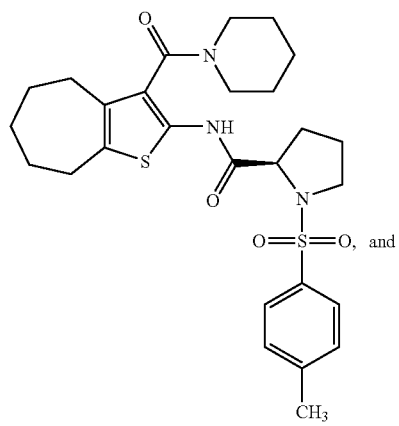

and

-continued

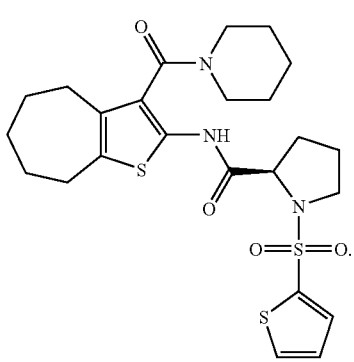
AAF(a)

The reactions of Scheme 1 may also be carried out using a compound of the following formula as the starting material

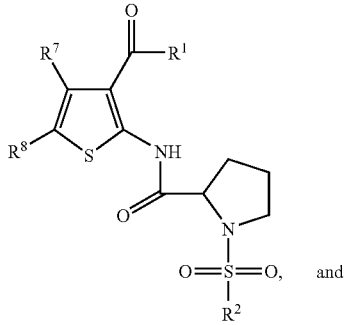
Formula XX to provide compounds of Formula XXI as products, which are compounds of Formula I(b) in which X is S and $R^1$ is a piperidine moiety:

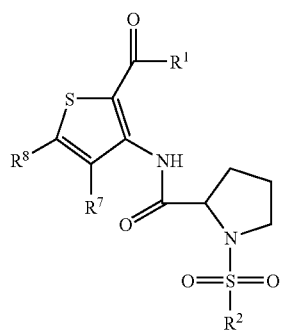
Compounds of Formula XXI

Similarly, reactions of Scheme 1 may be carried out using compounds of the following formulae as starting material:

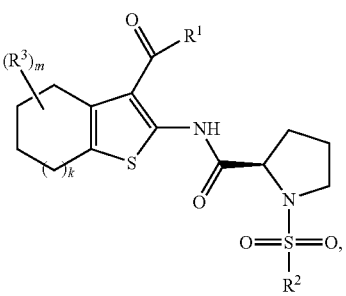
Formula XXII

Formula XXIII to provide compounds of Formula XXIV and Formula XXV, respectively, as products:

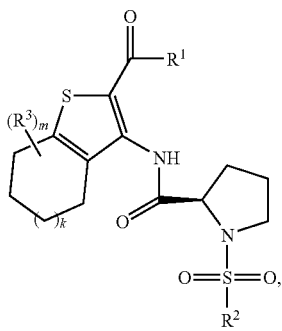
Formula XXIV and

Formula XXV

In certain embodiments, reaction (e) of Scheme 1 can be carried out using Fmoc-D-proline-chloride as the reagent to provide the corresponding D-proline containing compounds of Formulae I(a), I(a), II(a), and II(b), wherein X is S:

Formula I(a)

Formula I(b)

Formula II(a)

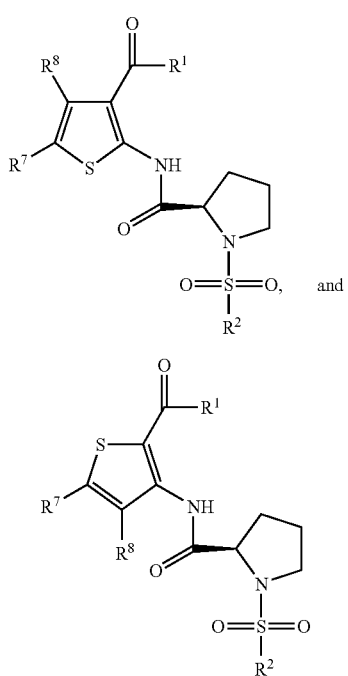

Formula II(b)

to provide die corresponding compounds of Formula III(a) and Formula III(b) as products:

Formula III(a)

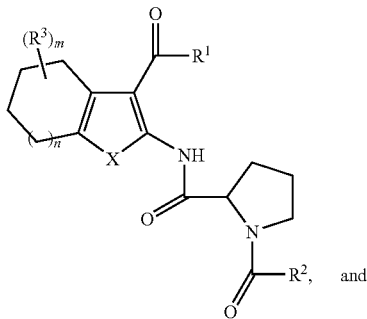

Formula III(b)

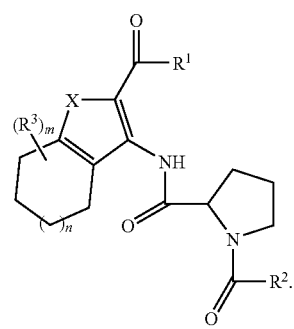

The corresponding L-proline-containing compounds of Formulae I(a), I(b), II(a), and II(b) can be synthesized generally according to the methods of Scheme 1 by using Fmoc-L-proline-chloride as the reagent in step (e) of Scheme 1.

Proline Analog Compounds of Formula III(a) and Formula III(b) may also be synthesized generally according the methods of Scheme 1, above. However, the sulfonyl chloride reagent of step (g) of Scheme 1 is substituted with an acyl-chloride compound of the following formula (where $R^2$ is as described above):

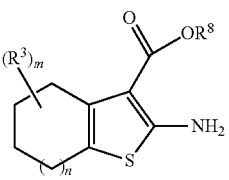

Formula XXVI

As noted above, the corresponding L-proline and D-proline containing derivatives of the Proline Analog Compounds of Formula III(a) and II(b) may be synthesized according the methods of Scheme 1 using the appropriate N-Fmoc-D-proline chloride or N-Fmoc-L-proline chloride reagent in step (e) of Scheme 1.

Alternatively, Proline Analog Compounds of Formulae I(a), I(b), I(a), and II(b), wherein X is S may also be synthesized according the reactions of Scheme 2:

Scheme 2

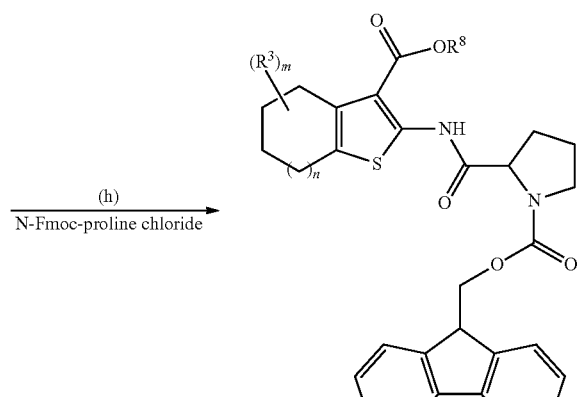

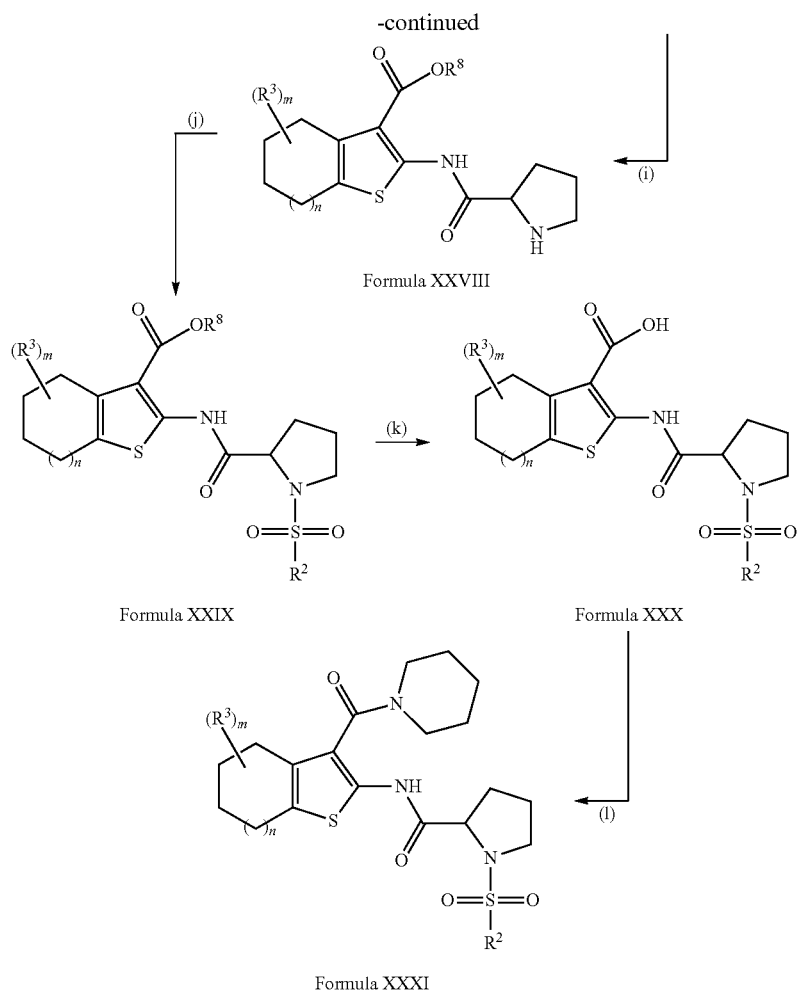

The starting material for the synthetic approach of Scheme 2 is an amino ester of Formula XII. This material is reacted with N-Fmoc-proline chloride (which can be, for example, N-Fmoc-D-proline chloride or N-Fmoc-L-proline chloride)

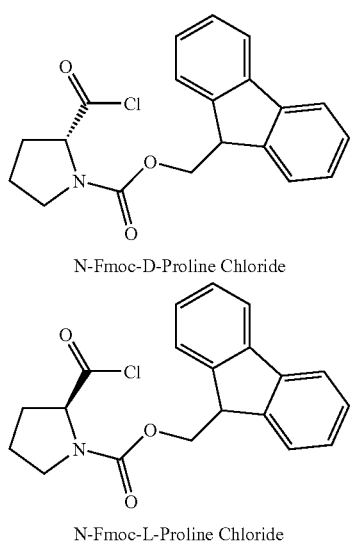

(reaction (h)) to provide the N-protected compounds of Formula XXVII. Removal of the F-moc protecting group of compounds of Formula XXVII with piperidine (reaction (i)) provides the proline-containing compounds of Formula XXVIII, which are then reacted with appropriate sulfonyl chloride reagents ($R^2$—$SO_2Cl$) (reaction (j)) to provide the derivatives of Formula XXIX. Hydrolysis of the esterified moiety of the compounds of Formula XXIX with aqueous NaOH (reaction (k)) will provide compounds of Formula XXX. The carboxyl group of compounds of Formula XXX is activated by reaction with DIC and HOBt and then condensed with piperidine, for example, to provide compounds of Formula XXXI (which are compounds of Formula I(a) in which X is S and $R^1$ is a piperidine moiety) (reaction (1)).

The reactions of Scheme 2 may be carried out using a compound of Formula XX as the starting material to provide a compound of Formula I(b) as the product (e.g. one in which $R^1$ is a piperidine moiety).

Similarly, reactions of Scheme 2 may be carried out using compounds of Formula XXII and Formula XXIII as starting materials to provide compounds of Formula II(a) and Formula II(b), respectively, as products.

The corresponding D-proline and L-proline containing compounds of Formulae I(a), I(b), II(a), and II(b) can be synthesized according to the reactions of Scheme 2 by using the appropriate N-Fmoc-L-proline chloride or N-Fmoc-D-proline chloride reagent in step (h) of Scheme 2.

Proline Analog Compounds of Formula III(a) and Formula III(b) may also be synthesized generally according the methods of Scheme 2, above, using, respectively, compounds of Formula XII and Formula XX as starting materials. However, in this embodiment, the sulfonyl chloride reagent of step (k) of Scheme 2 is replaced with an acyl-chloride compound of Formula XXVI to provide the corresponding compounds of Formula III(a) and Formula III(b).

As noted above, the corresponding L-proline and D-proline containing derivatives of the Proline Analogue Compounds of Formula III(a) and III(b) may be synthesized according the methods of Scheme 2 using the appropriate N-Fmoc-D-proline chloride or N-Fmoc-L-proline chloride reagent in step (h) of Scheme 2.

Scheme 3, below, depicts one illustrative approach to the synthesis of Proline Analog Compounds of Formula XXXVI. For the purposes of this illustration, $R^1$ is a piperidine moiety.

According to the methods of Scheme 3, compounds of Formula XXXII are reacted with N-Fmoc-proline chloride (e.g. N-Fmoc-D-proline chloride or N-Fmoc-L-proline chloride as appropriate) to provide the N-protected compounds of Formula XXI (reaction (m)). The Fmoc protecting group of the compounds of Formula XXXIII is removed with piperidine (reaction (n)) to provide the proline-containing compounds of Formula XXXIV, which can then be reacted with appropriate sulfonyl chloride reagents ($R^2$—$SO_2Cl$) to provide compounds of Formula XXXV (reaction (o)). In the last step of Scheme 3 (reaction (p)), the carboxy group of the compounds of Formula XXXV is activated by reaction with di-isopropylcarbodiimide (DIC) and 1-hydroxybenzotriazole (HOBt) and then condensed with piperidine to provide the compounds of Formula XXXVI, which are compounds of Formula X, in which $R^1$ is a piperidine moiety.

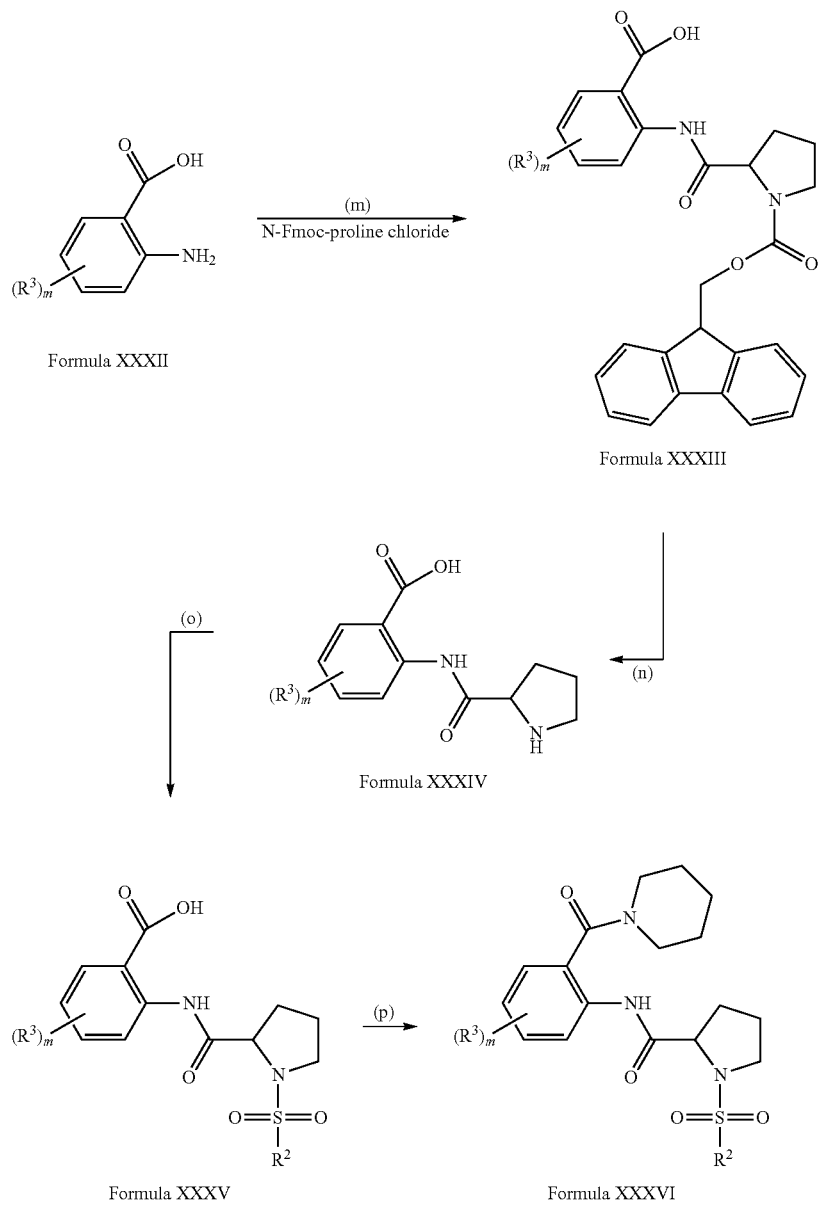

The reactions of Schemes 1, 2, and 3 may also be carried out using a compound of the following formula as the starting material

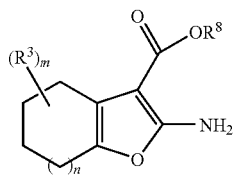

Formula XXXVII to provide compounds of Formula IV(b) as products. In addition, the reactions of Schemes 1, 2, and 3 may also be carried out using a compound of the following formula as the starting material

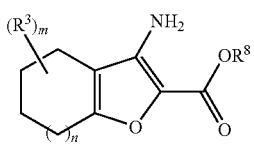

Formula XXXVIII to provide compounds of Formula I(b) as products

Similarly, reactions of Schemes 1, 2, and 3 may be carried out using compounds of the following formulae as starting material:

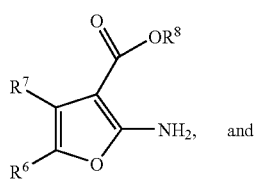

Formula XXXIX

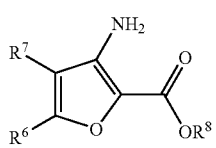

Formula XL to provide compounds of Formula V(a) and Formula V(b), respectively, as products.

And, as noted above, the sulfonyl chloride reagent of step (g) of Scheme 1 can be substituted with an acyl-chloride compound of Formula XXVI, to provide compounds of Formula VI(a) and VI(b). Similarly, the corresponding L-proline-containing and D-proline-containing compounds of Formulae IV(a), IV(b), V(a), V(b), VI(a), and VI(b) can be synthesized, for example, generally according to the methods of Scheme 1 by using, respectively, Fmoc-L-proline-chloride or Fmoc-D-proline-chloride as the reagent in step (e) of Scheme 1.

5.4. Therapeutic Uses of the Proline Analog Compounds

In accordance with the invention, the Proline Analog Compounds are administered to an animal in need of treatment or prevention of a Condition. Illustrative, non-limiting examples of such Conditions are provided below. Each of the conditions, diseases, and disorders described herein is a Condition that can be treated or prevented by administration of an effective amount of a Proline Analog Compound of the present invention.

In one embodiment, an effective amount of certain Proline Analog Compounds can be used to treat or prevent a condition treatable or preventable by stimulating a CB1 and/or CB2 cannabinoid receptor function. In another embodiment, an effective amount of certain Proline Analog Compounds can be used to treat or prevent a condition treatable or preventable by an inhibitor/inverse agonist of a CB1 and/or CB2 cannabinoid receptor function.

The invention also relates to methods for stimulating cannabinoid receptor function in a cell comprising contacting a cell expressing a cannabinoid receptor with a Proline Analog Compound. Such methods are useful for stimulating a cannabinoid receptor function in a cell in vivo, in an animal, in one embodiment a human, by contacting a cell expressing a cannabinoid receptor, in an animal, with a Proline Analog Compound that stimulates the cannabinoid receptor function. The invention further relates to methods for inhibiting a cannabinoid receptor function in a cell comprising contacting a cell expressing a cannabinoid receptor with a Proline Analog Compound. Such methods are useful for inhibiting a cannabinoid receptor function in a cell in vivo, in an animal, in one embodiment a human, by contacting a cell expressing a cannabinoid receptor, in an animal, with a Proline Analog Compound that inhibits the cannabinoid receptor function. Brain tissue, spinal cord tissue, immune cells, cells of the gastrointestinal tract, and primary afferent nerve cells are examples of tissues and cells capable of expressing a cannabinoid receptor. For example, CB1 and/or CB2 are expressed in neuronal and glial cells of the central nervous system, particularly the brain, and especially in the nucleus accumbens, and methods for identifying other cells that express CB1 and/or CB2 are known in the art.

Furthermore, methods for stimulating a cannabinoid receptor function in a cell comprising contacting a cell capable of expressing a cannabinoid receptor with a Proline Analog Compound can be used in vitro, for example, as an assay to identify and/or select cells that express a cannabinoid receptor. Similarly, methods for inhibiting a cannabinoid receptor function in a cell comprising contacting a cell capable of expressing a cannabinoid receptor with a Proline Analog Compound can be used in vitro, for example, as an assay to identify and/or select cells that express a cannabinoid receptor. The invention thus provides methods to identify cells that express CB1 or CB2 and are useful in an assay to screen for compounds useful for treating or preventing a Condition such as, e.g., pain, an addictive disorder, Parkinson's disease, parkinsonism, anxiety, a pruritic condition, or psychosis, among others.

In certain embodiments, a Proline Analog Compound can be used to treat or prevent acute or chronic pain.

A Proline Analog Compound can also be used for treating or preventing pain associated with inflammation or with an inflammatory disease in an animal. Such pain can arise where there is an inflammation of the body tissue which can be a local inflammatory response or a systemic inflammation.

A Proline Analog Compound can be used to treat or prevent an eating disorder. In one aspect of this embodiment, a Proline Analog Compound that is an antagonist/inverse agonist of a cannabinoid receptor is administered to treat obesity.

A Proline Analog Compound can be used to treat or prevent an addictive disorder, an eating disorder, an impulse-control disorder, an alcohol-related disorder, a nicotine-related disorder, an amphetamine-related disorder, a cocaine-related disorder, a hallucinogen-related disorder, an inhalant-related disorder, or an opioid-related disorder, each of which is further sub-classified below.

Eating disorders include, but are not limited to, bulimia nervosa, nonpurging type; bulimia nervosa, purging type; anorexia; and eating disorder not otherwise specified (NOS).

Impulse control disorders include, but are not limited to, intermittent explosive disorder, kleptomania, pyromania, pathological gambling, trichotillomania, and impulse control disorder not otherwise specified (NOS).

Alcohol-related disorders include, but are not limited to, alcohol-induced psychotic disorder with delusions, alcohol abuse, alcohol intoxication, alcohol withdrawal, alcohol intoxication delirium, alcohol withdrawal delirium, alcohol-induced persisting dementia, alcohol-induced persisting amnestic disorder, alcohol dependence, alcohol-induced psychotic disorder with hallucinations, alcohol-induced mood disorder, alcohol-induced anxiety disorder, alcohol-induced sexual dysfunction, alcohol-induced sleep disorder, and alcohol-related disorder not otherwise specified (NOS).

Nicotine-related disorders include, but are not limited to, nicotine dependence, nicotine withdrawal, and nicotine-related disorder not otherwise specified (NOS).

Amphetamine-related disorders include, but are not limited to, amphetamine dependence, amphetamine abuse, amphetamine intoxication, amphetamine withdrawal, amphetamine intoxication delirium, amphetamine-induced psychotic disorder with delusions, amphetamine-induced psychotic disorders with hallucinations, amphetamine-induced mood disorder, amphetamine-induced anxiety disorder, amphetamine-induced sexual dysfunction, amphetamine-induced sleep disorder, and amphetamine related disorder not otherwise specified (NOS).

Cocaine-related disorders include, but are not limited to, cocaine dependence, cocaine abuse, cocaine intoxication, cocaine withdrawal, cocaine intoxication delirium, cocaine-induced psychotic disorder with delusions, cocaine-induced psychotic disorders with hallucinations, cocaine-induced mood disorder, cocaine-induced anxiety disorder, cocaine-induced sexual dysfunction, cocaine-induced sleep disorder, and cocaine related disorder not otherwise specified (NOS).

Hallucinogen-related disorders include, but are not limited to, hallucinogen dependence, hallucinogen abuse, hallucinogen intoxication, hallucinogen withdrawal, hallucinogen intoxication delirium, hallucinogen-induced psychotic disorder with delusions, hallucinogen-induced psychotic disorders with hallucinations, hallucinogen-induced mood disorder, hallucinogen-induced anxiety disorder, hallucinogen-induced sexual dysfunction, hallucinogen-induced sleep disorder, hallucinogen persisting perception disorder (flashbacks), and hallucinogen related disorder not otherwise specified (NOS).

Inhalant-related disorders include, but are not limited to, inhalant dependence, inhalant abuse, inhalant intoxication, inhalant intoxication delirium, inhalant-induced psychotic disorder with delusions, inhalant-induced psychotic disorder with hallucinations, inhalant-induced anxiety disorder, and inhalant related disorder not otherwise specified (NOS).

Opioid-related disorders include, but are not limited to, opioid dependence, opioid abuse, opioid intoxication, opioid intoxication delirium, opioid-induced psychotic disorder with delusions, opioid-induced psychotic disorder with hallucinations, opioid-induced anxiety disorder, opioid withdrawal, and opioid related disorder not otherwise specified (NOS).

A Proline Analog Compound can be used to treat or prevent Parkinson's disease and parkinsonism, and the symptoms associated with Parkinson's disease and parkinsonism, including but not limited to, bradykinesia, muscular rigidity, resting tremor, and impairment of postural balance.

A Proline Analog Compound can be used to treat or prevent generalized anxiety or severe anxiety and the symptoms associated with anxiety, including but not limited to, restlessness, tension, tachycardia, dyspnea, depression including chronic "neurotic" depression, panic disorder, agoraphobia and other specific phobias, eating disorders, and personality disorders.

A Proline Analog Compound can be used to treat or prevent epilepsy, including but not limited to, partial epilepsy, generalized epilepsy, and the symptoms associated with epilepsy, including but not limited to, simple partial seizures, Jacksonian seizures, complex partial (psychomotor) seizures, convulsive seizures (grand mal or tonic-clonic seizures), petit mal (absence) seizures, and status epilepticus.

A Proline Analog Compound can be used to treat or prevent a seizure, including but not limited to, infantile spasms, febrile seizures, and epileptic seizures.

A Proline Analog Compound can be used to treat or prevent strokes, including but not limited to, ischemic strokes and hemorrhagic strokes.

A Proline Analog Compound can be used to treat or prevent a pruritic condition, including but not limited to, pruritus caused by dry skin, scabies, dermatitis, herpetiformis, atopic dermatitis, pruritus vulvae et ani, malaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, and fiberglass dermnatitis.

A Proline Analog Compound can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

A Proline Analog Compound can be used to treat or prevent a cognitive disorder, including but not limited to, delirium and dementia such as multi-infarct dementia, dementia pugilistica, dementia caused by AIDS, and dementia caused by Alzheimer's disease.

A Proline Analog Compound can be used to treat or prevent a memory deficiency, including but not limited to, dissociative amnesia and dissociative fugue.

A Proline Analog Compound can be used to treat or prevent restricted brain function, including but not limited to, that caused by surgery or an organ transplant, restricted blood supply to the brain, a spinal cord injury, a head injury, hypoxia, cardiac arrest, and hypoglycemia.

A Proline Analog Compound can be used to treat or prevent Huntington's chorea.

A Proline Analog Compound can be used to treat or prevent ALS.

A Proline Analog Compound can be used to treat or prevent AIDS-related cachexia.

A Proline Analog Compound can be used to treat or prevent emesis.

A Proline Analog Compound can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

A Proline Analog Compound can be used to treat or prevent a muscle spasm.

A Proline Analog Compound can be used to treat or prevent a migraine.

A Proline Analog Compound can be used to treat or prevent vomiting, including but not limited to, nausea vomiting, dry vomiting (retching), and regurgitation.

A Proline Analog Compound can be used to treat or prevent dyskinesia, including but not limited to, tardive dyskinesia and biliary dyskinesia.

A Proline Analog Compound can be used to treat or prevent depression, including but not limited to, major depression and bipolar disorder.

5.4.1 Therapeutic/Prophylactic Administration and Compositions of the Invention Due to their activity, the Proline Analog Compounds are advantageously useful in veterinary and human medicine. As described above, the Proline Analog Compounds are useful for treating or preventing a Condition in an animal in need thereof.

When administered to an animal, the Proline Analog Compounds can be administered as a component of a pharmaceutical composition that comprises a pharmaceutically acceptable carrier or excipient. Methods of administration include but are not limited to intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Proline Analog Compounds into the bloodstream.

In one embodiment, the composition is administered orally. In another embodiment, the composition is administered by infusion or bolus injection, or by absorption through epithelial or mucocutaneous linings (e.g., oral mucosa, rectal, and intestinal mucosa, etc.). Administration can be systemic or local. Various delivery systems are known, e.g., encapsulation in liposomes, microparticles, microcapsules, capsules, etc., and can be used to administer the Proline Analog Compounds.

In specific embodiments, it may be desirable to administer the Proline Analog Compounds locally. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material.

In certain embodiments, it will be desirable to introduce the Proline Analog Compound into the central nervous system or into the gastrointestinal tract by a suitable route such as by intraventricular, intrathecal, or epidural injection, and by enema. Intraventricular injection can be facilitated by an intraventricular catheter, for example, attached to a reservoir, such as an Ommaya reservoir.

Pulmonary administration can be employed, e.g., by use of an inhaler or nebulizer, and formulation with an aerosolizing agent, or via perfusion in a fluorocarbon or synthetic pulmonary surfactant. In certain embodiments, the Proline Analog Compound is formulated as a suppository, with traditional binders and excipients such as triglycerides.

In another embodiment, the Proline Analog Compound is delivered in a vesicle, in particular a liposome (see Langer, *Science* 249:1527-1533 (1990) and Treat et al., *Liosomes in the Therapy of Infectious Disease and Cancer* 317-327 and 353-365 (1989).

In yet another embodiment, the Proline Analog Compound is delivered in a controlled-release system (see, e.g., Goodson, in *Medical Applications of Controlled Release*, supra, vol. 2, pp. 115-138 (1984)). Other controlled release systems, such as those discussed in the review by Langer, *Science* 249:1527-1533 (1990), may be used. In one embodiment, a pump may be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, a polymeric material can be used (see *Medical Applications of Controlled Release* (Langer and Wise eds., 1974); *Controlled Drug Bioavailability, Drug Product Design and Performance* (Smolen and Ball eds., 1984); Langer and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled release system can be placed in vivo in the proximity of a cell or tissue target of the Proline Analog Compound, thereby requiring the administration of only a fraction of the systemic dose.

Suitable pharmaceutical excipients can be selected from liquids, such as water and oils, including those of petroleum, animal, vegetable, or synthetic origin, such as peanut oil, soybean oil, mineral oil, sesame oil and the like. The pharmaceutical excipient can be selected from saline, gum acacia, gelatin, starch paste, talc, keratin, colloidal silica, urea, and the like. In addition, auxiliary, stabilizing, thickening, lubricating, and coloring agents may be used. When administered to an animal, the pharmaceutically acceptable excipient should be sterile. Water is a particularly useful excipient when the Proline Analog Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skin milk, glycerol, propylene glycol, water, ethanol, and the like. The pharmaceutical composition may also contain minor amounts of wetting or emulsifying agents, or pH buffering agents.

Suitable pharmaceutically acceptable carriers or excipients for intravenous administration of a Proline Analog Compound include, e.g., normal (about 0.9% (w/v)) saline, about 25 to about 30% (w/v) polyethylene glycol ("PEG") diluted with saline or water, and about 2 to about 30% (w/v) hydroxypropyl β-cyclodextrin diluted with water.

Suitable pharmaceutically acceptable carriers or excipients for intraperitoneal administration of a Proline Analog Compounds include, e.g., normal (about 0.9% (w/v)) saline, about 25 to about 30% (w/v) PEG diluted with saline or water, about 25 to about 30% (w/v) propylene glycol (PG) diluted with saline or water, and about 2 to about 30% (w/v) hydroxypropyl β-cyclodextrin diluted with water.

Suitable pharmaceutically acceptable carriers or excipients for subcutaneous and intramuscular administration of the Proline Analog Compound include, but are not limited to, water, normal (about 0.9% (w/v)) saline, about 25 to about 30% (w/v) PEG diluted with saline or water, and about 25 to about 30% (w/v) PG diluted with saline or water.

Suitable pharmaceutically acceptable carriers or excipients for oral administration of the Proline Analog Compounds include, but are not limited to, water, normal (about 0.9% (w/v)) saline, about 25 to about 30% (w/v) polyethylene glycol (PEG) diluted with saline or water, about 2 to about 30% hydroxypropyl β-cyclodextrin (w/v) diluted with water, about 25 to about 30% (w/v) PG diluted with saline or water, and about 1 to about 5% (w/v) methylcellulose diluted with water.

Suitable pharmaceutically acceptable carriers or excipients for intracerebroventricular and intrathecal administration of the Proline Analog Compounds include, but are not limited to, normal (about 0.9% (w/v)) saline.

The present compositions can take the form of solutions, suspensions, emulsions, tablets, pills, pellets, extruded multi-particulates, capsules, capsules containing liquids, powders, sustained release formulations, suppositories, aerosols, sprays, suspensions, or any other form suitable for use. Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Proline Analog Compounds are formulated in accordance with routine procedures as a composition adapted for oral administration to an animal, particularly a human being. Compositions for oral delivery may be in the form of tablets, lozenges, aqueous or oily suspensions, granules, extruded microparticulates powders, emulsions, capsules, syrups, or elixirs, for example. Orally administered compositions can contain preserving agents, coloring agents, and one or more agents, for example, sweetening agents such as fructose, aspartame or saccharin and flavoring agents such as peppermint, oil of wintergreen, or cherry, to provide a pharmaceutically palatable preparation. Moreover, where in tablet or pill form, the compositions can be coated to delay disintegration and absorption in the gastrointestinal tract, thereby providing a sustained action over an extended period of time. Selectively permeable membranes surrounding an osmotically active driving compound may also be suitable for orally administered compositions, and can provide an essentially zero-order delivery profile as opposed to the spiked profiles of immediate-release formulations. A time delay material such as glycerol monostearate or glycerol stearate may also be used. Oral compositions can include standard excipients such as pharmaceutical grade mannitol, lactose, starch, magnesium stearate, sodium saccharin, cellulose and magnesium carbonate.

In another embodiment, the Proline Analog Compound can be formulated for intravenous administration. In one embodiment, a composition for intravenous administration comprises the compound dissolved in sterile isotonic aqueous buffer. Where necessary, the compositions may also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the Proline Analog Compound is to be administered by infusion, it can be dispensed, for example, from an infusion bottle containing sterile pharmaceutical grade water or saline. Where the Proline Analog Compound is administered by injection, an ampoule of sterile water for injection or saline can be provided so that the ingredients may be mixed prior to administration.

The Proline Analog Compound can be administered by controlled-release means or by other delivery devices that are well known to those of ordinary skill in the art. Examples include, but are not limited to, those described in U.S. Pat. Nos. 4,008,719; 5,591,767; 5,120,548; 5,073,543; 5,639,476; and 5,354,556; each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can readily be selected for use with a Proline Analog Compound. The invention thus encompasses single unit dosage forms suitable for oral administration such as, but not limited to, tablets, capsules, gelcaps, and caplets that are adapted for controlled release.

Controlled release pharmaceutical compositions can have a common goal of improving drug therapy over that achieved by their non-controlled counterparts. In one embodiment a controlled-release composition comprises a minimal amount of a Proline Analog Compound to treat or prevent the Condition in a minimum amount of time. Advantages of controlled release compositions include extended activity of the drug, reduced dosage frequency, and increased patient compliance. In addition, controlled release compositions can favorably affect the time of onset of action or other characteristics, such as blood levels of the Proline Analog Compound, and can thus reduce the occurrence of adverse side effects.

In one embodiment, a formulation can have both immediate release and controlled release components. Thus a controlled release composition can initially release an amount of a Proline Analog Compound that promptly treats or prevents pain, and gradually and continually release another amount of the Proline Analog Compound to maintain this level of therapeutic or prophylactic effect over an extended period of time. To maintain his constant level of the Proline Analog Compound in the body, the Proline Analog Compound can be released from the dosage form at a rate that will replace the amount of Proline Analog Compound being metabolized and excreted from the body. Controlled release of an active ingredient can be triggered by various conditions including, e.g., changes in pH, temperature, concentration or availability of enzymes, concentration or availability of water, or other physiological conditions or compounds.

The amount of the Proline Analog Compounds that will be effective in treating or preventing a Condition will typically depend on the nature and severity of the Condition and can be determined by standard clinical techniques. In vitro and in vivo assays can be employed to help determine optimal effective dosage amounts. The precise dose to be employed can further depend on the intended route of administration and should be decided by a medical practitioner in view of each patient's circumstances and in view of published clinical studies. Suitable effective dosage amounts may range from about 10 micrograms to about 2500 milligrams about every 4 h, although typically about 100 mg or less will be administered. In one embodiment, the effective dosage amount will range from about 0.01 milligrams to about 100 milligrams of a Proline Analog Compound about every 4 h, in another embodiment about 0.020 milligrams to about 50 milligrams about every 4 h, and in another embodiment about 0.025 milligrams to about 20 milligrams about every 4 h. The dosage amounts described herein refer to total amounts administered; that is, if more than one Proline Analog Compound is administered concurrently, the effective dosage amounts correspond to the total amount administered.

Where a cell capable of expressing a cannabinoid receptor is contacted with a Proline Analog Compound in vitro, the effective amount for modulating the receptor will typically range from about 0.01 mg to about 100 mg/L, in one embodiment from about 0.1 mg to about 50 mg/L, and in another embodiment from about 1 mg to about 20 mg/L, of a solution or suspension of compound in a pharmaceutically acceptable carrier or excipient.

Where a cell capable of expressing a cannabinoid receptor is contacted with a Proline Analog Compound in vivo, the effective amount for treating or preventing a Condition will typically range from about 0.01 mg to about 100 mg/kg of body weight per day, in one embodiment from about 0.1 mg to about 50 mg/kg body weight per day, and in another embodiment from about 1 mg to about 20 mg/kg of body weight per day.

Proline Analog Compounds can be assayed in vitro or in vivo for their ability to treat or prevent a Condition prior to use in humans. Animal model systems can be used to demonstrate the safety or efficacy of each Proline Analog Compound.

The present methods for treating or preventing a Condition in an animal in need thereof can further comprise administering another therapeutic agent to the animal in combination with a Proline Analog Compound. In one embodiment, the other therapeutic agent is also administered in an effective amount.

The present methods for modulating CB1 and/or CB2 function in a cell capable of expressing CB1 and/or CB2 can further comprise contacting the cell with an effective amount of another therapeutic agent.

Effective amounts of the other therapeutic agent will typically be known to those skilled in the art. However, it is within the skilled artisan's purview to determine the other therapeutic agent's optimal effective amount. In one embodiment of the invention, where another therapeutic agent is administered to an animal, the effective amount of the Proline Analog Compound is less man its effective amount would be where the other therapeutic agent was not also administered. In this case, without being bound by theory, it is believed that the Proline Analog Compounds and the other therapeutic agent can act synergistically to treat or prevent a Condition.

The other therapeutic agent can be, but is not limited to, an opioid agonist, a non-opioid analgesic, a non-steroidal antiinflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antpyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful anti-migraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zoimitriptan, and mixtures thereof.

The other therapeutic agent can alternatively be an agent useful for reducing any potential side effects of a Proline Analog Compound. For example, if the Proline Analog Compound administered is an CB1 or CB2 antagonist, emesis may be a potential side effect. For example, the other therapeutic agent may be an anti-emetic agent. Examples of useful antiemetic agents include, but are not limited to, metoclopramide, domperidone, prochlorperazine, promethazine, chlorpromazine, trimethobenzamide, odansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

A Proline Analog Compound and the other therapeutic agent can act additively or, in one embodiment, synergistically. In one embodiment, a Proline Analog Compound is administered concurrently with the other therapeutic agent; for example, a composition comprising both an effective amount of a Proline Analog Compound and an effective amount of another therapeutic agent can be administered. Alternatively, a composition comprising an effective amount of a Proline Analog Compound and a different composition comprising an effective amount of another therapeutic agent can be concurrently administered. In another embodiment, an effective amount of a Proline Analog Compound is administered prior or subsequent to administration of an effective amount of another therapeutic agent. In this embodiment, the Proline Analog Compound is administered while the other therapeutic agent exerts its therapeutic effect, or the other therapeutic agent is administered while the Proline Analog Compound exerts its therapeutic effect.

A composition of the invention is generally prepared by admixing a Proline Analog Compound or a pharmaceutically acceptable salt thereof and a pharmaceutically acceptable carrier or excipient. Admixing can be accomplished using methods known for admixing a compound (or salt) and a pharmaceutically acceptable carrier or excipient. In one embodiment the composition is prepared such that the Proline Analog Compound is present in the composition in an effective amount.

5.4.2 Kits

The invention encompasses kits that can simplify the administration of a Proline Analog Compound to an animal.

A typical kit of the invention comprises a unit dosage form of a Proline Analog Compound. In one embodiment, the unit dosage form is a container, which can be sterile, containing an effective amount of a Proline Analog Compound and a pharmaceutically acceptable carrier or excipient. The kit can further comprise a label or printed instructions instructing the use of the Proline Analog Compound to treat a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a Proline Analog Compound, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such devices include, but are not limited to, syringes, drip bags, patches, enema bags, and inhalers.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

6. EXAMPLES

6.1 Synthesis of Proline Analog Compounds

6.1.1 Example 1

Synthesis of Compound AAA(a)

The ethyl ester of Compound 1

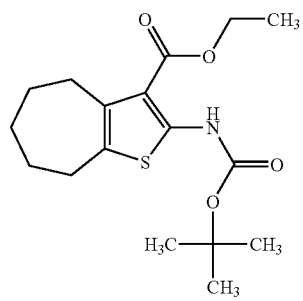

is hydrolyzed in aqueous NaOH to provide Compound 2:

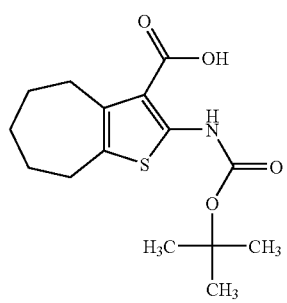

The carboxylic acid moiety of Compound 2 is reacted with 1 equivalent of HOBt, 1 equivalent of 1-[3-(dimethylamino)propyl]-3-ethyl carbodiimide HCl, and 2 equivalents of piperidine in methylene chloride at room temperature overnight to provide Compound 3:

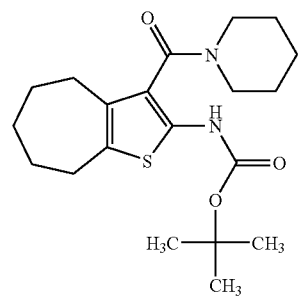

The Boc protecting group of Compound 3 is removed by incubation with acid (HCl) in dioxane for three hours at room temperature to provide Compound 4

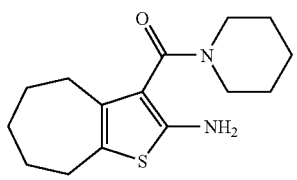

4

Compound 4 can then be reacted with 1 equivalent of N-Fmoc-D-proline chloride and triethyl amine in toluene under nitrogen at 80° C. for 14 hours. The reaction is then stopped, washed with water (0.2 vol) and brine (0.4 vol). The solvent is then removed and the redissolved product can be purified by silica gel column chromatography. The column is washed with hexane:ethyl acetate (100:3) and the product eluted with ethyl acetate to provide Compound 5

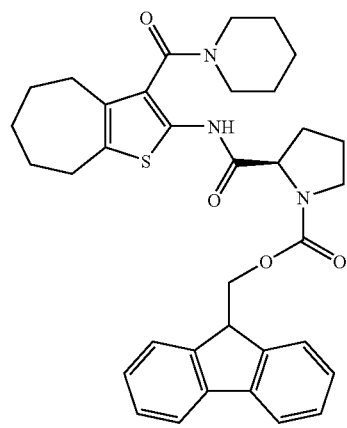

5

The F-moc protecting group of Compound 5 can then be removed with piperidine to provide the deprotected product, Compound 6

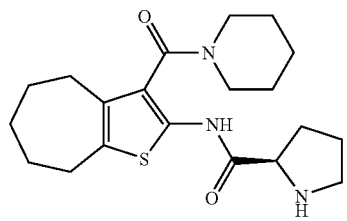

6

Compound 6 is then reacted with benzene sulfonyl chloride (Compound 7)

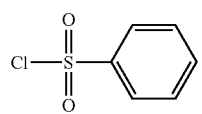

7 in dichloromethane in the presence of triethylamine at room temperature overnight to provide Compound AAA(a)

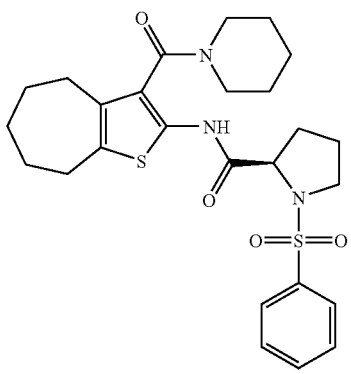

AAA(a)

The crude reaction mixture can be purified by preparative thin-layer chromatography (TLC) with 50% ethyl acetate/hexane. Recovered product can be concentrated and the solvent removed under high vacuum at 50° C. for four hours, and then redissolved in chloroform. This solution can then be washed with aqueous 2N HCl. The washed chloroform solution can then be dried over $NA_2SO_4$, filtered, and concentrated under vacuum.

Compound AAA(a), synthesized generally according to the methods disclosed herein was characterized by (1) nuclear magnetic resonance to provide the following data:
$^1$HNMR(CDCl$_3$): δ 9.63(s, 1H, NH); 7.88(m, 2H); 7.67(m, 1H); 7.58(m, 2H); 4.21(m, 1H); 3.90(m, 1H); 3.65(m, 2H); 3.47(m, 1H); 3.32(m, 1H); 3.18(m, 1H); 2.74(m, 2H); 2.58 (m, 2H); 2.23(m, 1H); 1.8-1.40(m, 15H); and by (2) mass spectroscopy to provide the following data: MS: 516(MHZ$^+$), 1056(2MH$^+$+Na+H).

6.1.2 Example 2

Synthesis of Compound AAB(a)

Compound 6 is reacted with Compound 8

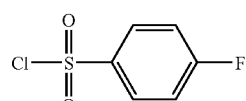

8 in dichloromethane in the presence of triethylamine at room temperature overnight to provide Compound AAB(a)

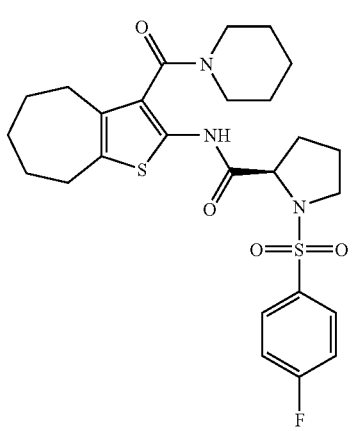

AAB(a)

Compound AAB(a), synthesized generally according to the methods disclosed herein was characterized by (1) nuclear magnetic resonance to provide the following data:
$^1$HNMR(CDCl$_3$): δ 9.65(s, 1H, NH); 7.94(m, 2H); 7.27(m, 2H); 4.21(m, 1H); 3.93(m, 1H); 3.65(m, 2H); 3.47(m, 1H); 3.31(m, 1H); 3.17(m, 1H); 2.74(m, 2H); 2.60(m, 2H); 2.25 (m, 1H); 1.88-1.40(m, 15H); and by (2) mass spectroscopy to provide the following data: MS 534(MH$^+$), 1091(2MH$^+$+Na).

6.1.3 Example 3

Synthesis of Compound AAC(a)

Compound 6 is reacted with Compound 9

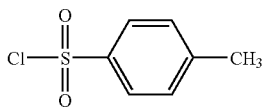

9 in dichloromethane in the presence of triethylamine at room temperature overnight to provide Compound AAC(A)

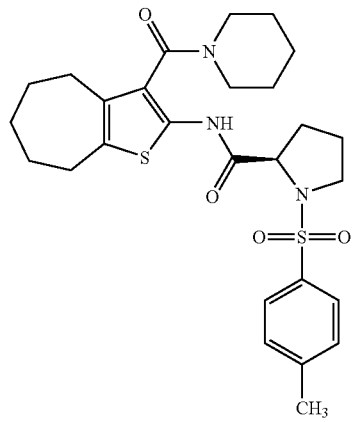

AAC(a)

Compound AAC(a), synthesized generally according to the methods disclosed herein was characterized by (1) nuclear magnetic resonance to provide the following data: $^1$HNMR (CDCl$_3$): δ 9.61(s, 1H, NH); 7.75(d, 2H, J=8.4 Hz); 7.36(d, 2H, J=8.4 Hz); 4.20(m, 1H); 3.87(m, 1H); 3.68(m, 2H); 3.47 (m, 1H); 3.31(m, 1H); 3.14(m, 1H); 2.73(m, 2H); 2.58(m, 2H); 2.45(s, 3H); 2.19(m, 1H); 1.88-1.40(m, 15H); and by (2) mass spectroscopy to provide the following data:
MS: 530(MH$^+$), 1083(2MH$^+$+Na).

6.1.4 Example 4

Synthesis of Compound AAD(a)

Compound 6 is reacted with Compound 10

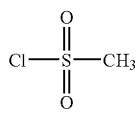

10 in dichloromethane, in the presence of triethylamine at room temperature overnight to provide Compound AAD(a).

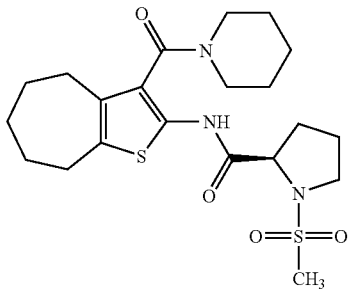

AAD(a)

Compound AAD(a), synthesized generally according to the methods disclosed herein was characterized by (1) nuclear magnetic resonance to provide the following data:
$^1$HNMR(CDCl$_3$): δ 9.66(s, 1H, NH); 4.42(m, 1H); 3.85(m, 1H), 3.60-3.20(m, 6H), 3.01(s, 3H), 2.72(m, 2H), 2.56(m, 2H), 2.39(m, 1H), 2.16(m, 1H), 2.00(m, 2H), 1.86(m, 2H), 1.75-1.40(m, 9H); and by (2) mass spectroscopy to provide the following data: MS 454(MH$^+$), 931(2MH$^+$+Na).

6.1.5 Example 5

Synthesis of Compound AAF(a)

Compound 6 is reacted with Compound 11

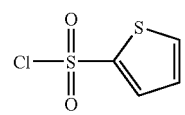

11 in dichloromethane in the presence of triethylamine at room temperature overnight to provide Compound AAF(a)

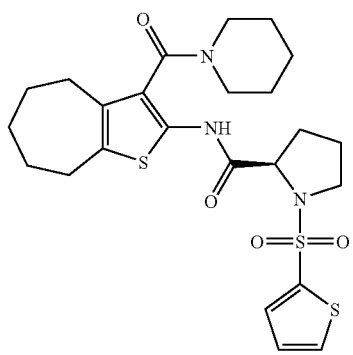

AAF(a)

Compound AAF(a), synthesized generally according to the methods disclosed herein was characterized by (1) nuclear magnetic resonance to provide the following data:
$^1$HNMR(CDCl$_3$): δ 9.60(s, 1H, NH); 7.68(m, 2H); 7.19(m, 1H); 4.23(m, 1H); 3.88(m, 1H); 3.72(m, 2H); 3.42(m, 1H); 3.25(m, 2H); 2.75(m, 2H); 2.57(m, 2H); 2.24(m, 1H); 1.88-1.40(m, 15H); and by (2) mass spectroscopy to provide the following data: MS: 522 (MH$^+$), 1065(2M$^+$+Na).

6.1.6 Example 6

Synthesis of Compound AAA(b)

Compound 4 is reacted with N-Fmoc-L-Proline chloride, generally according to the procedures described for die synthesis of Compound AA(a), above, to provide Compound 12:

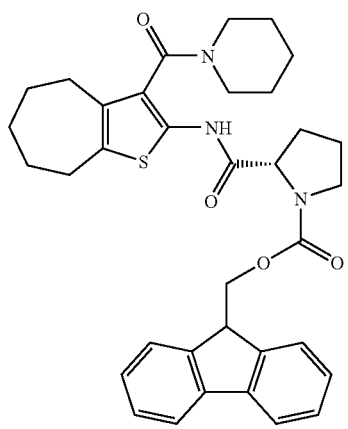

12

The F-Moc group of Compound 12 is removed by reaction with pyridine to provide Compound 13

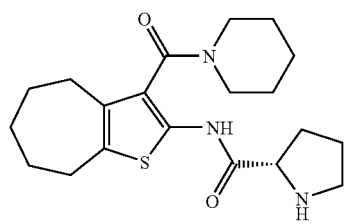

13 which is reacted with Compound 7 to provide Compound AAA(b)

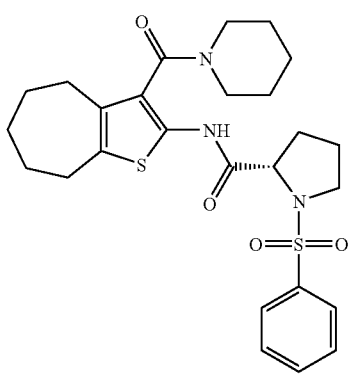

AAA(b)

Compound AAA(b), synthesized generally according to the methods disclosed herein was characterized by (1) nuclear magnetic resonance to provide the following data:
$^1$HNMR(CDCl$_3$): δ 9.62(s, 1H, NH), 7.89(m, 2H), 7.66(m, 1H), 7.60(m, 2H), 4.22(m, 1H), 3.90(m, 1H), 3.65(m, 2H), 3.46(m, 1H), 3.31(m, 1H), 3.18(m, 1H), 2.73(m, 2H), 2.57(m, 2H), 2.20(m, 1H), 1.90-1.40(m, 15H); and by (2) mass spectroscopy to provide the following data: MS 516((MH$^+$), 1032 (2MH$^+$).

6.1.7 Example 7

Synthesis of Compound EAA(a)

Compound 6 is reacted with Compound 14

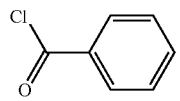

14 to provide Compound EAA(a)

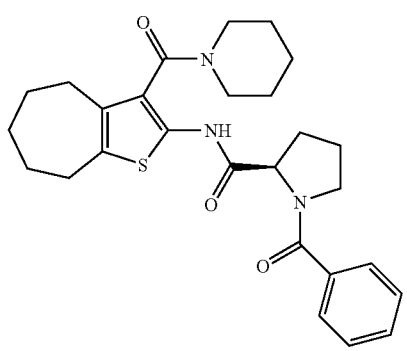

EAA(a)

Compound EAA(a), synthesized generally according to the methods disclosed herein was characterized by (1) nuclear magnetic resonance to provide the following data: $^1$HNMR (CDCl$_3$): δ 10.02(s, 1H, NH), 7.67(m, 2H), 7.44(m, 3H), 4.95(m, 1H), 3.62(m, 2H), 3.50(m, 2H), 3.29(m, 2H), 2.73(m, 2H), 2.54(m, 2H), 2.46(m, 1H), 2.18(m, 1H), 2.03(m, 1H), 1.85(m, 3H), 1.70-1.30(m, 10H); and by (2) mass spectroscopy to provide the following data: MS: 480(MH$^+$), 960 (2MH$^+$).

6.1.8 Example 8

Synthesis of Compound ABE(a)

Compound 15

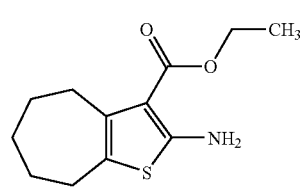

15 is reacted with N-Fmoc-D-proline chloride, generally according to the conditions provided above for the synthesis of Compound AAA(a), to provide Compound 16:

16

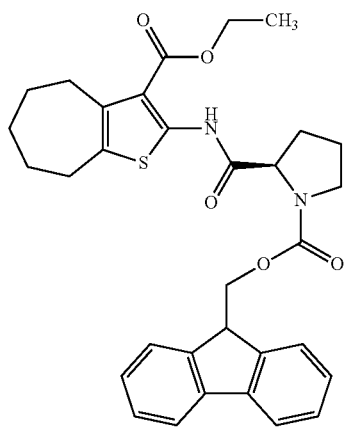

The Fmoc group of Compound 16 is removed by reaction with piperidine to provide Compound 17

17

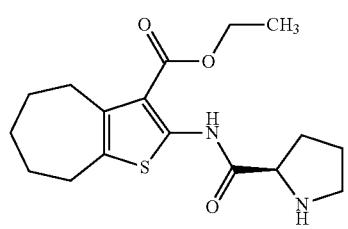

Compound 17 is reacted with Compound 7 to provide Compound ABE(a)

ABE(a)

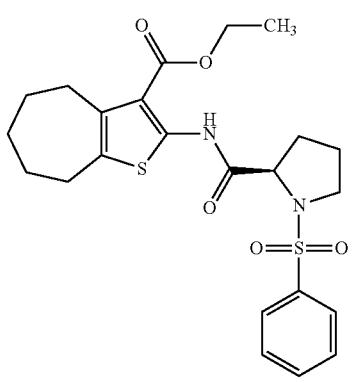

Compound ARE(a), synthesized generally according to the methods disclosed herein, was characterized by (1) nuclear magnetic resonance to provide the following data:

$^1$HNMR(CDCl$_3$): δ 7.90(m, 2H, 7.64(m, 1H); 7.57(m, 2H); 4.48(m, 2H); 4.32(m, 1H); 3.69(m, 1H); 3.08(m, 2H); 2.74 (m, 2H); 2.20(m, 1H); 1.85(m, 2H); 1.60(m, 6H); 1.42(t, 3H, J=7.2 Hz); and by (2) mass spectroscopy to provide the following data: MS: 477(MH$^+$), 975(2M$^+$+Na).

6.1.9 Example 9

Synthesis of Compound CAA(a)

The esterified methyl group of Compound 18

18

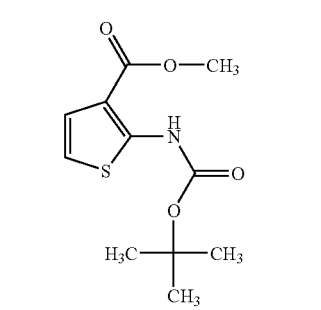

is removed by reaction with aqueous NaOH to provide Compound 19

19

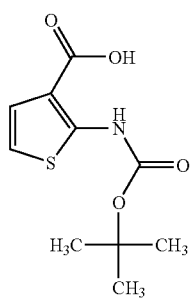

The carboxylic acid of Compound 19 is reacted with 1 equivalent of HOBt, 1 equivalent of 1-[3-(dimethylamino) propyl]-3-ethyl carbodiimide HCl, and 2 equivalents of piperidine in methylene chloride at room temperature overnight to provide Compound 20

20

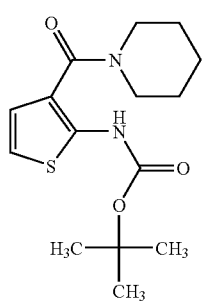

The Boc protecting group of Compound 20 is removed with acid (HCl) in dioxane for three hours at room temperature to provide Compound 21

21

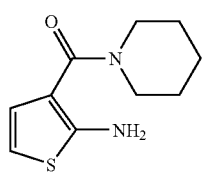

Compound 21 can then be reacted with N-Fmoc-D-proline chloride under the conditions described above for the synthesis of Compound AAA(a), to provide Compound 22

22

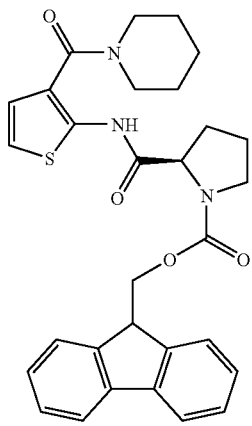

Removal of the Fmoc protecting group of Compound 22 with piperidine provides Compound 23

23

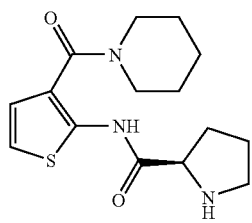

which can be reacted with benzyl sulfonyl chloride (Compound 7) to provide Compound CAA(a)

CAA(a)

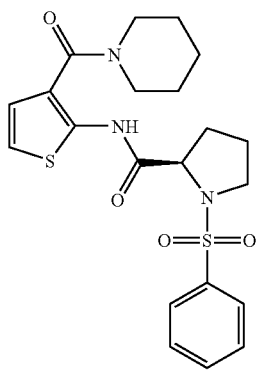

Compound CAA(a), synthesized generally according to the methods disclosed herein was characterized by (1) nuclear magnetic resonance to provide the following data:

$^1$HNMR(CDCl$_2$): δ 11.20(s, 1H, NH), 7.93(m, 2H), 7.64(m, 1H), 7.56(m, 2H), 6.90(d, 1H, J=6 Hz), 6.81(d, 1H, J=6 Hz), 4.34(m, 1H), 3.67(m, 5H), 3.29(m, 1H), 2.22(m, 1H), 1.90-1.60(m, 10H); and by (2) mass spectroscopy to provide the following data: MS: 448(MH$^+$), 917(2M$^+$+Na).

6.1.10 Example 10

Synthesis of Compound DAA(a)

Compound 24

24

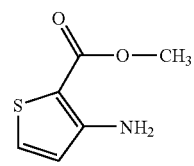

is reacted with N-Fmoc-D-proline chloride generally according to the methods disclosed above for the synthesis of Compound AAA(a), to provide Compound 25

25

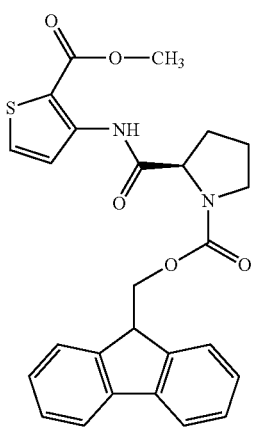

Removal of the Fmoc protecting group of Compound 25 with piperidine provides Compound 26

26

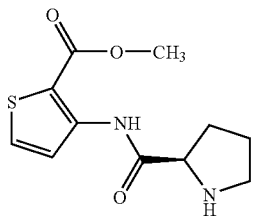

Condensation of Compound 26 with benzene sulfonyl chloride (Compound 7) in dichloromethane at room temperature overnight provides Compound 27

27

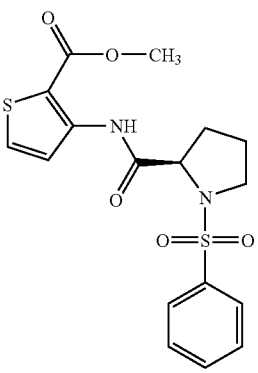

Hydrolysis of the methyl ester of Compound 27 in aqueous NaOH provides Compound 28

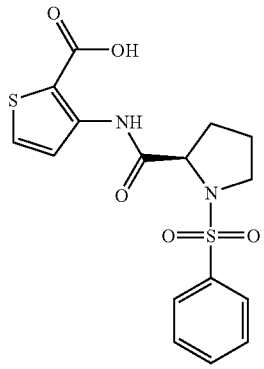

28

Compound 28 is reacted with 1 equivalent of HOBt, 1 equivalent of 1-[3-(dimethylamino)propyl]-3-ethyl carbodiimide HCl, and 2 equivalents of piperidine in methylene chloride at room temperature overnight to provide Compound DAA(a)

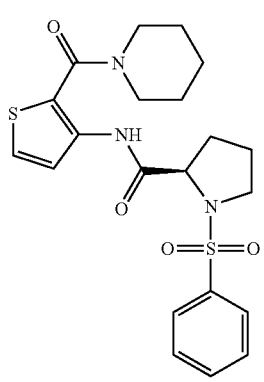

DAA(a)

Compound DAA(a), synthesized generally according to the methods disclosed herein was characterized by (1) nuclear magnetic resonance to provide the following data:
$^1$HNMR(CDCl$_3$): δ 10.77(s, 1H, NH), 7.99(d, 1H, J=5.2 Hz), 7.91(m, 2H), 7.63(m, 1H), 7.55(m, 2H), 7.35(d, 1H, J=5.2 Hz), 4.24(dd, 1H, J=3.2, 8.4 Hz), 3.75(m, 5H), 3.71(m, 1H), 3.28(m, 1H), 2.17(m, 1H), 1.90-1.60(m, 9H); and by (2) mass spectroscopy to provide the following data: MS: 448 (MH$^+$), 471((MH$^+$+Na), 917(2M$^+$+Na).

6.1.11 Example 11

Synthesis of Compound GAA(a)

Compound 30

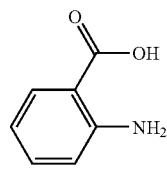

30 can be reacted with 1 equivalent of N-Fmoc-D-proline chloride and triethyl amine in toluene, under nitrogen, at 80° C. for 14 hours to provide Compound 31:

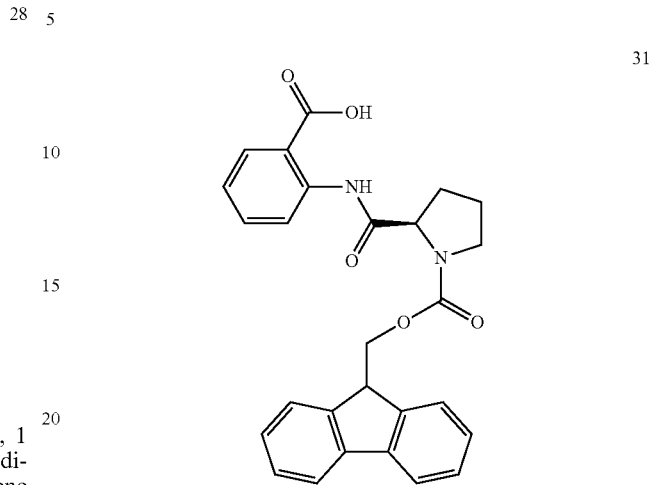

31

The Fmoc protecting group of Compound 31 can then be removed with piperidine to provide Compound 32

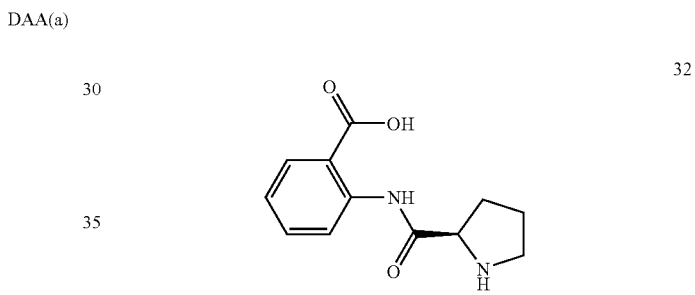

32 which can be reacted with benzene sulfonyl chloride (Compound 7) in dichloromethane, in the presence of triethylamine, at room temperature overnight to provide Compound 33

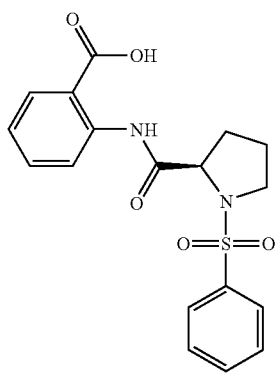

33

Compound 33 is reacted with 1 equivalent of HOBt, 1 equivalent of 1-[3-(dimethylamino)propyl]-3-ethyl carbodiimide HCl, and 2 equivalents of piperidine in methylene chloride at room temperature overnight to provide Compound GAA(a)

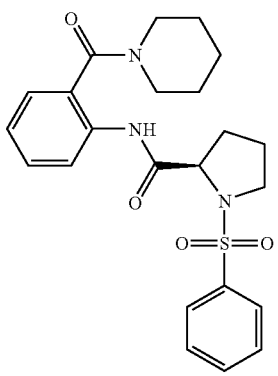

GAA(a)

Compound GAA(a), synthesized generally according to the methods disclosed herein was characterized by (1) nuclear magnetic resonance to provide the following data:
$^1$HNMR(CDCl$_3$): δ 9.60(s, 1H, NH), 8.30(m, 1H), 7.89(m, 2H), 7.66(m, 1H), 7.57(m, 2H), 7.40(dd, 1H, J=1.2, 7.8 Hz), 7.23(dd, 1H, J=1.2, 7.2 Hz), 7.13(dt, 1H, J=1.2, 7.2 Hz), 4.10(dd, 1H, J=2.8, 8.8 Hz), 3.82(m, 2H), 3.73(m, 1H), 3.43 (m, 2H), 3.20(m, 1H), 2.16(m, 1H), 1.80-1.60(m, 9H); and by (2) mass spectroscopy to provide the following data:
MS: 441(M$^+$), 442(MH$^+$), 443(MH$^+$), 905(2M$^+$+Na), 906 (2M$^+$+Na+H).

6.2 In Vitro Assays

Proline Analog Compounds of the present invention were tested for biological activity in one or both of the in vitro assays described below to identify those with CB1 and/or CB2 receptor binding activity, and to identify those cannabinoid receptor-binding compounds as either cannabinoid receptor agonists or antagonists.

6.2.1 Preparation of Membranes Comprising Cannabinoid Receptors

CHO-K1 cells expressing CB1 or CB2 receptors (which were purchased from EuroScreen; Brussels, Belgium) were grown to confluency (20-40×10$^6$ cells) in 10 cm dishes. Cells were lysed by adding 10 mL/dish ice-cold hypotonic buffer (2.5 mM MgCl$_2$, 50 mM HEPES, pH 7.4). Cell lysates were removed using a cell scraper and homogenized 30 seconds with a BioSpec Tissue Tearer™ (Racine, Wis.). Membranes were collected by centrifugation at 30,000 g for 15 min at 4° C. and pellets resuspended in hypotonic buffer to a final concentration of 1-3 mg/mL.

6.2.2 Competition Binding Assay

Membranes (CB1 or CB2 CHO-K1: 1 μg/well) were incubated at room temperature for 1 hour with 0.5 nM [$^3$H]-CP55, 940 in 500 μL of assay buffer (5 mM MgCl$_2$, 5 mg/mL BSA, 2.5 mM EDTA and 50 mM Tris-HCl, pH 7.4) in the presence of increasing concentrations of unlabeled competitors, e.g. WIN55, 212-2 (a CB1 receptor agonist available from Sigma-Aldrich, St. Louis, Mo.) or ligand of interest. The final concentration of DMSO was 5%. Reactions were terminated by rapid filtration using a 96-well filtration apparatus (Brandel, Gaithersburg, Md.) onto GF/C filter plates (PerkinElmer Life Sciences; Boston, Mass.) pretreated with polyethylenimine 0.5% (w/v). The plates were washed three times with 500 μL of ice-cold assay buffer. Filter plates were subsequently dried at 50° C. for 2-3 hours. Fifty microliters per well BetaScint 20 (PerkinElmer) scintillation cocktail was added and plates counted in a TopCount (PerkinElmer) for 1 min/well.

Data were analyzed using GraphPad PRISM™, v. 3.0 (San Diego, Calif.). The concentrations of unlabeled competitors that yield 50% displacement (IC$_{50}$ values) were calculated from each curve by a non-linear regression analysis fined to a one-site model. In separate experiments, equilibrium dissociation constants (K$_d$ values) were determined for each receptor. These values were subsequently used to calculate K$_i$ values (Cheng, Y., and Prusoff, W. H. (1973) "Relationship between the inhibition constant (K$_i$) and the concentration of inhibitor which causes 50 percent inhibition (IC$_{50}$) of an enzymatic reaction," Biochem. Pharmacol. 22: 3099-3108). All K$_i$ values are presented as mean±SEM of n determinations.

6.2.3 GTPγ[$^{35}$S] Functional Binding Assay

Functional GTγ[$^{35}$S] binding assays were conducted by sequentially mixing on ice the following reagents in the order shown to yield the indicated final concentrations: membrane protein (either 0.026 μg/μL CB1 or 0.053 μg/μL CB2, depending on the assay) which can be purchased from PerkinElmer, Boston, Mass.), 10 μg/mL saponin, 30 μM GDP and 0.20 nM GTPγ[$^{35}$S] to binding buffer (100 mM NaCl, 10 mM MgCl$_2$, 1 mg/mL fatty acid-free BSA, 20 mM HEPES, pH 7.4). The prepared membrane solutions (190 μL/well) were transferred to 96-well polypropylene plates containing 10 μL of 20× concentrated serial dilutions of test compounds prepared in DMSO. The final concentration of DMSO was 5%. Plates were incubated for 30 minutes at room temperature with shaking. Reactions were terminated by rapid filtration onto Unifilter-96 GF/B filter plates (PerkinElmer) using a Brandel 96-well tissue harvester, followed by three filtration washes with 200 μL ice-cold wash buffer (10 mM NaH$_2$PO$_4$, 10 mM Na$_2$HPO$_4$, pH 7.4). Filter plates are subsequently dried at 50° C. for 2-3 hours. Fifty microliters per well Betaplate Scint (Perkin Elmer) scintillation cocktail were added and plates counted in a TopCount (liquid scintillation counter, Perkin Elmer) for 1 min/well. Data were analyzed using GraphPad PRISM™, v. 3.0. The concentration of agonist that yields 50% of maximal activity (EC$_{50}$, values) was calculated from each curve by a non-linear regression analysis fitted to a one-site model.

6.2.4.

TABLE 1

Biological Data

| Compound | CB1 | | | CB2 |
| --- | --- | --- | --- | --- |
| | Ki (nM) | EC 50 (nM) | Emax (%) | Ki (nM) |
| AAA(a) | 4.7 | 702.4 | 80 | 4.3 |
| AAB(a) | 43.5 | 1909.3 | 68 | 35.8 |
| AAC(a) | 260.8 | n.a. | 8 | 154.4 |
| AAD(a) | 2186.1 | | | |
| AAF(a) | 7.3 | 425.3 | 150 | 4.5 |
| AAA(b) | 366.3 | n.a. | 8 | |
| EAA(a) | 9289.3 | | | |
| ABE(a) | 15.1 | >25,000 | | 11.5 |
| CAA(a) | 1890.7 | | | |
| DAA(a) | 1242.3 | | | |
| GAA(a) | 1133.3 | | | | where "n.a." indicates that no activity was detected at the highest concentration tested.

The present invention is not to be limited in scope by the specific embodiments disclosed in the examples which are intended as illustrations of a few aspects of the invention and any embodiments that are functionally equivalent are within the scope of this invention. Indeed various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A compound of formula I(a):

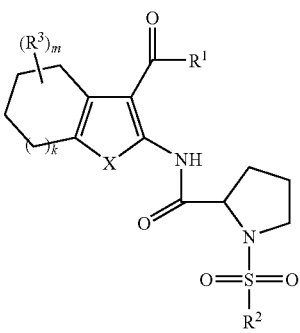

or a pharmaceutically acceptable salt thereof, wherein:
X is S or O;
$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

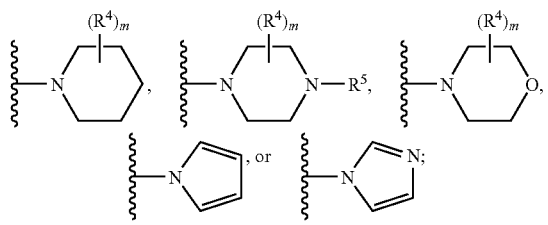

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups;
each $R^3$ is independently -halo, —C(halo)$_3$, —CH(halo)$_2$, —CH$_2$(halo), —CN, —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;
each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);
$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;
each halo is independently —F, —Cl, —Br, or —I;
k is an integer selected from the group consisting of 2, 3, and 4; and
each m is independently an integer selected from the group consisting of 0, 1, 2, 3, and 4.

2. A compound of formula III(a):

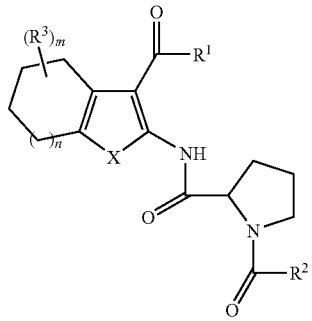

or a pharmaceutically acceptable salt thereof, wherein:
X is S or O;
$R^1$ is —($C_1$-$C_{10}$ alkyl), —O($C_1$-$C_{10}$ alkyl), —NH($C_1$-$C_4$ alkyl), —N($C_1$-$C_4$ alkyl)$_2$,

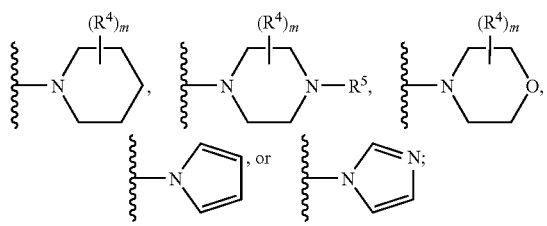

$R^2$ is —($C_1$-$C_{10}$ alkyl), —($C_3$-$C_8$) cycloalkyl, phenyl, naphthyl, anthryl, phenanthryl, or -(5 to 7 membered) heteroaryl, each being unsubstituted or substituted with 1, 2, or 3 $R^3$ groups;
each $R^3$ is independently -halo, —C(halo)$_3$, —CH(halo)$_2$, —CH$_2$(halo), —OH, —NO$_2$, —NH$_2$, —NH($C_1$-$C_4$ alkyl), —N($C_1$-$C_4$ alkyl)$_2$, —($C_1$-$C_{10}$ alkyl), —O($C_1$-$C_4$ alkyl), —CONH$_2$, —CONH($C_1$-$C_4$ alkyl), or —CON($C_1$-$C_4$ alkyl)$_2$;
each $R^4$ is independently -halo, —C(halo)$_3$, —CH(halo)$_2$, —CH$_2$(halo), —OH, —($C_1$-$C_4$ alkyl), or —O($C_1$-$C_4$ alkyl);
$R^5$ is —H, —C(halo)$_3$, —CH(halo)$_2$, —CH$_2$(halo), —($C_1$-$C_{10}$ alkyl), —(CH$_2$)$_r$O($C_1$-$C_4$ alkyl), —(CH$_2$)$_r$NH($C_1$-$C_4$ alkyl), or —(CH$_2$)$_r$N($C_1$-$C_4$ alkyl)$_2$, where r is an integer selected from the group consisting of 1, 2, 3, and 4;
each halo is independently —F, —Cl, —Br, or —I;
n is an integer selected from the group consisting of 0, 1, 2, 3, and 4; and
each m is independently an integer selected from the group consisting of 0, 1, 2, 3, and 4.

3. A compound of formula I(b) or formula III(b):

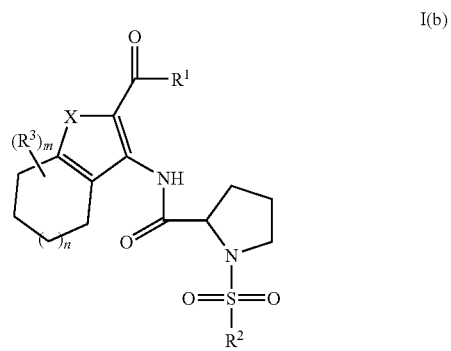

I(b)

-continued

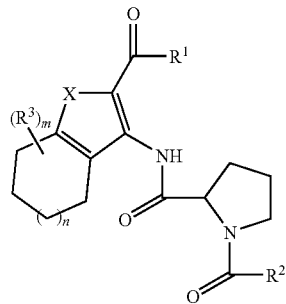
III(b)

or a pharmaceutically acceptable salt thereof, wherein:

X is S or O;

R$^1$ is —(C$_1$-C$_{10}$ alkyl), —O(C$_1$-C$_{10}$ alkyl), —NH(C$_1$-C$_4$ alkyl), —N(C$_1$-C$_4$ alkyl)$_2$, R$^2$ is —(C$_1$-C$_{10}$ alkyl), —(C$_3$-C$_8$) cycloalkyl, phenyl, naphthyl, anthryl, phenanthryl, or -(5 to 7 membered) heteroaryl, each being unsubstituted or substituted with 1, 2, or 3 R$^3$ groups;

each R$^3$ is independently -halo, —C(halo)$_3$, —CH(halo)$_2$, —CH$_2$(halo), —CN, —OH, —NO$_2$, —NH$_2$, —NH(C$_1$-C$_4$ alkyl), —N(C$_1$-C$_4$ alkyl)$_2$, —(C$_1$-C$_{10}$ alkyl), —O(C$_1$-C$_4$ alkyl), —CONH$_2$, —CONH(C$_1$-C$_4$ alkyl), or —CON(C$_1$-C$_4$ alkyl)$_2$;

each R$^4$ is independently -halo, —C(halo)$_3$, —CH(halo)$_2$, —CH$_2$(halo), —OH, —(C$_1$-C$_4$ alkyl), or —O(C$_1$-C$_4$ alkyl);

R$^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4;

each halo is independently —F, —Cl, —Br, or —I;

n is an integer selected from the group consisting of 0, 1, 2, 3, and 4; and each m is independently is an integer selected from the group consisting of 0, 1, 2, 3, and 4.

4. The compound of any one of claims 1, 2, and 3, wherein R$^1$ is —O(CH$_2$CH$_3$).

5. The compound of any one of claims 1, 2, and 3, wherein R$^1$ is

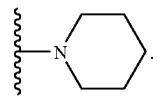

6. The compound of claim 2 or 3, wherein n is 2.

7. A compound of formula I(a):

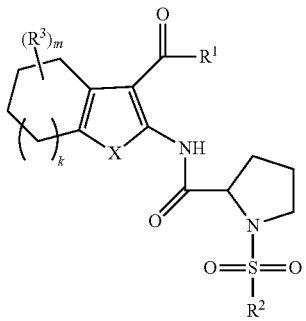

or a pharmaceutically acceptable salt thereof, wherein:

X is S or O;

R$^1$ is —(C$_1$-C$_{10}$ alkyl), —O(C$_1$-C$_{10}$ alkyl), —NH(C$_1$-C$_4$ alkyl), —N(C$_1$-C$_4$ alkyl)$_2$, R$^2$ is —(C$_1$-C$_{10}$ alkyl), —(C$_3$-C$_8$) cycloalkyl, phenyl, naphthyl, anthryl, phenanthryl, or -(5 to 7 membered) heteroaryl, each being unsubstituted or substituted with 1, 2, or 3 R$^3$ groups;

each R$^3$ is independently -halo, —C(halo)$_3$, —CH(halo)$_2$, —CH$_2$(halo), —CN, —OH, —NO$_2$, —NH$_2$, —NH(C$_1$-C$_4$ alkyl), —N(C$_1$-C$_4$ alkyl)$_2$, —(C$_1$-C$_{10}$ alkyl), —O(C$_1$-C$_4$ alkyl), —CONH$_2$, —CONH(C$_1$-C$_4$ alkyl), or —CON(C$_1$-C$_4$ alkyl)$_2$, each R$^4$ is independently -halo, —C(halo)$_3$, —CH(halo)$_2$, —CH$_2$(halo), —OH, —(C$_1$-C$_4$ alkyl), or —O(C$_1$-C$_4$ alkyl);

R$^5$ is —H, —C(halo)$_3$, —CH(halo)$_2$, —CH$_2$(halo), —(C$_1$-C$_{10}$ alkyl), —(CH$_2$)$_r$O(C$_1$-C$_4$ alkyl), —(CH$_2$)$_r$NH(C$_1$-C$_4$ alkyl), or —(CH$_2$)$_r$N(C$_1$-C$_4$ alkyl)$_2$, where r is an integer selected from the group consisting of 1, 2, 3, and 4;

each halo is independently —F, —Cl, —Br, or —I;

k is 2; and each m is independently an integer selected from the group consisting of 0, 1, 2, 3, and 4.

8. The compound of any one of claims 1, 2, and 3, wherein each m is 0.

9. The compound of any one of claims 1, 2, and 3, wherein R$^2$ is

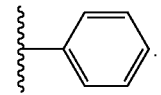

10. The compound of any one of claims 1, 2, and 3, wherein R² is
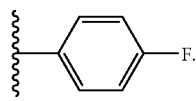
11. The compound of any one of claims 1, 2, and 3, wherein R² is
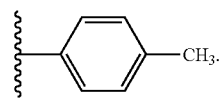
12. The compound of any one of claims 1, 2, and 3, wherein R² is
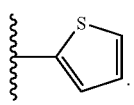
13. The compound of any one of claims 1, 2, and 3, wherein R² is
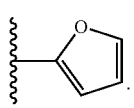
14. The compound of any one of claims 1, 2, and 3, wherein R² is
15. A compound of claim 7 selected from:
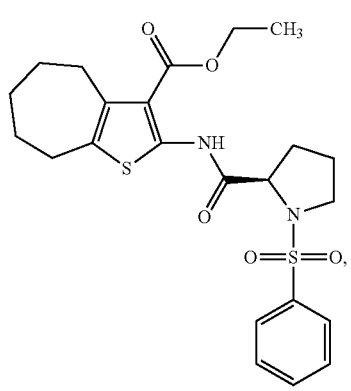
-continued
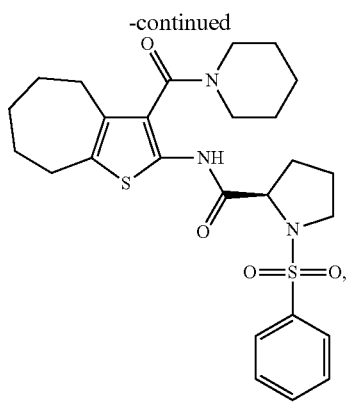
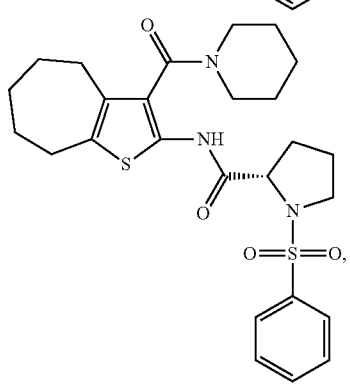
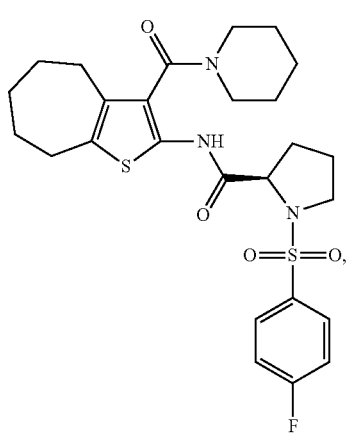
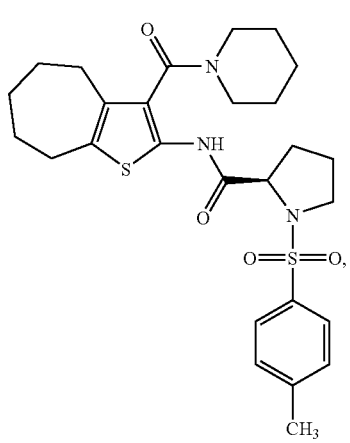

-continued

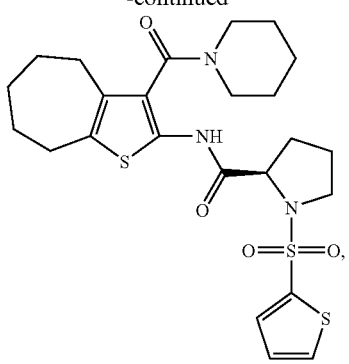

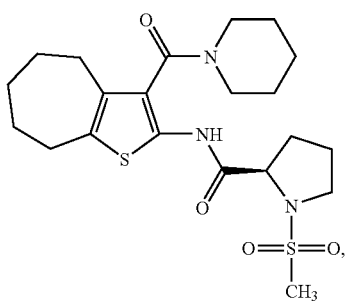

and pharmaceutically acceptable salts thereof.

16. The compound of any one of claims 1, 2, and 3, wherein X is S.

17. The compound of any one of claims 1, 2, and 3, wherein X is O.

18. A composition comprising a compound of any one of claims 1, 2, 3, and 7, or a pharmaceutically acceptable salt thereof and a pharmaceutically acceptable excipient.

19. A compound of claim 1 which is

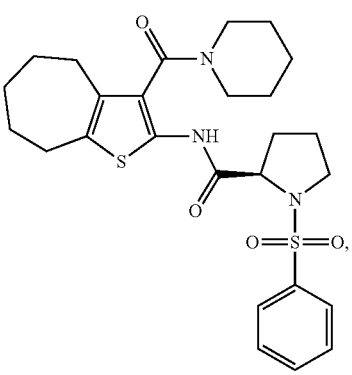

or a pharmaceutically acceptable salt thereof.

20. A compound of claim 2 which is

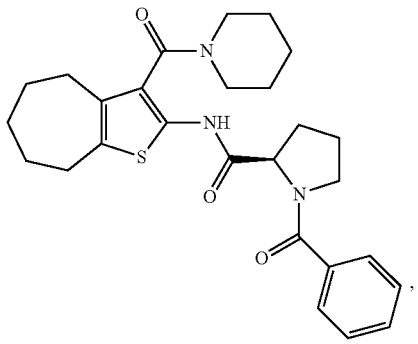

or a pharmaceutically acceptable salt thereof.

21. The compound of any one of claims 1, 2, and 3, wherein $R^1$ is

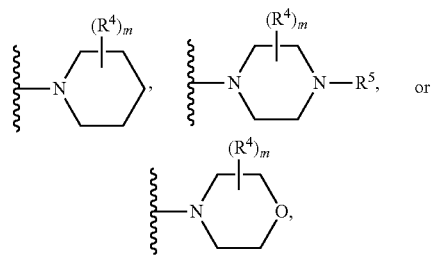

wherein m is 1 and $R^4$ is -halo, —C(halo)$_3$, —CH(halo)$_2$, —CH$_2$(halo), —OH, —(C$_1$-C$_4$ alkyl), or —O(C$_1$-C$_4$ alkyl).

22. The compound of claim 21, wherein $R^4$ is —OH or —O(C$_1$-C$_4$ alkyl), and $R^5$ is —(C$_1$-C$_{10}$ alkyl), —CH$_2$NH(C$_1$-C$_4$ alkyl), or —CH$_2$N(C$_1$-C$_4$ alkyl)$_2$.

23. The compound of any one of claims 1, 2, and 3, wherein $R^1$ is

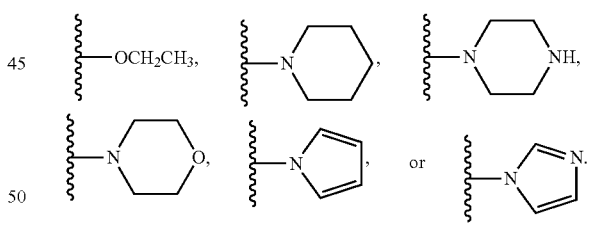

24. The compound of claim 23, wherein $R^1$ is

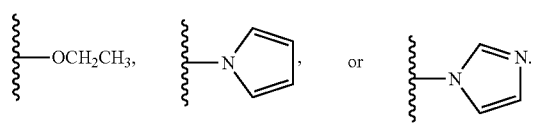

25. The compound of any one of claims 1, 2, and 3, wherein $R^1$ is —(C$_1$-C$_{10}$ alkyl), —O(C$_1$-C$_{10}$ alkyl), —NH(C$_1$-C$_4$ alkyl), or —N(C$_1$-C$_4$ alkyl)$_2$.

26. The compound of claim 25, wherein $R^1$ is —(C$_1$-C$_{10}$ alkyl).

27. The compound of claim 26, wherein $R^1$ is —(C$_1$-C$_4$ alkyl).

28. The compound of any one of claims 1, 2, and 3, wherein $R^2$ is
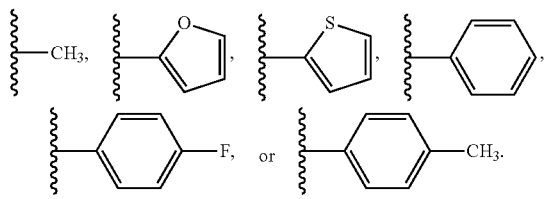
29. The compound of claim 28, wherein $R^2$ is
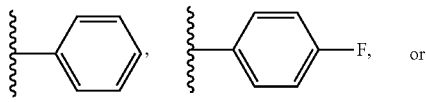
-continued
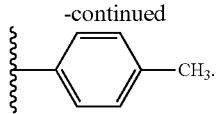
30. The compound of any one of claims 1, 2, and 3, wherein $R^2$ is —($C_1$-$C_{10}$ alkyl).
31. The compound of claim 30, wherein $R^1$ is —($C_1$-$C_4$ alkyl).
32. A kit comprising a container containing a compound or a pharmaceutically acceptable salt of a compound of any one of claims 1, 2, 3, and 7.
* * * * *